(12) United States Patent
Haning et al.

(10) Patent No.: US 6,794,406 B2
(45) Date of Patent: Sep. 21, 2004

(54) INDOLE DERIVATIVES

(75) Inventors: Helmut Haning, Milford, CT (US); Michael Woltering, Wuppertal (DE); Gunter Schmidt, Wuppertal (DE); Hilmar Bischoff, Wuppertal (DE); Axel Kretschmer, Wuppertal (DE); Verena Vöhringer, Wuppertal (DE); Christiane Faeste, Haan (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/026,023

(22) Filed: Dec. 21, 2001

(65) Prior Publication Data
US 2003/0078288 A1 Apr. 24, 2003

(30) Foreign Application Priority Data

Dec. 27, 2000 (DE) .......................................... 100 65 433
Jun. 27, 2001 (DE) .......................................... 101 30 830

(51) Int. Cl.⁷ .................... A61K 31/404; C07D 209/04
(52) U.S. Cl. .................... 514/414; 514/415; 514/227.2; 514/339; 514/369; 514/381; 514/391; 548/469; 548/504; 548/510; 548/467; 548/250; 548/252; 548/312.1; 548/181; 546/277.4; 544/54
(58) Field of Search ................................. 548/469, 504, 548/510, 467; 514/414, 415

(56) References Cited

U.S. PATENT DOCUMENTS 5,468,899 A    11/1995   Bauer, Jr. et al. ........... 560/218

FOREIGN PATENT DOCUMENTS

| | | |
|---|---|---|
| EP | 0188351 | 7/1986 |
| EP | 0377450 | 7/1990 |
| EP | 0580550 | 1/1994 |
| EP | 0639573 | 2/1995 |
| GB | 2253848 | 9/1992 |
| JP | 7145147 | 6/1995 |
| WO | 9414770 | 7/1994 |
| WO | 9426737 | 11/1994 |
| WO | 9520588 | 8/1995 |
| WO | 9806402 | 2/1998 |
| WO | 9811895 | 3/1998 |
| WO | 9857919 | 12/1998 |
| WO | 9926966 | 6/1999 |
| WO | 9950268 | 10/1999 |
| WO | 0039077 | 7/2000 |
| WO | 0051971 | 9/2000 |
| WO | 0058279 | 10/2000 |
| WO | 0059880 | 10/2000 |
| WO | 0170687 | 9/2001 |
| WO | 0176292 | 10/2001 |

OTHER PUBLICATIONS

Yokoyama, N., Walker, G. N., Main, A. J., Stanton, J. L., Morrissey, M. M., Boehm, C., Engle, A., Neubert, A D., Wasvary, J. M., Stephan, Z. F., and Steele, R. E., "Synthesis and Structure—Activity Relationships of Oxamic Acid and Acetic Acid Derivatives Related to L–Thyronine", J. Med. Chem., 38: 695–707 (1995).

*Primary Examiner*—Laura L. Stockton
(74) *Attorney, Agent, or Firm*—Susan M. Pellegrino

(57) ABSTRACT

The invention relates to new indole derivatives, processes for their preparation, and their use in medicaments.

14 Claims, No Drawings

INDOLE DERIVATIVES

The invention relates to new indole derivatives, processes for their preparation and their use in medicaments.

In EP-A-580 550, oxamic acid derivatives are described which have cholesterol-lowering properties in mammals. The reduction of plasma cholesterol, in particular of LDL cholesterol, is emphasized as a pharmacological property. Cholesterol-lowering actions are also described in EP-A-188 351 for certain diphenyl ethers having thyroid-hormone-like actions, which differ clearly in their chemical structure from the compounds according to the invention.

WO 00/51971 discloses oxamic acid derivatives having indole partial structure as thyroid receptor ligands for the treatment of various diseases.

Further indoles which are connected in the 5-position via a bridge member having a substituted phenyl ring are known (WO 94/14770; EP-A-674 619 A1 or WO 94/26737). No thyroid-hormone-like properties are described for these 5-substituted indoles.

WO 99/50268 discloses substituted indolealkanecarboxylic acids which are suitable for the treatment of chronic complications caused by diabetes mellitus.

WO 95/20588 discloses indole derivatives having action as $5\text{-HT}_1$ agonists.

WO 98/11895 discloses the use of $5\text{-HT}_1$ agonists for the treatment of migraine; indole derivatives are also indicated as suitable active compounds. In WO 98/06402, use for the treatment of coryza or rhinitis is described for the same structures.

EP-A-639 573 discloses benzo-fused 5-membered ring heterocycles and their use in medicaments and diagnostics. The disclosed compounds are inhibitors of the cellular sodium-proton antiporter ($Na^+/H^+$ exchanger).

U.S. Pat. No. 5,468,899 relates to bicyclic aryl compounds having selective properties as $LTB_4$ antagonists.

EP-A-377 450 discloses substituted indole, benzofuran and benzothiophene derivatives having action as 5-lipoxygenase inhibitors.

JP-A-07145 147 discloses testosterone 5-alpha-reductase inhibitors derived from benzoic acid, which can be employed for the treatment of prostate cancer and certain hair loss disorders.

In GB-A-2 253 848, phenylindole ethers di-ortho-substituted in the phenyl moiety and having herbicidal action are described which can be employed as crop protection agents. Thyromimetic actions have hitherto not been published for these ortho-substituted indoles.

The object of the invention is the provision of new compounds having improved actions, in particular pharmaceutical actions.

It has now been found that compounds of the general formula (I)

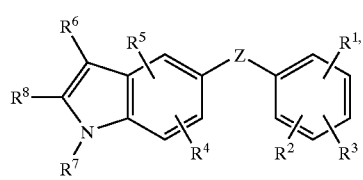

in which

Z represents O, S, SO, $SO_2$, $CH_2$, CHF, $CF_2$ or represents $NR^9$, in which $R^9$ denotes hydrogen or $(C_1-C_4)$-alkyl, $R^1$ and $R^2$ are identical or different and represent hydrogen, halogen, cyano, $(C_1-C_6)$-alkyl, $CF_3$, $CHF_2$, $CH_2F$, vinyl or $(C_3-C_7)$-cycloalkyl, where at least one of the two substituents is unequal to hydrogen and in the ortho position to the bridge bond, $R^3$ represents a group of the formula

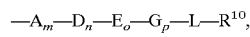

in which

A represents O, S, $NR^{11}$ or represents the group $-(CR^{12}=CR^{13})-$, in which $R^{11}$ denotes hydrogen or $(C_1-C_4)$-alkyl, and $R^{12}$ and $R^{13}$ are identical or different and denote hydrogen, cyano, $(C_1-C_4)$-alkyl or $(C_1-C_4)$-alkoxy, D represents a straight-chain $(C_1-C_3)$-alkylene group, which can be mono- or polysubstituted, identically or differently, by $(C_1-C_4)$-alkyl, hydroxyl, $(C_1-C_4)$-alkoxy, halogen, amino, mono-$(C_1-C_4)$-alkylamino, mono-$(C_1-C_4)$-acylamino or $(C_1-C_4)$-alkoxycarbonylamino, E and L independently of one another represent a C(O) or $SO_2$ group, G represents $NR^{14}$, in which $R^{14}$ denotes hydrogen or $(C_1-C_4)$-alkyl, or represents a straight-chain $(C_1-C_3)$-alkylene group, which can be mono- or polysubstituted, identically or differently, by $(C_1-C_4)$-alkyl, hydroxyl, $(C_1-C_4)$-alkoxy, halogen, amino, mono- or di-$(C_1-C_4)$-alkylamino or mono-$(C_1-C_4)$-acylamino, m, n, o and p independently of one another in each case represent the number 0 or 1, with the proviso that in the case that L represents a C=O group, the sum (m+n+o+p) is unequal to the number 0, and in the case that m and o in each case represent the number 1, A represents the radical $NR^{11}$ and E and L in each case represent a C=O group, the sum (n+p) is unequal to the number 0, and $R^{10}$ represents $OR^{15}$, $NR^{16}R^{17}$, $(C_1-C_{10})$-alkyl, $(C_3-C_8)$-cycloalkyl, $(C_2-C_6)$-alkenyl, $(C_6-C_{10})$-aryl, $(C_6-C_{10})$-arylmethyl or represents a saturated, partly unsaturated or aromatic 5- to 10-membered heterocycle having up to four identical or different heteroatoms from the group consisting of N, O and/or S, where the above-mentioned radicals are optionally substituted by one, two or three identical or different substituents selected from the group consisting of halogen, hydroxyl, oxo, cyano, nitro, amino, $NR^{18}R^{19}$, trifluoromethyl, $(C_1-C_6)$-alkyl, $(C_1-C_6)$-alkoxy optionally substituted by $R^{20}$, $(C_3-C_8)$-cycloalkyl, $(C_6-C_{10})$-aryl, which for its part is optionally substituted by halogen, $(C_1-C_4)$-alkyl, $(C_1-C_4)$-alkoxy, trifluoromethyl, nitro or cyano; $-O-C(O)-R^{21}$, $-C(O)-OR^{22}$, $-C(O)-NR^{23}R^{24}$, $-SO_2-NR^{25}R^{26}$, $-NH-C(O)-R^{27}$ and $-NH-C(O)-OR^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_8)$-cycloalkyl, which for their part are optionally mono- or polysubstituted, identically or differently, by halogen, hydroxyl, amino, carboxyl, $(C_1-C_4)$-alkoxy, $(C_1-C_4)$-alkoxycarbonyl, $(C_1-C_4)$-alkoxy-carbonyl-amino, $(C_1-C_5)$-alkanoyloxy, a heterocycle or phenyl which is optionally substituted by halogen or hydroxyl, or the group
—L—R$^{10}$ represents a group of the formula

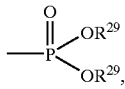

in which
R$^{29}$ denotes hydrogen or (C$_1$–C$_4$)-alkyl,
or
R$^3$ represents a group of the formula

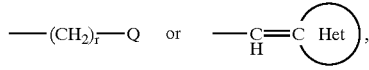

in which
Q represents a 5- to 6-membered saturated, partly unsaturated or aromatic heterocycle having up to four identical or different heteroatoms from the group consisting of N, O and/or S, which for its part is optionally mono- to trisubstituted, identically or differently, by oxo (=O), thioxo (=S), hydroxyl, (C$_1$–C$_6$)-alkyl or phenyl,
r represents the number 0, 1 or 2,
and
the ring Het denotes a 5- to 6-membered saturated or partly unsaturated heterocycle having up to three identical or different heteroatoms from the group consisting of N, O and/or S, which is optionally mono- to trisubstituted, identically or differently, by oxo (=O), thioxo (=S), hydroxyl, (C$_1$–C$_6$)-alkyl or phenyl,
R$^4$ and R$^5$ are identical or different and in each case represent hydrogen, hydroxyl, halogen, cyano, nitro, (C$_1$–C$_4$)-alkyl or the radical of the formula NR$^{30}$R$^{31}$, where R$^{30}$ and R$^{31}$ have the meaning indicated for R$^{15}$ and independently of one another can be identical to or different from this substituent,
R$^6$ represents hydrogen, halogen or represents a group of the formula

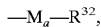

in which
M represents a carbonyl group, a sulphonyl group or a methylene group,
a represents the number 0 or 1,
and
R$^{32}$ has the meaning of R$^{10}$ indicated above and can be identical to or different from this substituent,
R$^7$ represents hydrogen or represents an acyl group which can be removed under physiological conditions with formation of an NH function, preferably represents hydrogen or acetyl,
and
R$^8$ has the meaning of R$^6$ indicated above and can be identical to or different from this substituent,
and their pharmaceutically tolerable salts, solvates, hydrates and hydrates of the salts,
preferably the compounds which are trisubstituted, in particular tetrasubstituted, in the phenyl moiety and preferably in the 1-, 2-, 4- and 6-position and have a substituent in the 3-position in the indole ring,
exhibit a pharmacological action and can be used as medicaments or for the preparation of pharmaceutical formulations.

Heterocycles in the definition of R$^6$, R$^8$ or R$^{10}$ which may preferably be mentioned are:
A 5- to 10-membered saturated, partly unsaturated or aromatic, optionally benzofused heterocycle having up to 4 heteroatoms from the group consisting of S, N and/or O, i.e. a heterocycle, which can contain one or more double bonds and which is linked via a ring carbon atom or a ring nitrogen atom. Examples which may be mentioned are: tetrahydrofuryl, pyrrolidinyl, pyrrolinyl, piperidinyl, 1,2-dihydropyridinyl, 1,4-dihydropyridinyl, piperazinyl, morpholinyl, azepinyl, 1,4-diazepinyl, furanyl, pyrrolyl, thienyl, thiazolyl, oxazolyl, imidazolyl, triazolyl, tetrazolyl, pyridyl, pyrimidinyl, pyrazinyl, pyridazinyl, pyrimidinonyl, pyridazinonyl.
Preferred heterocycles fom this list are: pyridyl, pyrimidinyl, pyridazinyl, pyrimidinonyl, pyridazinonyl and thienyl.
Alkyl in the context of the invention represents a straight-chain or branched alkyl radical preferably having 1 to 15, 1 to 12, 1 to 10, 1 to 8, 1 to 6, 1 to 4 or 1 to 3 carbon atoms. A straight-chain or branched alkyl radical having 1 to 3 carbon atoms is preferred. The following may be mentioned by way of example and preferably: methyl, ethyl, n-propyl, isopropyl, n-, i-, s- or t-butyl, n-pentyl and n-hexyl.
Aryl in the context of the invention represents an aromatic radical preferably having 6 to 10 carbon atoms. Preferred aryl radicals are phenyl and naphthyl.
Cycloalkyl in the context of the invention represents a cycloalkyl group preferably having 3 to 8, 3 to 7 or 3 to 6 carbon atoms. The following may be mentioned by way of example and preferably: cyclopropyl, cyclobutyl, cyclopentyl, cyclohexyl and cycloheptyl.
Alkoxy in the context of the invention preferably represents a straight-chain or branched alkoxy radical having 1 to 6, 1 to 4 or 1 to 3 carbon atoms. A straight-chain or branched alkoxy radical having 1 to 3 carbon atoms is preferred. The following may be mentioned by way of example and preferably: methoxy, ethoxy, n-propoxy, isopropoxy, t-butoxy, n-pentoxy and n-hexoxy.
Alkoxycarbonyl in the context of the invention preferably represents a straight-chain or branched alkoxy radical having 1 to 6 or 1 to 4 carbon atoms, which is linked via a carbonyl group. A straight-chain or branched alkoxycarbonyl radical having 1 to 4 carbon atoms is preferred. The following may be mentioned by way of example and preferably: methoxycarbonyl, ethoxycarbonyl, n-propoxycarbonyl, isopropoxycarbonyl and t-butoxycarbonyl.
Alkanoyloxy in the context of the invention preferably represents a straight-chain or branched alkyl radical having 1 to 6, 1 to 5 or 1 to 3 carbon atoms, which in the 1-position carries a doubly bonded oxygen atom and is linked in the 1-position via a further oxygen atom. A straight-chain or branched alkanoyloxy radical having 1 to 3 carbon atoms is preferred. The following may be mentioned by way of example and preferably: acetoxy, propionoxy, n-butyroxy, i-butyroxy, pivaloyloxy and n-hexanoyloxy.
Monoalkylamino in the context of the invention represents an amino group having a straight-chain or branched alkyl substituent, which preferably has 1 to 6, 1 to 4 or 1 to 2 carbon atoms. A straight-chain or branched monoalkylamino radical having 1 to 4 carbon atoms is preferred. The following may be mentioned by way of example and preferably: methylamino, ethylamino, n-propylamino, isopropylamino, t-butylamino, n-pentylamino and n-hexylamino.
Dialkylamino in the context of the invention represents an amino group having two identical or different straight-chain or branched alkyl substituents, which preferably in each case have 1 to 6, 1 to 4 or 1 to 2 carbon atoms. Straight-chain or branched dialkylamino radicals in each case having 1 to 4 carbon atoms are preferred. The following may be mentioned by way of example and preferably: N,N-dimethylamino, N,N-diethylamino, N-ethyl-N-methylamino, N-methyl-N-n-propylamino, N-isopropyl-N-n-propylamino, N-t-butyl-N-methylamino, N-ethyl-N-n-pentylamino and N-n-hexyl-N-methylamino.

Monoacylamino in the context of the invention represents an amino group having a straight-chain or branched alkanoyl substituent, which preferably has 1 to 6, 1 to 4 or 1 to 2 carbon atoms and is linked via the carbonyl group. A monoacylamino radical having 1 to 2 carbon atoms is preferred. The following may be mentioned by way of example and preferably: formamido, acetamido, propionamido, n-butyramido and pivaloylamido.

Alkoxycarbonylamino in the context of the invention represents an amino group having a straight-chain or branched alkoxycarbonyl substituent, which in the alkoxy radical preferably has 1 to 6 or 1 to 4 carbon atoms and is linked via the carbonyl group. An alkoxycarbonylamino radical having 1 to 4 carbon atoms is preferred. The following may be mentioned by way of example and preferably: methoxycarbonylamino, ethoxycarbonylamino, n-propoxycarbonylamino and t-butoxycarbonylamino.

Halogen in the context of the invention includes fluorine, chlorine, bromine and iodine. Fluorine, chlorine and bromine are preferred.

Depending on the substituent pattern, the compounds according to the invention can exist in stereoisomeric forms, which either behave as image and mirror image (enantiomers), or which do not behave as image and mirror image (diastereomers). The invention relates both to the enantiomers or diastereomers and to their respective mixtures. Like the diastereomers, the racemic forms can be separated into the stereoisomerically uniform constituents in a known manner.

Furthermore, certain compounds can be present in tautomeric forms. This is known to the person skilled in the art, and compounds of this type are likewise included by the scope of the invention.

The compounds according to the invention can also be present as salts. In the context of the invention, physiologically acceptable salts are preferred.

Physiologically acceptable salts can be salts of the compounds according to the invention with inorganic or organic acids. Preferred salts are those with inorganic acids such as, for example, hydrochloric acid, hydrobromic acid, phosphoric acid or sulphuric acid, or salts with organic carboxylic or sulphonic acids such as, for example, acetic acid, propionic acid, maleic acid, fumaric acid, malic acid, citric acid, tartaric acid, lactic acid, benzoic acid, or methanesulphonic acid, ethane-sulphonic acid, benzenesulphonic acid, toluenesulphonic acid or naphthalenedisulphonic acid.

Physiologically acceptable salts can likewise be salts of the compounds according to the invention with bases, such as, for example, metal or ammonium salts. Preferred examples are alkali metal salts (e.g. sodium or potassium salts), alkaline earth metal salts (e.g. magnesium or calcium salts), and ammonium salts, which are derived from ammonia or organic amines, such as, for example, ethylamine, di- or triethylamine, ethyldiisopropylamine, monoethanolamine, di- or triethanolamine, dicyclohexylamine., dimethylaminoethanol, dibenzylamine, N-methylmorpholine, dihydroabietylamine, 1-ephenamine, methylpiperidine, arginine, lysine, ethylenediamine or 2-phenylethylamine.

The compounds according to the invention can also be present in the form of their solvates, in particular in the form of their hydrates.

Moreover, the invention also includes prodrugs of the compounds according to the invention. "Prodrugs" are designated according to the invention as those derivatives of the compounds of the general formula (I) which can be biologically less active or even inactive themselves, but after administration are converted under physiological conditions into the corresponding biologically active form (for example metabolically, solvolytically or in another manner).

Preferred compounds of the general formula (I) are those in which

Z represents O, S or $CH_2$, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_5)$-cycloalkyl, where at least one of the two substituents is unequal to hydrogen and is in the ortho position to the bridge bond, in particular both substituents are unequal to hydrogen and both are in the ortho position, $R^3$ represents a group of the formula

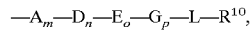

in which

A represents O, S, $NR^{11}$, or represents the group —$(CR^{12}=CR^{13})$—, in which $R^{11}$ denotes hydrogen or methyl, and $R^{12}$ and $R^{13}$ are identical or different and denote hydrogen or methoxy, D represents a straight-chain $(C_1-C_3)$-alkylene group which can be mono- or disubstituted, identically or differently, by $(C_1-C_4)$-alkyl, hydroxyl, methoxy, ethoxy, fluorine, chlorine, amino, mono-$(C_1-C_4)$-alkylamino or mono-$(C_1-C_4)$-acylamino, E represents a C(O) group, L represents a C(O) or $SO_2$ group, G represents an NH group or represents a straight-chain $(C_1-C_3)$-alkylene group, which can be mono- or disubstituted, identically or differently, by methyl, ethyl, hydroxyl, methoxy, fluorine, chlorine, amino, methylamino or acetylamino, m, n, o and p independently of one another in each case represent the number 0 or 1, with the proviso that in the case that L represents a C=O group, the sum (m+n+o+p) is unequal to the number 0, and in the case that m and o in each case represent the number 1, A represents the radical $NR^{11}$ and L represents a C=O group, the sum (n+p) is unequal to the number 0, and $R^{10}$ represents $OR^{15}$, $NR^{16}R^{17}$, $(C_1-C_6)$-alkyl, $(C_3-C_7)$-cycloalkyl, naphthyl, phenyl, benzyl or represents a saturated, partly unsaturated or aromatic 5- to 6-membered heterocycle having up to four identical or different heteroatoms from the group consisting of N, O and/or S, where the abovementioned radicals are optionally substituted by one, two or three identical or different substituents selected from the group consisting of halogen, hydroxyl, oxo, cyano, nitro, amino, $NR^{18}R^{19}$, trifluoromethyl, $(C_1-C_4)$-alkyl, $(C_1-C_4)$-alkoxy optionally substituted by $R^{20}$, $(C_3-C_6)$-cycloalkyl, —O—C(O)—$R^{21}$, —C(O)—$OR^{22}$, —C(O)—$NR^{23}R^{24}$, —$SO_2NR^{25}R^{26}$, —NH—C(O)—$R^{27}$ and —NH—C(O)—$OR^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or polysubstituted, identically or differently, by halogen, hydroxyl, amino, carboxyl, $(C_1-C_4)$-alkoxy, $(C_1-C_4)$-alkoxycarbonyl, $(C_1-C_4)$-alkoxy-carbonylamino, $(C_1-C_5)$-alkanoyloxy, a heterocycle or phenyl which is optionally substituted by halogen or hydroxyl, or $R^3$ represents a group of the formula

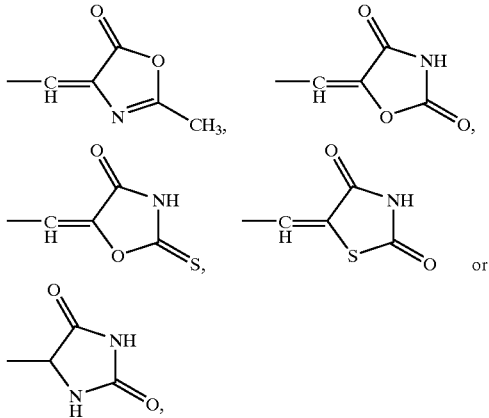

$R^4$ and $R^5$ are identical or different and in each case represent hydrogen, halogen or $(C_1-C_4)$-alkyl, $R^6$ represents hydrogen, halogen or a group of the formula $$-M_a-R^{32},$$

in which

M represents a carbonyl group, a sulphonyl group or a methylene group, a represents the number 0 or 1, and $R^{32}$ represents $(C_1-C_{10})$-alkyl, $(C_3-C_7)$-cycloalkyl, $(C_2-C_4)$-alkenyl, naphthyl, phenyl, benzyl, pyridyl, pyridazinyl or pyridazinonyl, where the abovementioned radicals are optionally substituted by one, two or three identical or different substituents selected from the group consisting of halogen, hydroxyl, cyano, nitro, amino, $NR^{18}R^{19}$, trifluoromethyl, $(C_1-C_4)$-alkyl, $(C_1-C_4)$-alkoxy, $(C_3-C_7)$-cycloalkyl, phenyl, which for its part is optionally substituted by halogen, $(C_1-C_4)$-alkyl, $(C_1-C_4)$-alkoxy, trifluoromethyl, nitro or cyano, $-OC(O)-R^{21}$, $-C(O)-OR^{22}$, $-C(O)-NR^{23}R^{24}$, $-SO_2-NR^{25}R^{26}$, $-NH-C(O)-R^{27}$ and $-NH-C(O)-OR^{28}$, where $R^{18}$, $R^{19}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or polysubstituted, identically or differently, by halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or phenyl which is optionally substituted by halogen or hydroxyl, $R^7$ represents hydrogen, and $R^8$ has the meaning of $R^6$ indicated above and can be identical to or different from this substituent, and their pharmaceutically tolerable salts, solvates, hydrates and hydrates of the salts.

Particularly preferred compounds of the general formula (I) are those in which

Z represents O or $CH_2$, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_5)$-cycloalkyl, where at least one of the two substituents is unequal to hydrogen and in the ortho position to the bridge bond, in particular both substituents are unequal to hydrogen and both are in the ortho position, $R^3$ represents a group of the formula $$-A_m-D_n-E_o-G_p-L-R^{10},$$

in which

A represents O, S or NH,

D represents a straight-chain $(C_1-C_3)$-alkylene group, which can be mono- or disubstituted, identically or differently, by methyl, ethyl, hydroxyl, methoxy, fluorine, amino or acetylamino, E represents a C(O) group, L represents a C(O) or $SO_2$ group, G represents an NH group or represents a methylene group, m, n, o and p independently of one another in each case represent the number 0 or 1, with the proviso that in the case that L represents a C=O group, the sum (m+n+o+p) is unequal to the number 0, and in the case that m and o in each case represent the number 1, A represents the radical NH and L represents a C=O group, the sum (n+p) is unequal to the number 0, and $R^{10}$ represents $OR^{15}$, $NR^{16}R^{17}$, $(C_1-C_6)$-alkyl, phenyl, benzyl or represents an aromatic 5- to 6-membered heterocycle having up to four identical or different heteroatoms from the group consisting of N, O and/or S, where the abovementioned radicals are optionally substituted by one, two or three identical or different substituents selected from the group consisting of fluorine, chlorine, hydroxyl, oxo, cyano, nitro, amino, $NR^{18}R^{19}$, trifluoromethyl, $(C_1-C_4)$-alkyl, $(C_1-C_4)$-alkoxy optionally substituted by $R^{20}$, $(C_3-C_6)$-cycloalkyl, $-O-C(O)-R^{21}$, $-C(O)-OR^{22}$, $-C(O)-NR^{23}R^{24}$, $-SO_2-NR^{25}R^{26}$, $-NH-C(O)-R^{27}$ and $-NH-C(O)-OR^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- to disubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or phenyl which is optionally substituted by fluorine, chlorine or hydroxyl, $R^4$ and $R^5$ are identical or different and in each case represent hydrogen, fluorine, chlorine or methyl, $R^6$ represents hydrogen, halogen or a group of the formula $$-M_a-R^{32},$$

in which

M represents a sulphonyl group or a methylene group, a represents the number 0 or 1, and $R^{32}$ represents $(C_1-C_{10})$-alkyl, $(C_3-C_7)$-cycloalkyl, phenyl, benzyl, pyridyl, pyridazinyl or pyridazinonyl, where the abovementioned radicals are optionally substituted by one or two identical or different substituents selected from the group consisting of fluorine, chlorine, bromine, hydroxyl, cyano, nitro, amino, $NR^{18}R^{19}$, trifluoromethyl, $(C_1-C_4)$-alkyl, $(C_1-C_4)$-alkoxy, $(C_3-C_7)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or disubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonyl-amino, $(C_1-C_5)$-alkanoyloxy, a heterocycle or phenyl which is optionally substituted by fluorine, chlorine or hydroxyl, $R^7$ represents hydrogen, $R^8$ represents hydrogen, carboxyl, $(C_1-C_4)$-alkoxycarbonyl, $(C_1-C_6)$-alkyl, $(C_3-C_7)$-cycloalkyl, phenyl, benzyl, pyridyl, phenylsulphonyl or benzylsulphonyl, where the abovementioned radicals are optionally substituted by one or two identical or different substituents selected from the group consisting of fluorine, chlorine, bromine, hydroxyl, cyano, nitro, amino, $NR^{18}R^{19}$, trifluoromethyl, $(C_1-C_4)$-alkyl, $(C_1-C_4)$-alkoxy, $(C_3-C_6)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or polysubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or phenyl which is optionally substituted by fluorine, chlorine or hydroxyl, and their pharmaceutically tolerable salts, solvates, hydrates and hydrates of the salts.

Very particularly preferred compounds of the general formula (I) are those in which Z represents O, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_5)$-cycloalkyl, where at least one of the two substituents is unequal to hydrogen and in the ortho position to the bridge bond, in particular both substituents are unequal to hydrogen and both are in the ortho position, $R^3$ represents a group of the formula

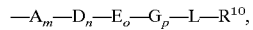—$A_m$—$D_n$—$E_o$—$G_p$—L—$R^{10}$, in which

A represents O, S or NH,

D represents a methylene or ethylene group, which can be mono- to disubstituted, identically or differently, by methyl, ethyl, fluorine, amino or acetylamino, E represents a C(O) group, L represents a C(O) or $SO_2$ group, G represents an NH group or represents a methylene group, m, n, o and p independently of one another in each case represent the number 0 or 1, with the proviso that in the case that L represents a C=O group, the sum (m+n+o+p) is unequal to the number 0, and in the case that m and o in each case represent the number 1, A represents the radical NH and L represents a C=O group, the sum (n+p) is unequal to the number 0, and $R^{10}$ represents $OR^{15}$, $NR^{16}R^{17}$ or represents $(C_1-C_4)$-alkyl, where $R^{15}$, $R^{16}$ and $R^{17}$ are identical or different and in each case represent hydrogen, phenyl, benzyl, $(C_1-C_6)$-alkyl or $(C_3-C_6)$-cycloalkyl, which for their part are optionally mono- to disubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a hetero cycle or phenyl, $R^4$ and $R^5$ are identical or different and in each case represent hydrogen, fluorine, chlorine or methyl, $R^6$ represents hydrogen, halogen, $(C_1-C_{10})$-alkyl, $(C_3-C_7)$-cycloalkyl, $(C_3-C_7)$-cycloalkylmethyl, phenyl, benzyl, pyridazinonylmethyl, phenylsulphonyl or pyridylsulphonyl, where the abovementioned aromatic radicals are optionally substituted by one or two identical or different substituents selected from the group consisting of fluorine, chlorine, cyano, nitro, trifluoromethyl, methyl, methoxy, carboxyl or methoxycarbonyl, $R^7$ represents hydrogen, $R^8$ represents hydrogen, $(C_1-C_6)$-alkyl, $(C_3-C_7)$-cycloalkyl, phenyl, benzyl, phenylsulphonyl or benzylsulphonyl, where the abovementioned aromatic radicals are optionally substituted by one or two identical or different substituents selected from the group consisting of fluorine, chlorine, cyano, trifluoromethyl, methyl or methoxy, and their pharmaceutically tolerable salts, solvates, hydrates and hydrates of the salts.

Compounds of the general formula (I) which are of particular importance are those in which Z represents $CH_2$ or in particular represents oxygen, $R^1$ and $R^2$ are identical or different and represent methyl, ethyl, propyl, isopropyl, chlorine, bromine, $CF_3$, vinyl or cyclopropyl, where both substituents are in the ortho position to the bridge bond, $R^4$ and $R^5$ independently of one another represent methyl, fluorine or chlorine or in particular represent hydrogen, and $R^7$ represents hydrogen.

The abovementioned radical definitions which are general or indicated in preferred ranges apply both to the final products of the formula (I) and correspondingly to the starting substances or intermediates needed in each case for preparation.

The radical definitions specifically indicated in the respective combinations or preferred combinations of radicals are arbitrarily also replaced, independently of the respective combinations of the radicals indicated, by radical definitions of other combinations.

Particularly preferred compounds of the formula (I) are those in which Z represents oxygen.

Particularly preferred compounds of the formula (I) are those in which $R^3$ represents a group of the formula

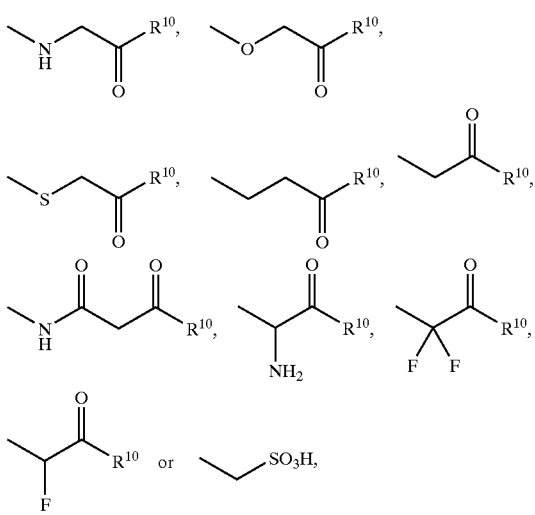

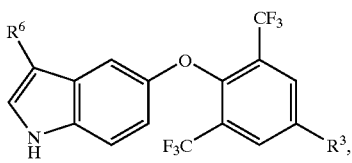

which is located in the para position to the bridge bond and in which $R^{10}$ represents hydroxyl or the radical —C(O)—$R^{10}$ has the indicated meanings of $R^{10}$ for a group which, in the sense of a prodrug, can be broken down to the carboxylic acid —C(O)—OH or its salts.

Particularly preferred compounds of the formula (I) are those in which $R^4$, $R^5$ and $R^7$ represent hydrogen.

Particularly preferred compounds of the formula (I) are those in which $R^1$ and $R^2$ are both situated in the ortho position to Z and represent bromine, trifluoromethyl, ethyl, cyclopropyl and in particular represent methyl or chlorine.

Very particularly preferred compounds of the formula (Ia)

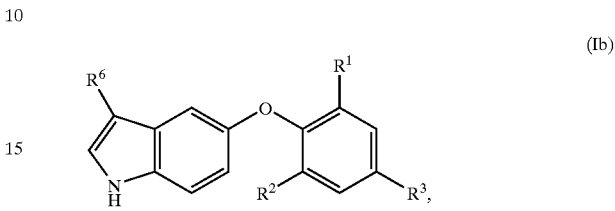

(Ia)

are those in which $R^3$ represents a group of the formula —CH$_2$—C(O)—OH, —CHF—C(O)—OH or —CF$_2$—C(O)—OH, and $R^6$ represents straight-chain or branched (C$_1$–C$_8$)-alkyl.

Very particularly preferred compounds of the formula (Ib)

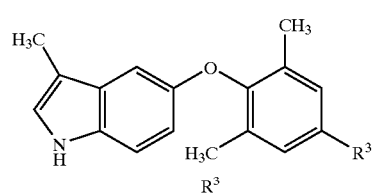

(Ib)

are likewise those in which $R^1$ and $R^2$ are identical or different and represent bromine, trifluoromethyl, ethyl, cyclopropyl and in particular represent methyl or chlorine, $R^3$ represents a group of the formula —NH—C(O)—CH$_2$—C(O)—$R^{10}$, in which $R^{10}$ represents hydroxyl or the radical —C(O)—$R^{10}$ has the meanings of $R^{10}$ indicated above for a group, which in the sense of a prodrug can be broken down to the carboxylic acid —C(O)—OH or its salts, and $R^6$ represents straight-chain or branched (C$_1$–C$_8$)-alkyl.

The following individual compounds may be mentioned by way of example and preferably:

Compounds of the formula 1 in which $R^3$ has the meanings indicated in Table 1 (* in the table denotes the linkage site):

TABLE 1

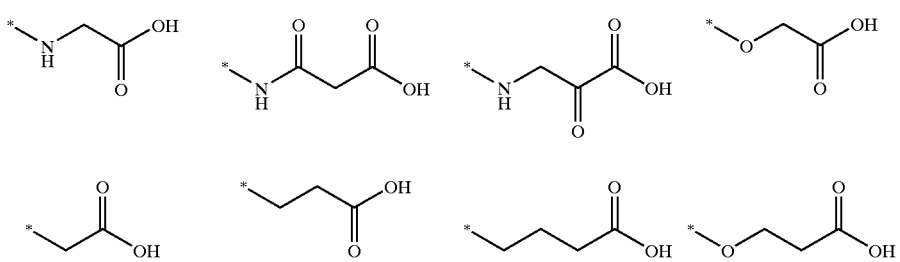

TABLE 1-continued
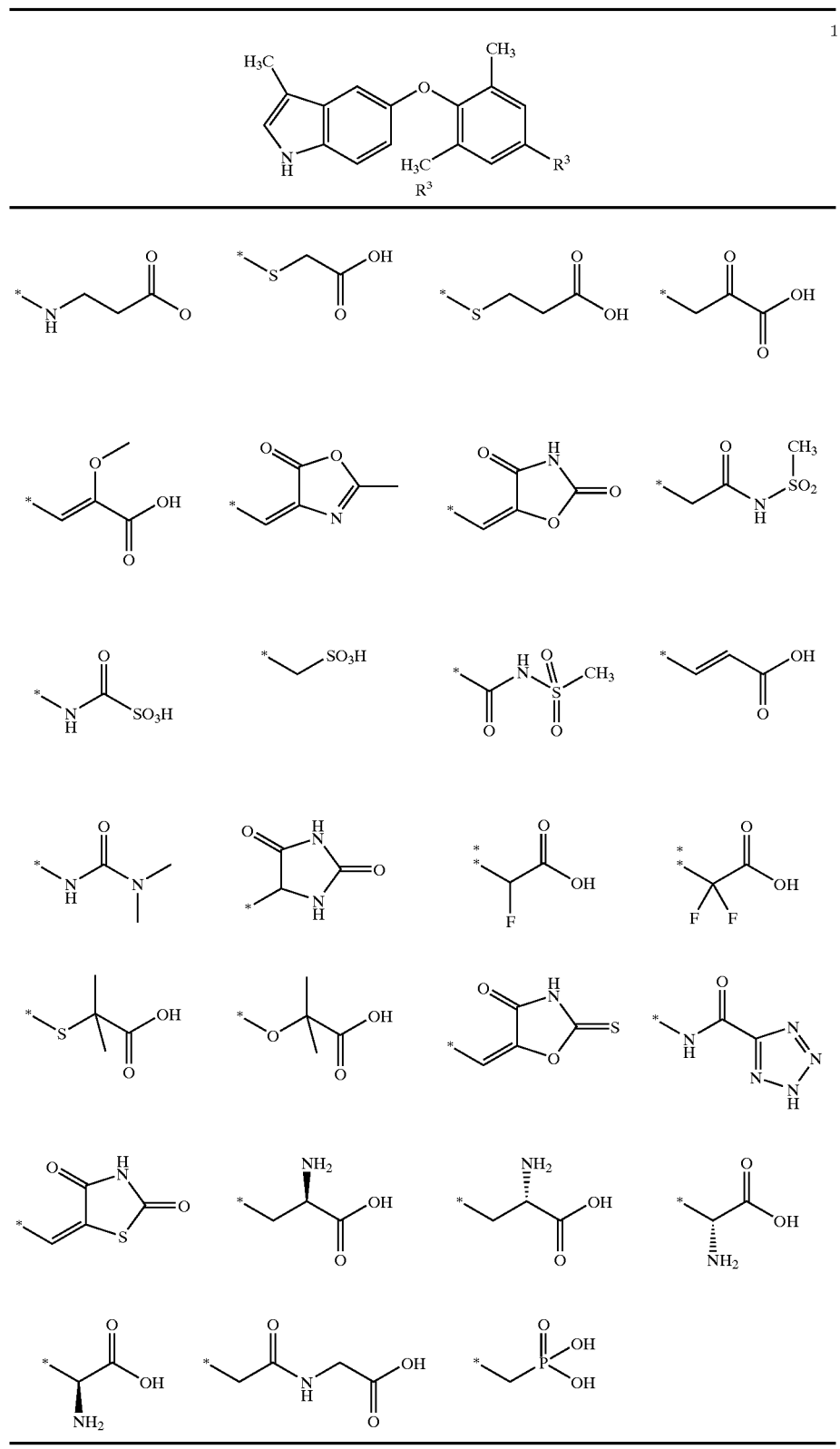
Individual compounds of the formula 2 in which $R^3$ in each case has the meanings indicated in Table 1 and $R^2$, instead of methyl from the formula 1, for each of the individual compounds 1 to 35 in each case has the meanings indicated in Table 2 for $R^2$:

TABLE 2

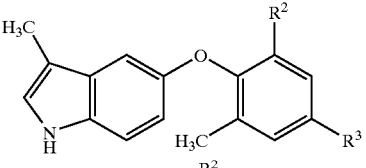

| H | F | Cl | Br |
|---|---|----|----|
| I | *—CH₃ | *—CH₂CH₃ | *—cyclopropyl |
| *—CH=CH₂ | *—CH(CH₃)₂ | *—CF₃ | *—CF₂H |
| *—CFH₂ | CN | | |

Individual compounds of the formula 3 in which R² and R³ in each case have the meanings indicated in Tables 1 and 2 and R¹, instead of methyl from formula 2, for each of the individual compounds 1 to 490 in each case has the meanings indicated in Table 3 for R¹:

TABLE 3

| H | F | Cl | Br |
|---|---|----|----|
| I | *—CH₃ | *—CH₂CH₃ | *—cyclopropyl |
| *—CH=CH₂ | *—CH(CH₃)₂ | *—CF₃ | *—CF₂H |
| *—CFH₂ | CN | | |

Individual compounds of the formula 4 in which R¹, R² and R³ in each case have the meanings indicated in Tables 1, 2 and 3 and R⁶, instead of methyl from formula 3, for each of the individual compounds 1 to 6860 in each case has the meanings indicated in Table 4 for R⁶:

TABLE 4

| H | F | Cl | Br |
|---|---|----|----|
| I | *—CH₃ | *—CH₂CH₃ | *—CH₂CH₂CH₃ |
| *—C(CH₃)(CH₂CH₃)(CH₃) | *—CH(CH₃)CH₃ | *—CH₂CH₂CH₂CH₃ | *—CH(CH₃)CH₂CH₃ |
| *—CH₂CH(CH₃)CH₃ | *—CH(CH₃)CH(CH₃)CH₃ | *—C(CH₃)₂CH₃ | *—CF₃ |
| *—CF₂H | *—CFH₂ | *—CH₂CH₂CH₂CH₂CH₃ | *—CH(CH₃)CH(CH₃)CH₃ |
| *—CH₂CH(CH₃)CH₂CH₃ | *—C(CH₃)₃ | *—C(CH₃)₂CH₂CH₃ | *—CH(CH₃)CH₂CH₂CH₃ |

TABLE 4-continued
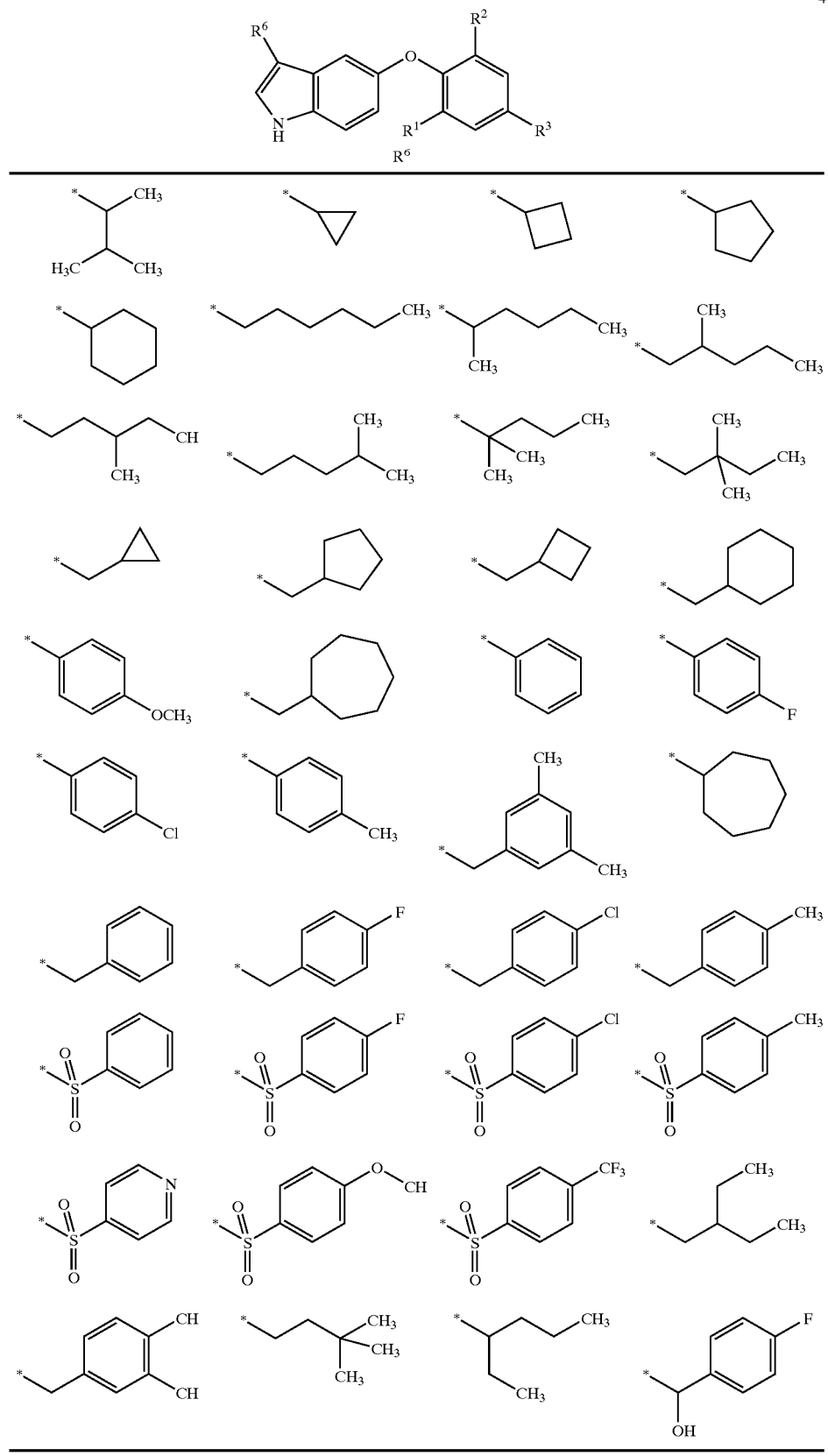

The compounds of the general formula (I) according to the invention can be prepared by reacting reactive indole derivatives of the general formula(II) with reactive phenyl derivatives of the general formula (III)

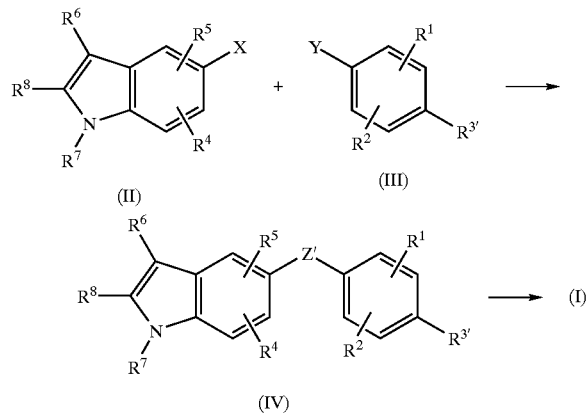

where the substituents $R^1$, $R^2$, $R^4$, $R^5$, $R^6$, $R^7$ and $R^8$ have the meanings indicated above, and $R^{3'}$ has the meaning indicated for $R^3$ or represents $NO_2$, $NH_2$, NH—PG, OH, O—PG, SH, S—PG, or represents an aldehyde, cyano, carboxyl or $(C_1-C_4)$-alkoxycarbonyl group, where PG represents a protective group, X and Y in each case represent groups of opposite reactivity, where, for example, X can be an electrophilic radical which reacts with a nucleophilic Y substituent and vice versa, Z' has the meaning indicated for Z or represents

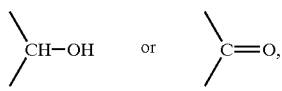

if appropriate in the presence of inert solvents and catalysts and if appropriate with isolation of the intermediates of the general formula (IV) or directly to give compounds of the formula (I).

Catalysts which may be mentioned by way of example are coupling catalysts such as Pd, Rh and/or Cu compounds.

Examples of the reactive groups X and Y which may be mentioned are: halogen, hydroxyl, $CH_2Br$, mercapto, amino, CHO, Li, magnesium, tin or boron derivatives.

The indoles of the general formula (II) which can be employed according to the invention are known or can be prepared according to known methods [compare, for example, Ozaki et al., Heterocycles 51, 727–731 (1999); Harvey et al., J. Chem. Soc., 473 (1959); Quadbeck et al., Hoppe-Seyler's Z. Physiolog. Chem. 297, 229 (1954); Chen et al., J. Org. Chem. 59, 3738 (1994); Synthesis, 480 (1988); J. prakt. Chem. 340, 608 (1998)].

The phenyl derivatives of the general formula (III) are likewise known or can be prepared according to known methods [compare, for example, van de Bunt, Recl. Trav. Chim. Pays-Bas 48, 131 (1929); Valkanas, J. Chem. Soc., 5554 (1963)].

The reaction of the starting compounds (II) with (III) in general proceeds at normal pressure. However, it can also be carried out at elevated or reduced pressure.

The reaction can be carried out in a temperature range from −100° C. to 200° C., preferably between −78° C. and 150° C., in the presence of inert solvents. Inert solvents which may preferably be mentioned are: dimethylsulphoxide (DMSO), dimethylformamide (DMF), N-methyl-2-pyrrolidinone (NMP), tetrahydrofuran (THF), diethyl ether, dichloromethane etc.

Depending on the specific substituent pattern, in the reaction of (II) and (III) intermediates of the formula (IV) can also be formed in which, for example, the substituent $R^{3'}$ represents a nitro, aldehyde, cyano, carboxyl or alkoxycarbonyl group or Z' represents a CHOH or C(O) group, which are then further reacted with or without isolation of these intermediates according to customary methods to give compounds of the formula (I).

The process according to the invention can be illustrated by way of example by the following reaction schemes:

Process Variant (A)

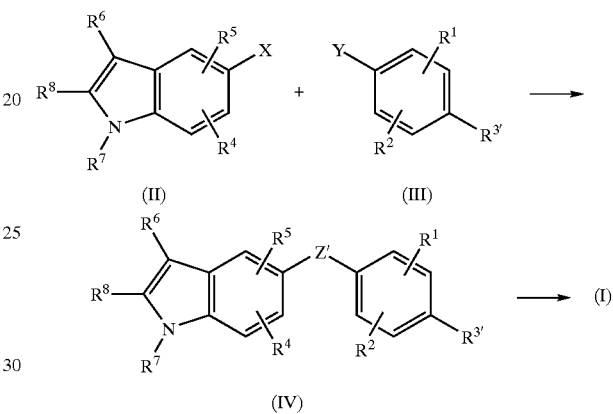

X=F, Cl, Br, I, $B(OH)_2$; Y=OH, SH, $NH_2$ or X=OH, SH, $NH_2$; Y=F, Cl, Br, I, $B(OH)_2$

Process Variant (B)

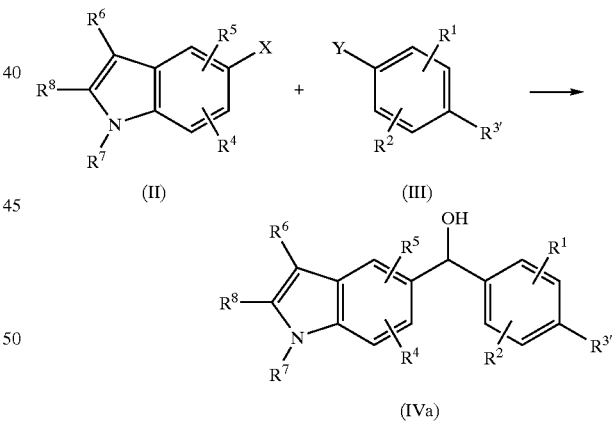

X=CHO; Y=Li, MgCl, MgBr or X=Li, MgCl, MgBr; Y=CHO

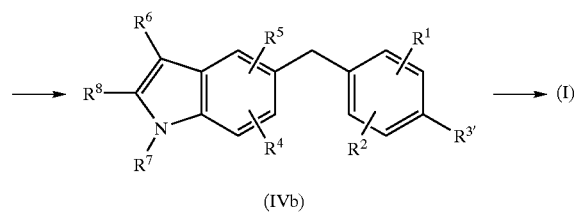

Process Variant (C)

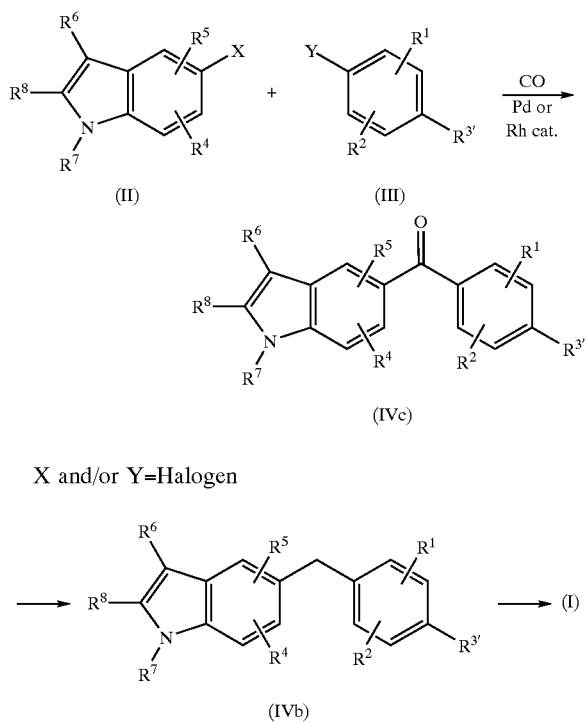

X and/or Y=Halogen

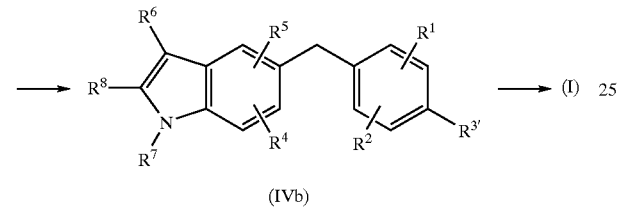

Depending on the meaning of the substituents $R^1$, $R^2$, $R^4$, $R^5$, $R^6$, $R^7$ and $R^8$, it can be useful or necessary to vary these at individual process stages within the scope of meaning indicated.

Protective groups (PG) are understood in the present application as meaning those groups in starting materials, intermediates and/or final products which protect functional groups present such as, for example, carboxyl, amino, mercapto or hydroxyl groups and which are customary in preparative organic chemistry. The groups protected in this way can then be converted into free functional groups in a simple manner under known conditions.

The compounds of the formula (I) according to the invention show a surprising and valuable pharmacological spectrum of action and can therefore be employed as versatile medicaments for the treatment of human and mammals, as for example cats and dogs. In particular, they can be employed in all indications which can be treated using natural thyroid hormones, such as by way of example and preferably, depression, goitre or cancer of the thyroid. Preferably, using the compounds of the formula (I) according to the invention, arteriosclerosis, hypercholesterolaemia, and dyslipidaemia can be treated. Moreover, adiposity and obesity and cardiac insufficiency can also be treated and a postprandial lowering of the triglycerides can be achieved.

The compounds are also suitable for the treatment of certain respiratory tract diseases, namely in particular of pulmonary emphysema and for the medicinal promotion of maturation of the lungs.

The compounds are furthermore suitable for the treatment of painful conditions and migraine, for neuronal repair (remyelinization) and also for the treatment of Alzheimer's disease.

The compounds are furthermore suitable for the treatment of osteoporosis, cardiac arrhythmias, hypothyroidism and skin diseases.

Moreover, the compounds can also be employed for promotion and regeneration of hair growth and for the treatment of diabetes.

The active compounds according to the invention open up a further treatment alternative and are an enrichment of pharmacy. In comparison to the known and previously employed thyroid hormone preparations, the compounds according to the invention show an improved spectrum of action. They are preferably distinguished by great specificity, good tolerability and lower side effects, in particular in the cardiovascular area.

The efficacy of the compounds according to the invention can be tested, for example, in vitro by the T3 promoter assay cell test described below:

The test is carried out using a stably transfected, human HepG2 hepatocarcinoma cell which expresses a luciferase gene under the control of a thyroid hormone-regulated promoter. The vector used for the transfection carries, ahead of the luciferase gene, a minimal thymidine kinase promoter having a thyroid hormone-responsive element (TRE), which consists of two inverted palindromes of 12 Bp each and an 8 Bp spacer.

For the test, the cell cultures are inoculated into 96 well plates in Eagle's Minimal Essential Medium with the following additives: glutamine, tricine [N-(tris (hydroxymethyl)methyl)glycine], sodium pyruvate, non-essential amino acids (L-Ala, L-Asn, L-Asp, L-Pro, L-Ser, L-Glu, Gly), insulin, selenium and transferrin. The cultures are grown for 48 hours at 37° C. and under a 10% $CO_2$ atmosphere. Serial dilutions of test substance or reference compound (T3, T4) and costimulator retinolic acid are then added to the test cultures and these are incubated as beforehand for a further 48 or 72 hours. Each substance concentration is tested in four replicates. For the determination of the luciferase induced by T3 or other substances, the cells are then lysed by addition of a Triton- and luciferin-containing buffer (from Promega) and immediately measured luminometrically. The $EC_{50}$ values of each compound are calculated. Representative results for the compounds according to the invention are shown in Table 5:

TABLE 5

| Example No. | $EC_{50}$ [nM] |
|---|---|
| 5 | 22 |
| 6 | 8 |
| 11 | 0.5 |
| 15 | 4 |
| 16 | 21 |

The compounds according to the invention also show surprisingly advantageous properties in the tests described below:

Test descriptions for the discovery of pharmacologically active substances:

The substances which are to be investigated for their serum cholesterol-lowering action in vivo are administered orally to male mice having a bodyweight of between 25 and 35 g. The animals are divided into groups having an identical number of animals, as a rule n=7–10, one day before the start of the experiment. During the entire experiment, drinking water and feed is available ad libitum to the animals. The substances are administered orally once daily for 7 days. For this purpose, the test substances are dissolved, for example, in a solution of Solutol HS 15+ethanol+sodium chloride solution (0.9%) in a ratio 1+1+8 or in a solution of Solutol HS 15+sodium chloride solution (0.9%) in the ratio 2+8. The dissolved substances are administered in a volume of 10 ml/kg of bodyweight using a stomach tube. As a control group, animals are used which have been treated exactly the same, but only receive the solvent (10 ml/kg of bodyweight) without test substance.

Before the first substance administration, blood is taken from each mouse for the determination of the serum cholesterol by puncture of the retroorbital venous plexus (preliminary value). The test substance is then administered to the animals for the first time using a stomach tube. 24 hours after the last substance administration (on the 8th day after the start of treatment), blood is again taken from each animal for the determination of the serum cholesterol by puncture of the retroorbital venous plexus. The blood samples are centrifuged and, after recovering the serum, the cholesterol is determined photometrically using an EPOS analyser 5050 (Eppendorf-Gerätebau, Netheler & Hinz GmbH, Hamburg). The determination is carried out using a commercially available enzyme test (Boehringer Mannheim, Mannheim).

The action of the test substances on the serum cholesterol concentration is determined by subtraction of the cholesterol value of the 1st blood sample (preliminary value) from the cholesterol value of the 2nd blood sample (after treatment). The differences of all cholesterol values of a group are averaged and compared with the average value of the differences of the control group.

Statistical analysis is carried out using Student's t test after prior checking of the variances for homogeneity.

Substances which statistically significantly ($p<0.05$) lower the serum cholesterol of the treated animals, compared with the control group, by at least 10% are regarded as pharmacologically active.

At the end of the test, the animals are weighed and sacrificed after taking blood. To check for potential cardiovascular side effects under the influence of substance, the hearts are removed and weighed. An effect on the cardiovascular system can be detected by a significant increase in the heart weight. A further parameter which can be used for the substance action is a bodyweight change.

In an analogous manner, it is possible to use, for example, NMRI mice, ob,ob mice, Wistar rats or fa,fa diabetic rats as experimental animals for this test.

A further in vivo test in which the compounds according to the invention show surprisingly advantageous properties is the cholesterol-fed rat animal model [A. Taylor et al., Molecular Pharmacology 52, 542–547 (1997); Z. Stephan et al., Atherosclerosis 126, 53–63 (1996)].

Furthermore, the cholesterol-lowering action of the compounds according to the invention can also be checked on normocholesterolaemic dogs by oral administration of the test substances for 5–7 days.

For the further investigation of potential cardiovascular side effects under the influence of substance, it is possible to use, inter alia, the determination of the expression of the mRNA of the "HCN2" ion channel ("hyperpolarization-activated cyclic nucleotide-gated channel") in mouse or rat hearts [cf also: Trost et al., Endocrinology 141 (9), 3057–3064 (2000); Gloss et al., Endocrinology 142 (2), 544–550 (2001); Pachuki et al., Circulation Research 85, 498–503 (1999)]:

HCN2 Assay

The quantification of the mRNA of the "hyperpolarization-activated cyclic nucleotide-gated" cation channel (HCN2) in rat hearts was carried out by means of real-time PCR (TaqMan-PCR; Heid et al., Genome Res. 6 (10), 986–994). For this, after preparation of the hearts the total RNA is isolated by means of RNaesy columns (from Qiagen), digested with DNase and then transcribed into cDNA (SUPERSCRIPT-II RT cDNA synthesis kit, from Gibco). The HCN2 mRNA determination is carried out on an ABI Prism 7700 apparatus (from Applied Biosystems). The sequence of the "forward" and "reverse" primer read: 5'-GGGAATCGACTCCGAGGTC-3' or 5'-GATCTTGGTGAAACGCACGA-3', that of the fluorescent probe 5'-6FAM-ACAAGACGGCCCGTGCACTACGC-TAMRA-3 (FAM= fluorescent dye 6-carboxyfluorescein; TAMRA=quencher 6-carboxytetramethylrhodamine). During the polymerase chain reaction, the Taq polymerase of the fluorescent dye FAM is removed by the 5' exonuclease activity and the previously quenched fluorescence signal is thereby obtained. The "threshold cycle" (Ct value) is distinguished as the number of cycles in which the fluorescence intensity was 10 standard deviations above the background fluorescence. The relative expression of the HCN2 mRNA calculated thereby is then standardized to the expression of the ribosomal protein L32.

In an analogous manner, this assay can also be carried out using mice hearts. The sequence of the "forward" and "reverse" primer in this case read 5'-CGAGGTGCTGGAGGAATACC-3' or 5'-CTAGCCGGTCAATAGCCACAG-3', that of the fluorescent sample 5'-6FAM-CATGATGCGGCGTGCCTTTGAG-TMARA-3.

All customary administration forms are suitable for the administration of the compounds of the general formula (I), i.e. oral, parenteral, inhalatory, nasal, sublingual, buccal, rectal or external such as, for example, transdermal, in particular preferably oral or parenteral. In the case of parenteral administration, intravenous, intramuscular or subcutaneous administration may be mentioned in particular, e.g. as a subcutaneous depot. Oral administration is very particularly preferred.

In particular, compounds of the general formulae (Ia) and (Ib) have surprisingly advantageous pharmacokinetic properties after oral administration, for example with respect to bioavailability, the active compound concentration in the blood, the half-life and/or the excretion rate.

The active compounds can be administered here on their own or in the form of preparations. For oral administration, suitable preparations are, inter alia, tablets, capsules, pellets, coated tablets, pills, granules, solid and liquid aerosols, syrups, emulsions, suspensions and solutions. The active compound must be present here in such an amount that a therapeutic action is achieved. In general, the active compound can be present in a concentration of 0.1 to 100% by weight, in particular 0.5 to 90% by weight, preferably 5 to 80% by weight. In particular, the concentration of the active compound should be 0.5–90% by weight, i.e. the active compound should be present in amounts which are sufficient to achieve the dosage range indicated.

For this purpose, the active compounds can be converted into the customary preparations in a known manner. This is carried out using inert, non-toxic, pharmaceutically suitable vehicles, excipients, solvents, vehicles, emulsifiers and/or dispersants.

Excipients which may be mentioned are, for example: water, non-toxic organic solvents such as, for example, paraffins, vegetable oils (e.g. sesame oil), alcohols (e.g. ethanol, glycerol), glycols (e.g. polyethylene glycol), solid carriers such as ground natural or synthetic minerals (e.g. talc or silicates), sugars (e.g. lactose), emulsifiers, dispersants (e.g. polyvinylpyrrolidone) and lubricants (e.g. magnesium sulphate).

In the case of oral administration, tablets can, of course, also contain additives such as sodium citrate together with additional substances such as starch, gelatin and the like. Aqueous preparations for oral administrations can furthermore be mixed with flavour enhancers or colorants.

In the case of oral administration, doses of 0.001 to 5 mg/kg, preferably 0.001 to 3 mg/kg, of bodyweight are preferably administered every 24 hours.

The new active compounds can be administered on their own and, if required, also in combination with other active compounds, preferably from the group consisting of CETP inhibitors, antidiabetics, antioxidants, cytostatics, calcium antagonists, hypotensive agents, thyroid hormones, inhibitors of HMG-CoA reductase, inhibitors of HMG-CoA reductase gene expression, squalene synthesis inhibitors, ACAT inhibitors, circulation-promoting agents, platelet aggregation inhibitors, anticoagulants, angiotensin II receptor antagonists, cholesterol absorption inhibitors, MTP inhibitors, aldose reductase inhibitors, fibrates, niacin, anorectics, lipase inhibitors and PPAR agonists.

The following working examples are intended to illustrate the invention by way of example without restrictive action on the scope of protection.

| Abbreviations used | |
|---|---|
| TLC | Thin-layer chromatography |
| DCI | Direct chemical ionization (in MS) |
| DMF | N,N-Dimethylformamide |
| DMSO | Dimethyl sulphoxide |
| EI | Electron impact ionization (in MS) |
| HPLC | High-pressure, high-performance liquid chromatography |
| conc. | concentrated |
| MS | Mass spectroscopy |
| NMP | N-Methylpyrrolidinone |
| NMR | Nuclear magnetic resonance spectroscopy |
| $R_f$ | Retention index (in TLC) |
| $R_t$ | Retention time (in HPLC) |
| THF | Tetrahydrofuran |
| aq. | aqueous |
| dec. | decomposition |

STARTING COMPOUNDS

Example I 5-(2,6-Dichloro-4-nitrophenoxy)-3-isopropyl-1H-indole

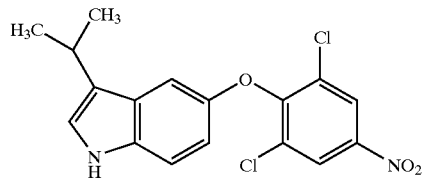

5 g of 5-hydroxy-3-isopropylindole are dissolved in 10 ml of THF and treated with 3.2 g of potassium tert-butoxide. The reaction mixture is stirred for 20 minutes at room temperature and the solvent is removed in vacuo. The phenoxide is dissolved in 10 ml of DMF and added dropwise to 6.46 g of 1,2,6-trichloro-4-nitrobenzene in 10 ml of DMF at 0° C. The reaction mixture is stirred for 30 minutes at 0° C. and slowly allowed to warm to room temperature. The reaction mixture is poured onto water, extracted with ethyl acetate, dried over sodium sulphate and the solvent is removed in vacuo. Chromatographic purification (cyclohexane/ethyl acetate) affords 663 mg of 5-(2,6-dichloro-4-nitrophenoxy)-3-isopropyl-1H-indole.

$^1$H-NMR (300 MHz, CDCl$_3$): δ=1.30, d, 6H; 3.09, sept., 1H; 6.79, dd, 1H; 6.99, m, 2H; 7.31, s, 1H; 7.89, s, broad, 1H; 8.32, s, 2H.

Example II 5-(2-chloro-6-methyl-4-nitrophenoxy)-3-isopropyl-1H-indole

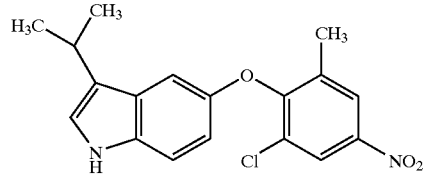

4.4 g of 5-hydroxy-3-isopropylindole are dissolved in 10 ml of THF and treated at room temperature with 2.82 g of potassium tert-butoxide. The mixture is stirred for 30 minutes at room temperature and concentrated in a rotary evaporator. The phenoxide is dissolved in DMF, treated at 0° C. with 5.17 g of 1,2-dichloro-4-nitro-5-methylbenzene and stirred for 30 minutes at 0° C. The mixture is stirred for 15 minutes at room temperature and subsequently 1 hour at 50° C. The reaction mixture is allowed to cool, poured onto water, extracted twice with ether and the combined organic phases are washed twice with water. The aqueous phases are extracted with dichloromethane, the combined organic phases are concentrated in a rotary evaporator and the residue is purified chromatographically (cyclohexane/ethyl acetate). 6.65 g of 5-(2-chloro-6-methyl-4-nitrophenoxy)-3-isopropyl-1H-indole are obtained.

$^1$H-NMR (300 MHz, CDCl$_3$): δ=1.28, d, 6H; 2.31, s, 3H; 3.07, sept., 1H; 6.75, dd 1H; 6.92, m, 1H; 6.99, m, 1H; 7.29, s, 1H; 7.87, s, broad, 1H.

Example III 3-chloro-4-[(3-isopropyl-1H-indol-5-yl)oxy]-5-methylaniline

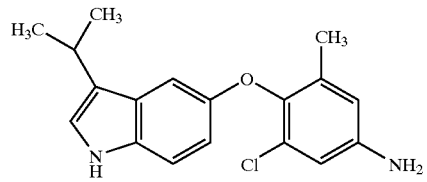

500 mg of 5-(2-chloro-6-methyl-4-nitrophenoxy)-3-isopropyl-1H-indole (Example II) are suspended in 10 ml of ethanol and hydrogenated with 50 mg of palladium on active carbon (10%) at atmospheric pressure for 2 hours. The mixture is filtered through kieselguhr, the solvent is removed in vacuo and the product is purified by chromatography (cyclohexane/ethyl acetate). 271 mg of 3-chloro-4-[(3-isopropyl-1H-indol-5-yl)oxy]-5-methylaniline are obtained.

$^1$H-NMR (300 MHz, CDCl$_3$): δ=1.29, d, 6H; 2.11, s, 3H; 3.07, sept., 1H; 3.61, s, broad, 2H; 6.50, dd, 1H; 6.66, dd, 1H; 6.78, dd, 1H; 6.94, d, 2H; 7.20, s, 1H 1H; 7.78, s, broad, 1H.

Example IV

3,5-dichloro-4-[(3-isopropyl-1H-indol-5-yl)oxy]aniline

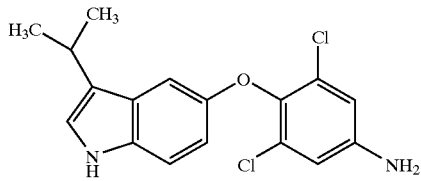

500 mg of 5-(2,6-dichloro-4-nitrophenoxy)-3-isopropyl-1H-indole (Example I) are stirred with 6.18 g of tin(II) chloride dihydrate in 5 ml of NMP for 17 hours at 50° C. The solvent is removed in vacuo and the residue is taken up in ethyl acetate. The mixture is washed with saturated ammonium chloride solution and saturated sodium chloride solution, the organic phase is dried and the solvent is removed in vacuo. The product is precipitated with diethyl ether. By chromatographic purification (cyclohexane/ethyl acetate) of the solid, 174 mg of 3,5-dichloro-4-[(3-isopropyl-1H-indol-5-yl)oxy]aniline are obtained.

$^1$H-NMR (300 MHz, DMSO-$d_6$): δ=1.21, d, 6H; 2.95, sept., 1H; 5.56, s, 2H; 6.63, dd, 1H; 6.71, s, 2H; 6.75, m, 1H; 7.06, d, 1H; 7.24, d, 1H.

Example V

4-(3-Isopropyl-1H-indol-5-yloxy)-3,5-bis-trifluoromethyl-benzaldehyde

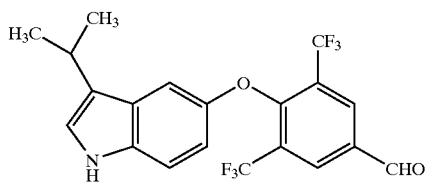

12.8 g (70.27 mmol) of 5-hydroxy-3-isopropyl-indole are dissolved in 275.8 ml of DMSO, 10.68 g (77.3 mmol) of potassium carbonate are introduced in solid form, the mixture is stirred for 10 minutes at room temperature and afterwards 19.43 g (70.27 mmol) of 3,5-bistrifluoromethyl-4-chlorobenzaldehyde are introduced in portions. After stirring at 50° C. for 3 hours the batch is poured onto a mixture of 400 ml of ethyl acetate and 250 ml of saturated ammonium chloride solution. After phase separation, the aqueous phase is extracted again with ethyl acetate, and the combined organic phases are washed twice with sodium chloride solution and dried over sodium sulphate. After removing the drying agent and distilling off the solvent the crude product is chromatographed on silica gel 60 (Merck 0.040–0.063 mm) using toluene.

| | |
|---|---|
| Yield: | 18.55 g (56.6%) |
| MS (DCI): | 450 ([M + NH$_3$ + NH$_4$]$^+$, 100%) |
| R$_f$: | 0.5 (toluene:ethyl acetate = 8:2) |
| $^1$H-NMR (300 MHz, CDCl$_3$): | δ = 1.25, d, 6H; 3.04, quin, 1H; 6.73, dd, 1H; 6.87, d, 1H; 6.96, d, 1H; 7.22, d, 1H; 7.85, broad s, 1H; 8.45, s, 2H; 10.11, s, 1H. |

Example VI

4-(3-Isopropyl-1H-indol-5-yloxy)-3,5-bis-trifluoromethyl-benzyl alcohol

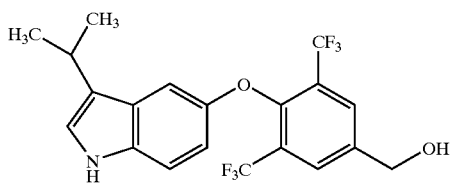

0.27 g (7.22 mmol) of sodium borohydride is added to a solution of 1.0 g (2.41 mmol) of aldehyde derivative from Example V in 20 ml of methanol in 4 portions at room temperature and the mixture is stirred for 1 hour. Afterwards the reaction solution is concentrated to one half, 60 ml of water are added and the mixture is concentrated until methanol is completely evaporated in a rotary evaporator. The aqueous phase is extracted three times with ethyl acetate, the combined organic phases are washed with sodium chloride solution, dried and concentrated, and the residue is dried in a high vacuum.

| | |
|---|---|
| Yield: | 0.996 g (96.8%) |
| MS (ESI): | 418 ([M + H]$^+$, 35%) |
| HPLC: | R$_t$ = 4.97 (97.7%) |
| | 0.5% HClO$_4$/acetonitrile |
| | Kromasil column C18 (60 × 2 mm) |
| | flow: 0.75 ml/minute; 210 nm |
| $^1$H-NMR (300 MHz, CDCl$_3$): | δ = 1.28, d, 6H; 1.96, t, 1H; 3.04, quin, 1H; 4.87, d, 2H; 6.72, dd, 1H; 6.85, d, 1H; 6.93, d, 1H; 7.2, d, 1H; 7.78, broad s, 1H; 7.94, s, 2H. |

Example VII

4-(3-Isopropyl-1H-indol-5-yloxy)-3,5-bis-trifluoromethyl-benzyl bromide

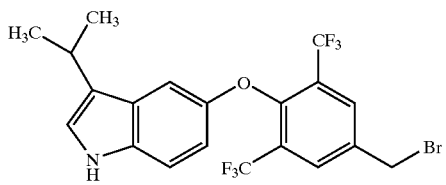

1.273 g (3.02 mmol) of triphenylphosphine dibromide are added under argon in portions at 0° C. to a solution of 0.97 g (2.32 mmol) of benzyl alcohol derivative from Example VI in 15 ml of acetonitrile and 0.3 ml (3.72 mmol) of pyridine. After 15 minutes the cooling bath is removed and the mixture is stirred for 2 hours at room temperature. The reaction solution is concentrated in vacuo, and the residue is dissolved in a little toluene and purified by chromatography on silica gel 60 by means of toluene.

| | |
|---|---|
| Yield: | 611 mg (54.7%) |
| MS (EI): | 481 ([M]$^+$, 60%) |
| HPLC: | R$_t$ = 5.30 (80.7%) |
| | 0.5% HClO$_4$/acetonitrile |
| | Kromasil column C18 (60 × 2 mm) |
| | flow: 0.75 ml/minute; 210 nm |

¹H-NMR (300 MHz, CDCl₃):  δ = 1.28, d, 6H; 3.06, quin, 1H; 4.56, s, 2H; 6.70, dd, 1H; 6.88, d, 1H; 6.95, d, 1H; 7.23, d, 1H; 7.8, broad s, 1H; 8.0, s, 2H.

Example VIII 4-(3-Isopropyl-1H-indol-5-yloxy)-3,5-bis-trifluoromethyl-phenylacetonitrile

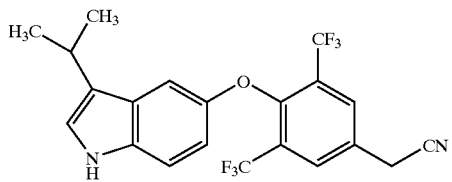

72.9 mg (1.49 mmol) of sodium cyanide are added at 50° C. to a solution of 0.57 g (1.19 mmol) of benzyl bromide from Example VII in 3.5 ml of dimethylformamide and 0.38 ml of water and the mixture is stirred for 60 minutes at 50° C. Dimethylformamide is subsequently distilled off, the concentrate is diluted with ethyl acetate and water, and the aqueous phase is separated off and extracted again with ethyl acetate. The combined organic phases are washed with sodium chloride solution, dried over sodium sulphate, filtered and concentrated. The purification of the crude product is carried out on silica gel 60 by means of toluene/ethyl acetate (toluene, toluene/ethyl acetate=18:1 and 18:1.5).

| | |
|---|---|
| Yield: | 374 mg (73.9%) |
| MS (EI): | 426 ([M]⁺, 60%) |
| R_f: | 0.51 (toluene:ethyl acetate = 9:1) |
| ¹H-NMR (300 MHz, CDCl₃): | δ = 1.28, d, 6H; 3.06, quin, 1H; 3.93, s, 2H; 6.72, dd, 1H; 6.84, d, 1H; 6.96, d, 1H; 7.23, d, 1H; 7.82, broad s, 1H; 7.9, s, 2H. |

Example IX tert-Butyl (4-hydroxy-3,5-dimethylphenoxy)acetate

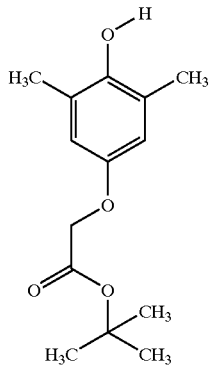

10 g of dimethylhydroquinone are dissolved in 750 ml of a mixture of 40% DMF and 60% THF and treated with 117 g of caesium carbonate. 14.1 g of tert-butyl bromoacetate are added dropwise at −25° C. and the reaction mixture is stirred for 17 hours at room temperature. After addition of 10 g of potassium carbonate the reaction mixture is stirred for 24 hours at room temperature, poured onto water and extracted twice with ethyl acetate. The combined organic phases are washed with NaCl solution, dried over sodium sulphate and the solvent is removed in vacuo. By chromatographic purification (cyclohexane/ethyl acetate) 1.27 g of tert-butyl (4-hydroxy-3,5-dimethylphenoxy)acetate are obtained.

¹H-NMR (300 MHz, CDCl₃): δ=1.42, s, 9H; 2.1 1, s, 6H; 4.47, s, 2H; 6.48, s, 2H; 7.74, s, 1H.

Example X

5-Bromo-3-isopropyl-1H-indole

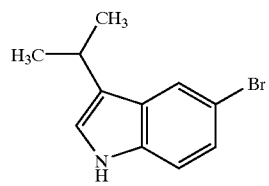

10 g of bromophenylhydrazine hydrochloride are suspended in 50 ml of acetic acid and treated dropwise at 80° C. with 3.85 g of 3-methylbutyraldehyde. The reaction mixture is stirred for 3 hours at reflux, allowed to cool and the solvent is removed in vacuo. The residue is taken up in ethyl acetate, extracted with water, the aqueous phase is extracted with ethyl acetate, the combined organic phases are washed with water and sodium carbonate solution, dried over sodium sulphate and the solvent is removed in vacuo. Chromatographic purification (cyclohexane/ethyl acetate) affords 8.6 g of 5-bromo-3-isopropyl-1H-indole.

¹H-NMR (300 MHz, CDCl₃): δ=1.35, d, 6H; 3.15, sept., 1H; 6.96, d, 1H; 7.24, m, 2H; 7.77, d, 1H; 7.89, s, broad, 1H.

Example XI

5-Bromo-1-[tert-butyl(dimethyl)silyl]-3-isopropyl-1H-indole

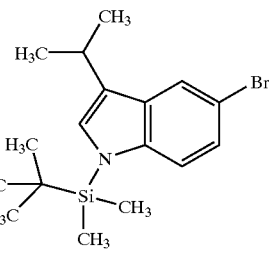

0.50 g (12.6 mmol) of 60% strength sodium hydride in paraffin oil is introduced under argon into 20 ml of THF at room temperature. A solution of 2.0 g (8.40 mmol) of 5-bromo-3-isopropyl-1H-indole (Example X) in 20 ml of THF is added dropwise and the mixture is stirred until evolution of gas can no longer be detected. 2.03 g (13.44 mmol) of tert-butyl(chloro)dimethylsilane are subsequently added dropwise. After a short reaction time a precipitate deposits. The batch is stirred for 3 h at room temperature. It is treated with 200 ml of water. The aqueous phase is extracted twice with ethyl acetate, and the combined org. phases are dried and concentrated in a rotary evaporator. The residue is chromatographed on silica gel (eluent:

cyclohexane). 2.63 g (89%) of 5-bromo-1-[tert-butyl (dimethyl)silyl]-3-isopropyl-1H-indole are obtained.

¹H-NMR (200 MHz, CDCl₃): δ=0.58, s, 6H; 0.89, s, 9H; 1.33, d, 6H; 3.12, sept., 1H; 6.88, s, 1H; 7.20, dd, 1H; 7.32, d, 1H; 7.71, d, 1H.

Example XII

1-[tert-Butyl(dimethyl)silyl]-3-isopropyl-1H-indol-5-yl-boronic acid

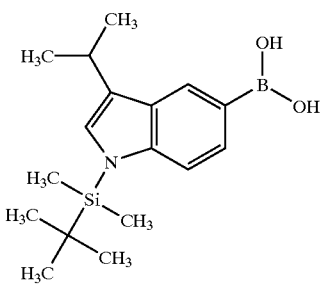

1.30 g (3.69 mmol) of 5-bromo-1[-tert-butyl(dimethyl) silyl]-3-isopropyl-1H-indole (Example XI) dissolved under argon in 10 ml of THF are introduced at −78° C. 2.50 ml (4.24 mmol) of a 1.6 N tert-butyllithium solution in n-hexane are added dropwise. The mixture is stirred for 30 min at −78° C. 1.70 ml (7.38 mmol) of triisopropyl borate are subsequently added dropwise. The batch is stirred for 2 h at −78° C.

It is subsequently treated with 4 ml of water. The aqueous phase is extracted three times with diethyl ether, and the combined org. phases are dried and concentrated in a rotary evaporator. The residue is purified chromatographically (eluent: cyclohexane, cyclohexane/ethyl acetate 5:1, 3:1). 0.68 g (58%) of 1-[tert-butyl(dimethyl)silyl]-3-isopropyl-1H-indol-5-yl-boronic acid is obtained.

¹H-NMR (200 MHz, CDCl₃): δ=0.65, s, 6H; 0.93, s, 9H; 1.48, d, 6H; 3.37, sept 1H; 6.93, s, 1H; 7.62, d, 1H; 8.08, d, 1H; 8.64, s, 1H. MS (ESI): 318 (M+H).

Example XIII tert-Butyl [4-( {1-[tert-butyl(dimethyl)silyl]-3-isopropyl-1H-indol-5-yl}oxy)-3,5-dimethylphenoxy] acetate

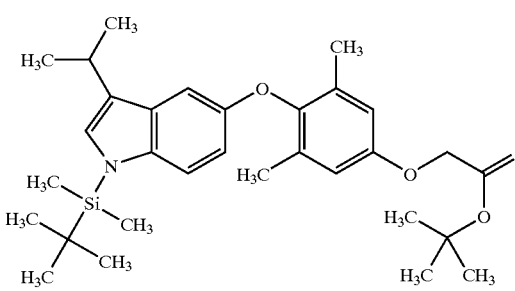

0.50 g (1.58 mmol) of 1-[tert-butyl(dimethyl)silyl]-3-isopropyl-1H-indol-5-yl-boronic acid (Example XII), 0.437 g (173 mmol) of tert-butyl-(4-hydroxy-3,5-dimethylphenoxy)acetate (Example IX), 0.286 g (1.58 mmol) of copper(II) acetate and 0.50 g of molecular sieve (4 Å, powdered) are suspended in 10 ml of dried dichloromethane. 0.64 ml (7.88 mmol) of pyridine and 1.10 ml (7.88 mmol) of triethylamine are added dropwise at room temperature. The batch is stirred overnight at room temperature. The batch is subsequently filtered through silica gel and washed with dichloromethane. The filtrate is concentrated and the residue is filtered through silica gel (dichloromethane). 0.525 g (62%) of tert-butyl-[4-({1-[tert-butyl-(dimethyl)silyl]-3-isopropyl-1H-indol-5-yl}oxy)-3,5-dimethylphenoxy]acetate is obtained.

¹H-NMR (300 MHz, CDCl₃): δ=0.54, s, 6H; 0.89, s, 9H; 1.27, d, 6H; 1.50, s, 2.12, s, 6H; 3.01, sept., 1H; 4.50, s, 2H; 6.63, s, 3H; 6.83, dd, 2H; 7.29, d, 1H.

Example XIV

3-Isopropyl-5-(4-nitro-2,6-dimethyl-phenoxy)-1H-indole

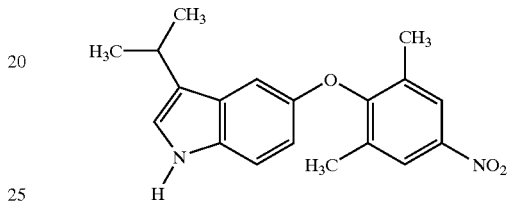

11.44 g (58.76 mmol) of 5-hydroxy-3-isopropyl-indole are dissolved in 350 ml of DMSO, 8.93 g (64.63 mmol) of potassium carbonate in solid form are introduced and subsequently 9.94 g (58.76 mmol) of 3,5-dimethyl-4-fluoronitrobenzene are added. The reaction solution is stirred for 2 hours at 100° C. under argon. Afterwards it is cooled to room temperature, 100 ml of ethyl acetate and 600 ml of H₂O are added; ethyl acetate is separated off after phase separation and the aqueous phase is reextracted twice with ethyl acetate. The combined organic phases are washed twice with sodium chloride solution, dried over sodium sulphate, filtered and concentrated to dryness. The residue is purified by chromatography on silica gel by means of cyclohexane/ethyl acetate (10:1).

| Yield: | 11.96 g (62.8%) |
|---|---|
| MS (DCI): | 342 ([M + NH₄]⁺, 100%) |
| R_f: | 0.26 (cyclohexane:ethyl acetate = 8:2) |
| ¹H-NMR (300 MHz, CDCl₃): | δ = 1.28 (d, 6H); 2.24 (s, 6H); 3.05 (quin, 1H); 6.72 (dd, 1H); 6.84 (d, 1H); 6.99 (d, 1H); 7.27 (d, 1H); 7.87 (s, 1H); 8.03 (s, 2H). |

Example XV 4-(3-Isopropyl-1H-indol-5-yloxy)-3,5-dimethyl-phenylamine

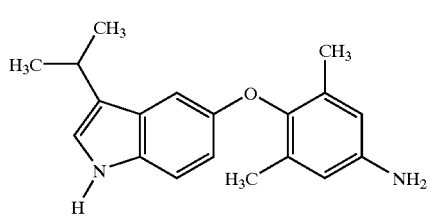

11.95 g (36.85 mmol) of nitro compound from Example XIV are hydrogenated in 500 ml of methanol/ethanol mixture using 550 mg of palladium/active carbon (10%) at 3 bar. The mixture is filtered through kieselguhr, the solvent is removed in vacuo and the product is purified by chromatography (toluene/ethyl acetate).

| Yield: | 10.75 g (97.9%) |
|---|---|
| MS (DCI): | 295 ([M + H]+, 100%) |
| $R_f$: | 0.36 (toluene:ethyl acetate = 9:1) |
| HPLC: | $R_t$= 4.15 (98.9%) |
| | 0.5% HClO$_4$/acetonitrile |
| | Kromasil column C18 (60 × 2 mm) |
| | flow: 0.75 ml/min; 210 nm |

Example XVI 4-(3-Isopropyl-1H-indol-5-yloxy)-3,5-dichlorobenzaldehyde

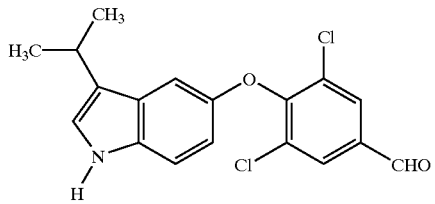

Analogously to the procedure of Example V, 10.0 g (57.07 mmol) of 5-hydroxy-3-isopropylindole are dissolved in 300 ml of DMSO, 8.68 g (62.77 mmol) of potassium carbonate are added, the mixture is stirred for 10 min at room temperature and 11.95 g (57.07 mmol) of 4,5,6-trichlorobenzaldehyde are introduced in portions, and the mixture is additionally stirred for 2 hours at room temperature and 2 hours at 50° C. After quenching with ethyl acetate/ammonium chloride solution and silica gel chromatography by means of toluene, 12,01 g (85,4%) of the desired product are obtained.

| MS (CI-POS): | 348 ([M + H]+, 100%) |
|---|---|
| $R_f$: | 0.60 (toluene:ethyl acetate = 9:1) |
| $^1$H-NMR (300 MHz, CDCl$_3$): | δ = 1.29 (d, 6H); 3.08 (quin, 1H); 6.78 (dd, 1H); 6.99 (dd, 2H); 7.27 (d, 1H); 7.85 (broad s, 1H); 7.92 (s, 2H); 9.95 (s, 1H). |

Example XVII 4-(3-Isopropyl-1H-indol-5-yloxy)-3,5-dichlorobenzyl alcohol

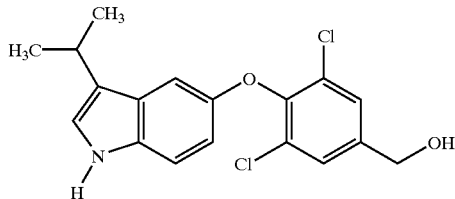

Preparation is carried out in analogy to the procedure of Example VI from 5.0 g (12.2 mmol) of aldehyde derivative from Example XVI by means of 1.39 g (36.61 mmol) of sodium borohydride.

| Yield: | 4.62 g (100%) |
|---|---|
| MS (CI-POS): | 350 ([M + H]+, 100%) |
| $R_f$: | 0.16 (toluene:ethyl acetate = 9:1) |
| $^1$H-NMR (300 MHz, CDCl$_3$): | δ = 1.29 (d, 6H); 1.83 (weak t, 1H); 3.08 (quin, 1H); 4.71 (d, 2H); 6.8 (dd, 1H); 6.95 (d, 1H); 6.99 (d, 1H); 7.23 (d, 1H); 7.42 (s, 2H); 7.82 (broad s, 1H). |

Example XVIII 4-(3-Isopropyl-1H-indol-5-yloxy)-3,5-dichlorobenzyl bromide

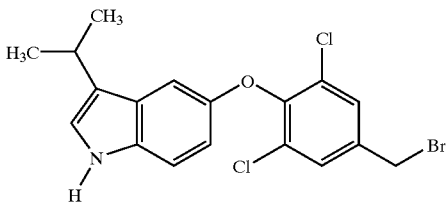

Analogously to the procedure of Example VII, 4.8 g (12.66 mmol) of benzyl alcohol derivative from Example XVII are reacted with 6.95 g (16.46 mmol) of dibromotriphenylphosphorane and 1.6 g (20.26 mmol) of pyridine in 80 ml of acetonitrile.

| Yield: | 2.03 g (35.5%) |
|---|---|
| MS (CI-POS): | 413 ([M + H]+, 57%) |
| HPLC: | $R_t$ = 5.62 (91.4%) |
| | 0.5% HClO$_4$/acetonitrile |
| | Kromasil column C18 (60 × 2 mm) |
| | flow: 0.75 ml/min; 210 nm |
| $^1$H-NMR (300 MHz, CDCl$_3$): | δ = 1.3 (d, 6H); 3.1 (quin, 1H); 4.43 (s, 2H); 6.77 (dd, 1H); 6.97 (s, 1H); 7.02 (d, 1H); 7.24 (d, 1H); 7.43 (s, 2H); 7.82 (broad s, 1H). |

Example XIX 4-(3-Isopropyl-1H-indol-5-yloxy)-3,5-dichlorophenylacetonitrile

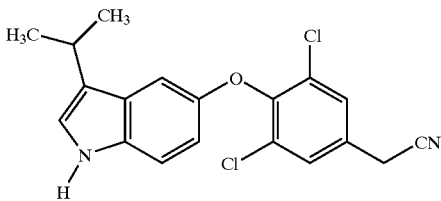

Analogously to the procedure of Example VIII, 1.0 g (2.42 mmol) of benzyl bromide from Example XVIII is reacted with 0.15 g (3.03 mmol) of sodium cyanide in DMF/H$_2$O (10:1) at 50° C. in 60 min. After isolation of the crude product (distilling off DMF and quenching with ethyl acetate/water), chromatography is carried out on silica gel 60 by means of toluene.

Yield: 0.763 g (65.4%)
MS (DCI): 359 ([M + H]⁺, 67%)
R_f: 0.47 (toluene:ethyl acetate = 9:1)
¹H-NMR (300 MHz, CDCl₃): δ =1.3 (d, 6H); 3.09 (quin, 1H); 3.78 (s, 2H); 6.78 (dd, 1H); 6.97 (d, 2H); 7.25 (d, 1H); 7.4 (s, 2H); 7.85 (broad s, 1H).

Example XX

4-(3-Cyclohexylmethyl-1H-indol-5-yloxy)-3,5-bis-trifluoromethyl-benzaldehyde

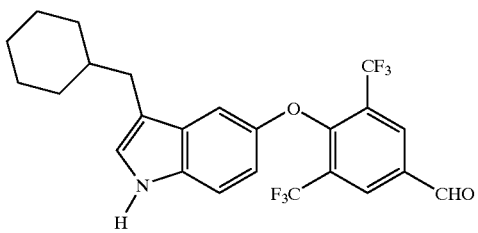

Analogously to the procedure of Example V, 2.0 g (8.72 mmol) of 5-hydroxy-3-cyclohexylmethyl-indole are dissolved in 50 ml of DMSO, 1.33 g (9.59 mmol) of potassium carbonate are added, the mixture is stirred for 10 min at room temperature and afterwards 2.41 g (8.72 mmol) of 3,5-bis-trifluoromethyl-4-chlorobenzaldehyde are introduced in portions. After stirring overnight at 50° C., the batch is worked up analogously to Example V and the crude product is chromatographed on silica gel 60 by means of toluene.

Yield: 2.23 g (49.8%)
MS (DCI): 504 ([M + NH₃ + NH₄]⁺, 100%)
R_f: 0.57 (toluene:ethyl acetate = 9:1)
¹H-NMR (300 MHz, CDCl₃): δ = 0.91 (m, 2H); 1.15 (m, 4H); 1.5 (m, 1H); 1.66 (m, 4H); 2.5 (d, 2H); 6.71 (dd, 1H); 6.82 (d, 1H); 6.97 (d, 1H); 7.22 (d, 1H); 7.89 (broad s, 1H); 8.46 (s, 2H); 10.11 (s, 1H).

Example XXI

4-(3-Cyclohexylmethyl-1H-indol-5-yloxy)-3,5-bis-trifluoromethyl-benzyl alcohol

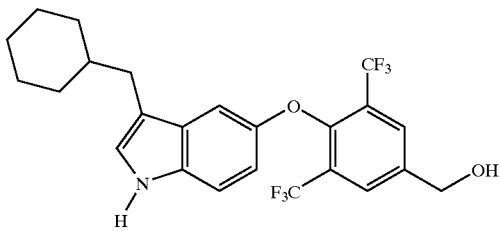

Preparation is carried out in analogy to the procedure of Example VI from 2.20 g (4.29 mmol) of aldehyde derivative from Example XX with 0.49 g (12.86 mmol) of sodium borohydride.

Yield: 2.05 g (100%)
MS (ESI): 4.72 ([M + H]⁺, 100%)
HPLC: R_t = 5.34 (98.4%)
0.5% HClO₄/acetonitrile
Kromasil column C18 (60 × 2 mm)
flow: 0.75 ml/min; 210 nm
¹H-NMR (200 MHz, CDCl₃): δ = 0.9 (m, 2H); 1.13 (m, 4H); 1.5 (m, 1H); 1.63 (m, 4H); 1.95 (t, 1H); 2.5 (d, 2H); 4.88 (d, 2H); 6.7 (dd, 1H); 6.81 (d, 1H); 6.93 (d, 1H); 7.2 (d, 1H); 7.83 (broad s, 1H); 7.94 (s, 2H).

Example XXII

4-(3-Cyclohexylmethyl-1H-indol-5-yloxy)-3,5-bis-trifluoromethyl-benzyl bromide

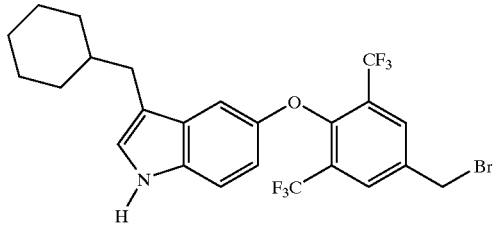

Preparation is carried out in analogy to the procedure of Example VII from 2.0 g (4.18 mmol) of benzyl alcohol derivative from Example XXI and 2.82 g (6.69 mmol) of dibromotriphenylphosphorane in 40 ml of acetonitrile. After stirring for 3 hours at room temperature, 0.3 equivalent of dibromotriphenylphosphorane is again added. The mixture is additionally stirred for 5 hours at 70° C. and afterwards overnight at room temperature. The purification of the product is carried out on silica gel using toluene as eluent.

Yield: 0.96 g (40.2%)
MS (ESI): 534 ([M + H]⁺, 100%)
R_f: 0.76 (toluene:ethyl acetate = 9:1)
¹H-NMR (200 MHz, CDCl₃): δ = 0.92 (m, 2H); 1.16 (m, 4H); 1.5 (m, 1H); 1.66 (m, 4H); 2.5 (d, 2H); 4.58 (s, 2H); 6.69 (dd, 1H); 6.83 (d, 1H); 6.95 (d, 1H); 7.21 (d, 1H); 7.35 (broad s, 1H); 7.95 (s, 2H).

Example XXIII

4-(3-cyclohexylmethyl-1H-indol-5-yloxy)-3,5-bis-trifluoromethyl-phenylacetonitrile

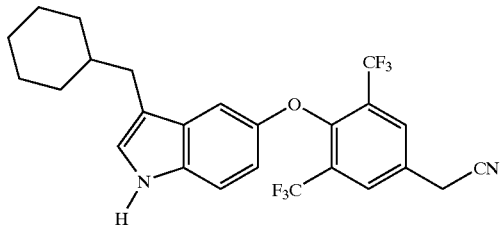

Preparation is carried out in analogy to the procedure of Example VIII from 0.85 g (1.59 mmol) of benzyl bromide from Example XXII with 0.1 g (1.99 mmol) of sodium cyanide in 5 ml of dimethylformamide and 0.5 ml of water at 50° C. in 1.5 hours. The chromatography of the crude product is carried out on silica gel 60 by means of toluene.

| | |
|---|---|
| Yield: | 0.32 g (37.7%) |
| MS (ESI): | 481 ([M + H]+, 100%) |
| HPLC: | $R_t$ = 5.67 (90.0%) |
| | 0.5% $HClO_4$/acetonitrile |
| | Kromasil column C18 (60 × 2 mm) |
| | flow: 0.75 ml/min; 210 nm |
| 1H-NMR (300 MHz, $CDCl_3$): | δ = 0.92 (m, 2H); 1.16 (m, 4H); 1.5 (m, 1H); 1.67 (m, 4H); 2.5 (d, 2H); 3.92 (s, 2H); 6.69 (dd, 1H); 6.8 (d, 1H); 6.95 (d, 1H); 7.22 (d, 1H); 7.84 (broad s, 1H); 7.91 (s, 2H). |

PREPARATION EXAMPLES

Example 1

Methyl 3-({4-[(3-isopropyl-1H-indol-5-yl)oxy]-3,5-dimethylphenyl}amino)-3-oxopropanoate

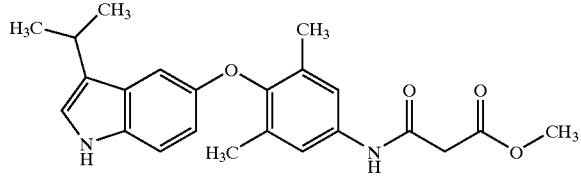

0.2 g (0.68 mmol) of 4-[(3-isopropyl-1H-indol-5-yl)oxy]-3,5-dimethylaniline (Example XV) are introduced into 2 ml of acetone with 76 mg (0.75 mmol) of triethylamine and the mixture is treated at 0° C. with 102 mg (0.75 mmol) of methyl malonyl chloride. It is stirred for 1 h, diluted with dichloromethane and extracted with sodium chloride solution and with $NaHCO_3$ solution. The organic phase is dried and the solvent is removed in vacuo. 211 mg (74%) of methyl 3-({4-[(3-isopropyl-1H-indol-5-yl)oxy]-3,5-dimethylphenyl}amino)-3-oxo-propanoate are obtained.

¹H-NMR (300 MHz, $CDCl_3$): δ=1.29, d, 6H; 2.16, s, 6H; 3.05, hept., 1H; 3.50, s, 2H; 3.81, s, 3H; 6.72, dd, 1H; 6.88, d, 1H; 6.95, d, 1H; 7.25, m, 1H; 7.30 s, 2H; 7.77, s, broad, 1H.

Example 2

3-({4-[(3-Isopropyl-1H-indol-5-yl)oxy]-3,5-dimethylphenyl}amino)-3-oxopropanoic acid

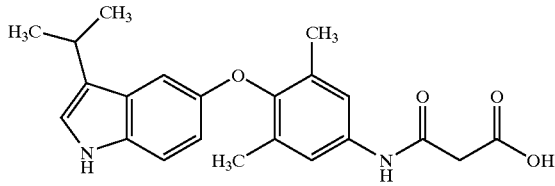

50 mg of methyl 3-({4-[(3-isopropyl-1H-indol-5-yl)oxy]-3,5-dimethyl-phenyl}-amino)-3-oxo-propanoate (Example 1) are stirred in 2 ml of ethanol with 30 mg of sodium hydroxide for 30 minutes. The solvent is removed in vacuo. The mixture is taken up in ether/water, the organic phase is dried and the solvent is removed in vacuo. 23 mg (46%) of 3-({4-[(3-isopropyl-1H-indol-5-yl)oxy]-3,5-dimethylphenyl}amino)-3-oxopropanoic acid are obtained.

1H-NMR (300 MHz, DMSO-$d_6$): δ=1.18, d, 6H; 2.02, s, 6H; 2.92, hept., 1H; 6.52, dd, 1H; 6.64, d, 1H; 7.02, s, 2H; 7.18, d, 1H; 7.32, s, 2H.

Example 3

Ethyl N-{4-[(3-isopropyl-1H-indol-5-yl)oxy]-3,5-dimethylphenyl}glycinate

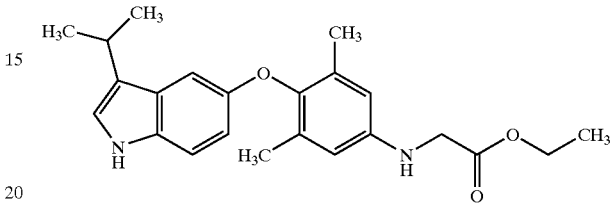

210 mg of 4-[(3-isopropyl-1H-indol-5-yl)oxy]-3,5-dimethylaniline (Example XV) are brought under reflux with 119 mg of ethyl bromoacetate and 117 mg of sodium acetate in 10 ml of ethanol for 24 h. After addition of water, the mixture is extracted with ether, and the organic phase is dried and concentrated in a rotary evaporator. By chromatographic purification (cyclohexane/ethyl acetate), 143 mg (53%) of ethyl N-{4-[(3-isopropyl-1H-indol-5-yl)oxy]-3,5-dimethylphenyl} glycinate are obtained.

¹H-NMR (300 MHz, $CDCl_3$): δ=1.27, d, 6H; 1.31, t, 3H; 2.09, s, 6H; 3.06, hept 1H; 3.92, s, 2H; 4.12, s, broad, 1H; 4.26, quart., 2H; 6.38, s, 2H; 6.72, dd, 1H; 6.91, dd, 2H; 7.20, d, 1H; 7.77, s, broad, 1H.

Example 4a

Methyl 3-({3-chloro-4-[(3-isopropyl-1H-indol-5-yl)oxy]-5-methylphenyl}amino)-3-oxo-propanoate

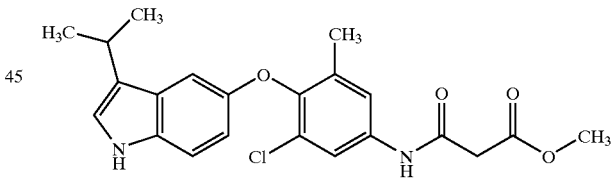

131 mg of 3-chloro-4-[(3-isopropyl-1H-indol-5-yl)oxy]-5-methylaniline (Example III) are dissolved in 3 ml of acetone with 46 mg of triethylamine and treated dropwise with 62 mg of methyl malonyl chloride at 0° C. The reaction mixture is stirred for 3 hours at room temperature, poured onto 20 ml of dichloromethane, and the organic phase is washed with sodium chloride solution, dried over sodium sulphate and concentrated in a rotary evaporator. By chromatographic purification (cyclohexane/ethyl acetate), 134 mg of methyl 3-({3-chloro-4-[(3-isopropyl-1Hindol-5-yl)oxy]-5-methylphenyl}amino)-3-oxo-propanoate are obtained.

¹H-NMR (300 MHz, $CDCl_3$): δ=1.28, d, 6H; 2.20, s, 3H; 3.07, sept., 1H; 3.50, s, 2H; 3.83, s, 3H; 6.77, dd, 1H; 6.92, d, 1H; 6.95, d, 1H; 7.24, m, 1H; 7.36, d, 1H; 7.65, d, 1H; 7.81, s, broad, 1H; 9.24, s, broad, 1H.

Example 4b

Ethyl 3-({3-chloro-4-[(3-isopropyl-1H-indol-5-yl)oxy]-5-methylphenyl}amino)-3-oxo-propanoate

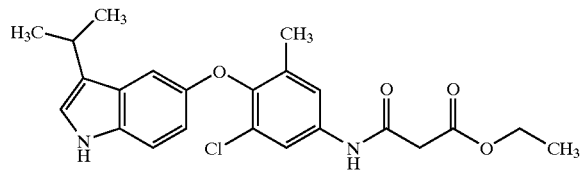

In analogy to Example 4a, starting from 2.50 g (7.94 mmol) of 3-chloro-4-[(3-isopropyl-1H-indol-5-yl)oxy]-5-methylaniline (Example III) and 1.26 g (7.94 mmol) of ethyl malonyl chloride, 3.65 g (99% of theory) of ethyl 3-({3-chloro-4-[(3-iso-propyl-1H-indol-5-yl)oxy]-5-methylphenyl}amino)-3-oxo-propanoate are obtained.

$^1$H-NMR (200 MHz, CDCl$_3$): δ=1.28, d, 6H; 1.34, t, 3H; 2.19, s, 3H; 3.08, sept., 1H; 3.49, s, 2H; 4.27, quart., 2H; 6.76, dd, 1H; 6.93, m, 2H; 7.22, m, 1H; 7.36, d, 1H; 7.66, d, 1H; 7.80, broad s, 1H; 9.32, broad s, 1H.

Example 4c

Isopropyl 3-({3-chloro-4-[(3-isopropyl-1H-indol-5-yl)oxy]-5-methylphenyl}-amino)-3-oxo-propanoate

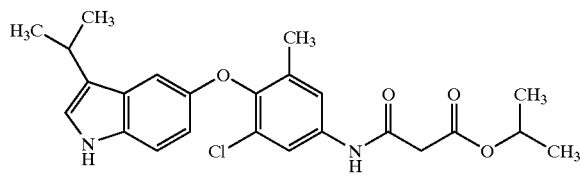

This compound can be prepared starting from 3-chloro-4-[(3-isopropyl-1H-indol-5-yl)oxy]-5-methylaniline (Example III) in analogy to Example 4a.

Example 4d

2-Hydroxyethyl 3-({3-chloro-4-[(3-isopropyl-1H-indol-5-yl)oxy]-5-methylphenyl}-amino)-3-oxopropanoate

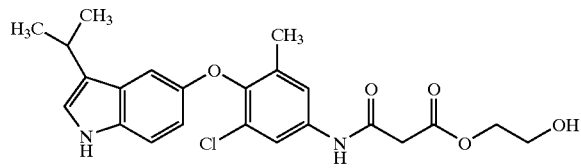

This compound can be prepared starting from 3-chloro-4-[(3-isopropyl-1H-indol-5-yl)oxy]-5-methylaniline (Example III) or methyl 3-({3-chloro-4-[(3-isopropyl-1H-indol-5-yl)oxy]-5-methylphenyl}amino)-3-oxo-propanoate (Example 4a) according to methods known from the literature.

Example 5

N-{4-[(3-Isopropyl-1H-indol-5-yl)oxy]-3,5-dimethylphenyl}glycine

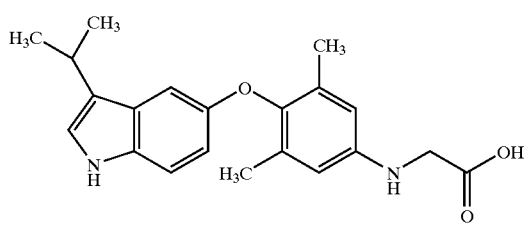

56 mg of ethyl N-{4-[(3-isopropyl-1H-indol-5-yl)oxy]-3,5-dimethylphenyl}glycinate (Example 3) are stirred in 7 ml of dioxane with 1.5 ml of 1N sodium hydroxide for 2 hours at room temperature. The mixture is poured onto water, rendered acidic using 1N hydrochloric acid, extracted with ethyl acetate, the extract is dried and the solvent is removed in vacuo. 51 mg of N-{4-[(3-isopropyl-1H-indol-5-yl)oxy]-3,5-dimethyl-phenyl}glycine are obtained $^1$H-NMR (300 MHz, CDCl$_3$): δ=1.29, d, 6H; 2.10, s, 6H; 3.07, sept., 1H; 3.70, s, 2H; 6.41, s, 2H; 6.73, m, 1H; 6.91, m, 2H; 7.21, d, 1H; 7.77, s, broad, 1H.

Example 6

3-({3-Chloro-4-[(3-isopropyl-1H-indol-5-yl)oxy]-5-methylphenyl}amino)-3-oxo-propionic acid

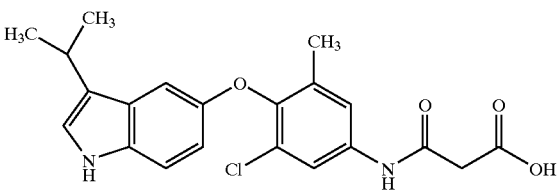

101 mg of methyl 3-({3-chloro-4-[(3-isopropyl-1H-indol-5-yl)oxy]-5-methyl-phenyl}amino)-3-oxo-propanoate (Example 4a) are dissolved in 2 ml of ethanol and 1 ml of 1N sodium hydroxide solution, the solution is stirred at room temperature for 1 hour and the solvent is removed in vacuo. The residue is rendered acidic, extracted with ethyl acetate, the extract is dried over sodium sulphate and the solvent is removed in vacuo. 87 mg of 3-({3-chloro-4-[(3-isopropyl-1H-indol-5-yl)oxy]-5-methylphenyl}amino)-3-oxopropionic acid are obtained.

$^1$H-NMR (300 MHz, MeOH-d$_4$): δ=1.25, d, 6H; 2.16, s, 3H; 2.99, sept., 1H; 3.45, s, 2H; 6.69, dd, 1H; 6.76, d, 1H; 6.96, s, 1H; 7.23, d, 1H; 7.38, d, 1H; 7.73, d, 1H,

Example 6a

Potassium 3-({3-chloro-4-[(3-isopropyl-1H-indol-5-yl)oxy]-5-methylphenyl}amino)-3-oxopropanoate

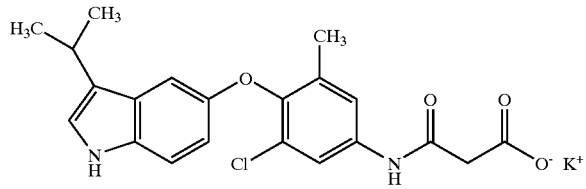

1.16 g (2.89 mmol) of 3-({3-chloro-4-[(3-isopropyl-1H-indol-5-yl)oxy]-5-methyl-phenyl}amino)-3-oxopropionic acid (Example 6) are dissolved in 15 ml of THF and treated dropwise at 0° C. with 5.67 ml of a 0.51 molar potassium hydroxide solution. The reaction mixture is stirred for one hour and the solvent is then removed in vacuo. By co-evaporation with toluene, 1.25 g (99% of theory) of potassium 3-({3-chloro-4-[(3-isopropyl-1H-indol-5-yl)oxy]-5-methylphenyl}-amino)-3-oxopropanoate are obtained $^1$H-NMR (200 MHz, DMSO-$d_6$): δ=1.20, d, 6H; 2.10, s, 3H; 2.83, s, 2H; 2.96, sept., 1H; 6.62, dd, 1H; 6.73, d, 1H; 7.04, d, 1H; 7.26, m, 3H; 7.84, d, 1H; 10.70, s, broad 1H; 13.03, s, broad, 1H.

Example 6b

Sodium 3-({3-chloro-4-[(3-isopropyl-1H-indol-5-yl)oxy]-5-methylphenyl}amino)-3-oxopropanoate

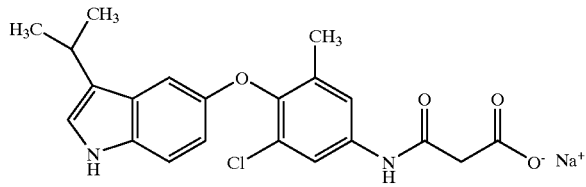

This compound is obtained in a manner analogous to Example 6a starting from 3-({3-chloro-4-[(3-isopropyl-1H-indol-5-yl)oxy]-5-methylphenyl}amino)-3-oxo-propionic acid (Example 6) and sodium hydroxide.

Example 6c

Magnesium bis[3-({3-chloro-4-[(3-isopropyl-1H-indol-5-yl)oxy]-5-methylphenyl}-amino)-3-oxopropanoate]

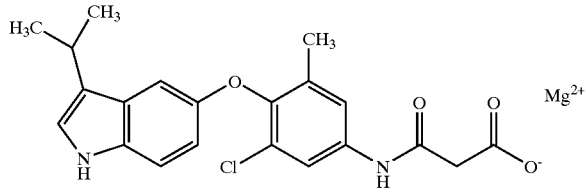

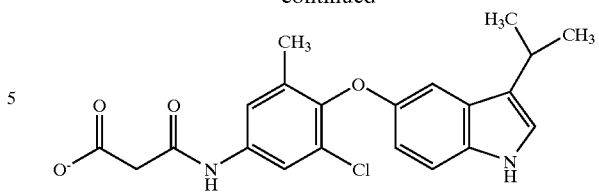

This compound is obtained in a manner analogous to Example 6a starting from 3-({3-chloro-4-[(3-isopropyl-1H-indol-5-yl)oxy]-5-methylphenyl}amino)-3-oxo-propionic acid (Example 6) and magnesium methoxide.

Example 6d

Calcium bis[3-({3-chloro-4-[(3-isopropyl-1H-indol-5-yl)oxy]-5-methylphenyl}-amino)-3-oxopropanoate]

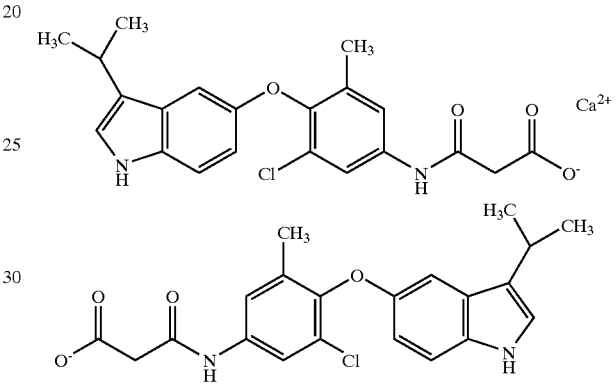

This compound is obtained in a manner analogous to Example 6a starting from 3-({3-chloro-4-[(3-isopropyl-1H-indol-5-yl)oxy]-5-methylphenyl}amino)-3-oxo-propionic acid (Example 6) and calcium hydroxide.

Example 7

Methyl 3-({3,5-dichloro-4-[(3-isopropyl-1H-indol-5-yl)oxy]phenyl}amino)-3-oxo-propanoate

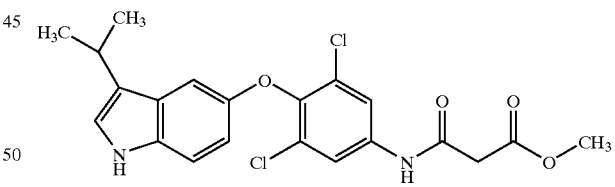

139 mg of 3,5-dichloro-4-[(3-isopropyl-1H-indol-5-yl)oxy]aniline (Example IV) are dissolved with 46 mg of triethylamine in 3 ml of acetone and treated dropwise at 0° C. with 62 mg of methyl malonyl chloride. The reaction mixture is stirred at room temperature for one hour, poured onto 20 ml of dichloromethane, and the organic phase is washed with sodium chloride solution, dried over sodium sulphate and concentrated in a rotary evaporator. By chromatographic purification (cyclohexane/-ethyl acetate), 162 mg of methyl 3-({3,5-dichloro-4-[(3-isopropyl-1H-indol-5-yl)-oxy]phenyl}amino)-3-oxopropanoate are obtained $^1$H-NMR (300 MHz, CDCl$_3$): δ=1.29, d, 6H; 3.09, sept., 1H; 3.47, s, 2H; 3.82, s, 3H; 6.80, dd, 1H; 6.96, m, 1H; 7.19, s, 1H; 7.24, m, 1H; 7.70, s, 2H; 7.82, s, broad 1H; 9.43, s, broad, 1H.

Example 8

3-({3,5-Dichloro-4-[(3-isopropyl-1H-indol-5-yl)oxy]phenyl}amino)-3-oxopropionic acid

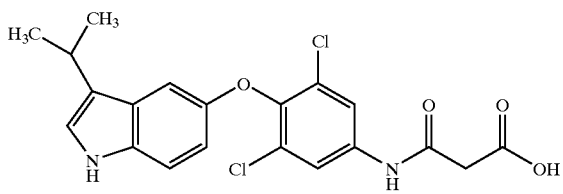

193 mg of methyl 3-({3,5-dichloro-4-[(3-isopropyl-1H-indol-5-yl)oxy]phenyl}-amino)-3-oxopropanoate (Example 7) are stirred in 3 ml of ethanol with 1 ml of 1N NaOH for one hour at room temperature. The solvent is removed in vacuo and the residue is taken up in dichloromethane. The mixture is shaken with water, the organic phase is dried and the solvent is removed in vacuo. By stirring with diethyl ether, 143 mg of 3-({3,5-dichloro-4-[(3-isopropyl-1H-indol-5-yl)oxy]phenyl}amino)-3-oxopropionic acid are obtained.

$^1$H-NMR (300 MHz, MeOH-$d_4$): δ=1.27, d, 6H; 3.00, sept., 1H; 3.35, s, 2H; 6.70, dd, 1H; 6.79, m, 1H; 6.97, s, 1H; 7.23, d, 1H; 7.79, s, 2H.

Example 9

Ethyl N-{3-chloro-4-[(3-isopropyl-1H-indol-5-yl)oxy]-5-methylphenyl}glycinate

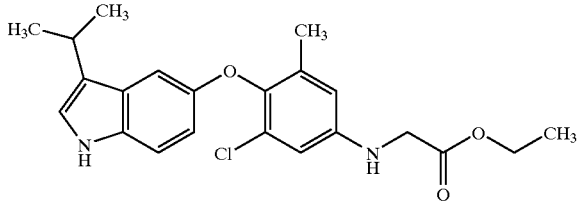

120 mg of 3-chloro-4-[(3-isopropyl-1H-indol-5-yl)oxy]-5-methylaniline (Example III) are heated to reflux with 62 mg of sodium acetate and 63 mg of ethyl bromoacetate in 5 ml of ethanol for 17 hours. A further 21 mg of ethyl bromoacetate are added and the mixture is refluxed for 3 hours. The solvent is removed in vacuo, the residue is taken up with water and dichloromethane, the organic phase is washed with saturated sodium chloride solution, dried and the solvent is removed in vacuo. Chromatographic purification (cyclohexane/ethyl acetate) affords 56 mg of ethyl N-{3-chloro-4-[(3-isopropyl-1H-indol-5-yl)oxy]-5-methylphenyl}glycinate.

$^1$H-NMR (300 MHz, CDCl$_3$): δ=1.29, d, 6H; 1.32, t, 3H; 2.13, s, 3H; 3.08, sept., 1H; 3.91, s, 2H; 4.28, quart, 2H; 6.43, d, 1H; 6.56, d, 1H; 6.77, dd, 1H; 6.94, d, 1H; 7.22, d, 1H; 7.78, s, broad, 1H.

Example 10

Ethyl N-{3,5-dichloro-4-[(3-isopropyl-1H-indol-5-yl)oxy]phenyl}glycinate

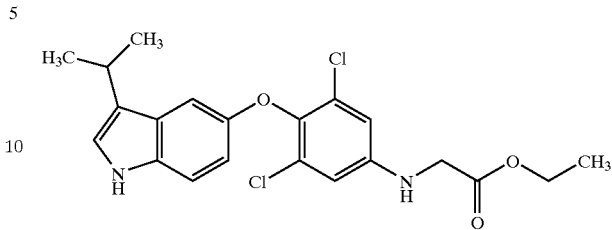

100 mg of 3,5-dichloro-4-[(3-isopropyl-1H-indol-5-yl)oxy]aniline (Example IV) are heated to reflux with 49 mg of sodium acetate and 50 mg of ethyl bromoacetate in 5 ml of ethanol for 17 hours. A further 21 mg of ethyl bromoacetate are added and the mixture is refluxed for 2 hours. The solvent is removed in vacuo, the residue is taken up with water and dichloromethane, the organic phase is washed with saturated sodium chloride solution, dried and the solvent is removed in vacuo. Chromatographic purification (cyclohexane/ethyl acetate) affords 22 mg of ethyl N-{3,5-dichloro-4-[(3-isopropyl-1H-indol-5-yl)oxy]phenyl}glycinate.

$^1$H-NMR (300 MHz, DMSO-$d_6$): δ=1.21, t, 3H; 1.22, d, 6H; 2.96, m 1H; 4.00, m, 2H; 4.15, quart., 2H; 6.63, m, 1H; 6.76, d, 1H; 6.77, s, 2H; 7.06, d, 1H; 7.24, d, 1H.

Example 11

4-(3-Isopropyl-1H-indol-5-yloxy)-3,5-bis-trifluoromethylphenylacetic acid

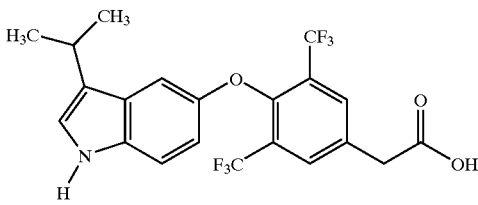

A mixture of 5 ml of concentrated sulphuric acid and 5 ml of water is added dropwise to a solution of 0.35 g (0.82 mmol) of nitrile derivative from Example VIII in 5 ml of acetic acid (100% strength). The reaction solution is stirred at 105° C. for 4 hours, then cooled to room temperature and treated with ice-cold water and ethyl acetate. The organic phase is separated off, the aqueous solution is extracted again with ethyl acetate, and the combined organic phases are dried over sodium sulphate, filtered and concentrated to give an oil. The crude product (120.3 mg) is chromatographed on silica gel 60 by means of methylene chloride/methanol (95:5 and 95:11).

| | |
|---|---|
| Yield: | 55 mg (15.3%) |
| MS (DCI): | 446 ([M + H]$^+$, 100%) |
| R$_f$ : | 0.38 (methylene chloride:methanol = 9:1) |
| $^1$H-NMR (300 MHz, CDCl$_3$): | δ = 1.28, d, 6H; 3.05, quin, 1H; 3.81, s, 2H; 6.69, dd, 1H; 6.89, d, 1H; 6.94, d, 1H; 7.21, d, 1H; 7.8, broad s, 1H; 7.88, s, 2H. |

Example 12

4-(3-Isopropyl-1H-indol-5-yloxy)-3,5-bis-trifluoromethyl-benzyltetrazole

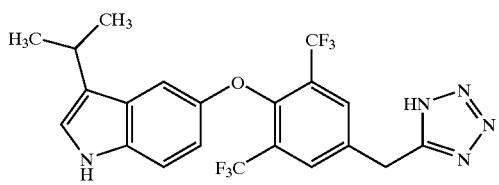

251 mg (4.69 mmol) of ammonium chloride and 305 mg (4.69 mmol) of sodium azide are added to a solution of 200 mg (0.469 mmol) of nitrile derivative from Example VIII in 8 ml of dimethylformamide and the solution is boiled under reflux for 4 hours. The solution is then highly concentrated, treated with 6N hydrochloric acid and extracted three times with ethyl acetate. The combined organic phases are dried, filtered and concentrated to an oil in vacuo. The crude product is dissolved in dichloromethane and chromatographed on silica gel 60 using dichloromethane with addition of methanol in the gradient mode (90:5 to 90:40).

| | |
|---|---|
| Yield: | 126 mg (57.3%) |
| MS (ESI): | 470 ([M + H]$^+$, 100%) |
| $R_f$: | 0.30 (dichloromethane:methanol = 9:1) |
| $^1$H-NMR (200 MHz, CDCl$_3$): | δ = 1.27, d, 6H; 3.06, quin, 1H; 4.49, s, 2H; 6.67, dd, 1H; 6.88, d, 1H; 6.94, d, 1H; 7.2, d, 1H; 7.84, broad s, 1H; 7.92, s, 2H; 8.01, s, 1H. |

Example 13

Ethyl 4-(3-isopropyl-1H-indol-5-yloxy)-3,5-bis-trifluoromethyl-cinnamate

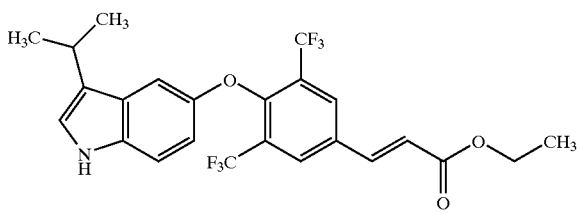

1.0 g (2.41 mmol) of aldehyde derivative from Example V is dissolved in 10 ml of toluene and 0.92 g (2.65 mmol) of ethoxycarbonylmethylene-triphenylphosphorane is introduced in portions. After stirring at room temperature for 2 days, the reaction mixture is concentrated to a half of the volume and chromatographed on silica gel 60 by means of toluene.

| | |
|---|---|
| Yield: | 1.076 g (88.4%) |
| MS (ESI): | 486 ([M + H]$^+$, 100%) |
| $R_f$: | 0.68 (toluene:ethyl acetate = 8:2) |
| HPLC: | $R_t$ = 5.44 (94.5%) |
| | 0.5% HClO$_4$/acetonitrile |
| | Kromasil column C18 (60 × 2 mm) |
| | flow: 0.75 ml/minute; 210 nm |
| $^1$H-NMR (200 MHz, CDCl$_3$): | δ = 1.27, d, 6H; 1.37, t, 3H; 3.05, quin, 1H; 4.3, quart, 2H; 6.55, broad d, 1H; 6.72, dd, 1H; 6.87, d, 1H; 6.95, d, 1H; 7.21, d, 1H; 7.73, broad d, 1H; 7.84, broad s, 1H; 8.04, s, 2H. |

Example 14

4-(3-Isopropyl-1H-indol-5-yloxy)-3,5-bis-trifluoromethyl-cinnamic acid

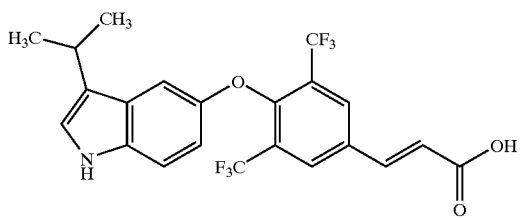

0.23 g (0.46 mmol) of ethyl cinnamate derivative from Example 13 are dissolved in 10 ml of dioxane, 4 ml of 1 molar sodium hydroxide solution are added and the mixture is stirred for 5 hours at room temperature. The reaction solution is acidified to pH 4 using 1N hydrochloric acid, treated with ethyl acetate and the aqueous phase is extracted a further two times with ethyl acetate. The combined organic phases are washed with sodium chloride solution, dried over sodium sulphate, filtered, concentrated and dried overnight in a high vacuum.

| | |
|---|---|
| Yield: | 0.175 g (79.0%) |
| MS (DCI): | 475 ([M + NH$_4$]$^+$, 100%) |
| HPLC: | $R_t$ = 4.99 (96.3%) |
| | 0.5% HClO$_4$/acetonitrile |
| | Kromasil column C18 (60 × 2 mm) |
| | flow: 0.75 ml/minute; 210 nm |
| $^1$H-NMR (200 MHz, CDCl$_3$): | δ = 1.28, d, 6H; 3.06, quin, 1H; 6.59, broad d, 1H; 6.73, dd, 1H; 6.88, d, 1H; 6.97, d, 1H; 7.23, d, 1H; 7.83, broad s and broad d, 2H; 8.09, s, 2H. |

Example 15

4-(3-Isopropyl-1H-indol-5-yloxy)-3,5-bis-trifluoromethylphenylpropionic acid

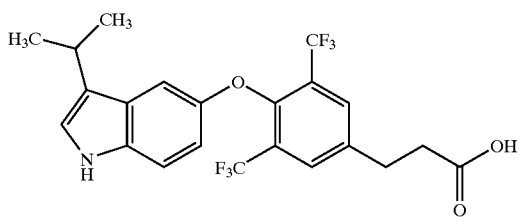

150 mg (0.328 mmol) of cinnamic acid derivative from Example 14 are dissolved in 10 ml of methanol, treated with 75 mg of palladium on active carbon (10% strength) and hydrogenated for 18 hours at hydrostatic hydrogen pressure. The palladium catalyst is filtered off with suction through kieselguhr, washed with methanol and the filtrate is concentrated to give a solid product.

| Yield: | 86.2 mg (57.2%) |
|---|---|
| MS (LC): | 460 ([M + H]⁺, 100%) |
| R_f: | 0.76 (methylene chloride:methanol = 10:1) |

¹H-NMR (200 MHz, DMSO-d6): δ = 1.19, d, 6H; 2.7, t, 2H; 2.95, quin, 1H; 3.03, t, 2H; 6.58, dd, 1H; 6.7, d, 1H; 7.08, d, 1H; 7.24, d, 1H; 8.05, s, 2H; 10.72, d, 1H; 12.25, broad s, 1H.

Example 16

{4-[(3-Isopropyl-1H-indol-5-yl)oxy]-3,5-dimethylphenoxy}acetic acid

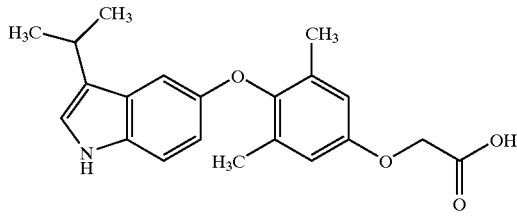

0.24 g (0.46 mmol) of tert-butyl-[4-({1-[tert-butyl-(dimethyl)silyl]-3-isopropyl-1H-indol-5-yl}oxy)-3,5-dimethylphenoxy]acetate (Example XIII) is introduced dissolved in 5 ml of ethanol and 2.5 ml (2.50 mmol) of 1N sodium hydroxide solution are added. The batch is stirred at room temperature for 2.5 h. The solvent is evaporated in a rotary evaporator, the batch is diluted with 50 ml of water and the mixture is acidified with 1N hydrochloric acid solution. The aqueous phase is extracted twice with ethyl acetate, the combined organic phases are dried and the solvent is removed in vacuo. 0.186 g (87.3%) of {4-[(3-isopropyl-1H-indol-5-yl)oxy]-3,5-dimethyl-phenoxy}acetic acid is obtained ¹H-NMR (200 MHz, CDCl₃): δ1.28, d, 6H; 2.10, s, 6H; 2.96, m, 1H; 3.08, sept., 1H; 4.58, s, 2H; 6.68, s, 3H; 6.90, dd, 2H; 7.81, s, 1H.

Example 17

4-(3-Isopropyl-1H-indol-5-yloxy)-3,5-dichlorophenylacetic acid

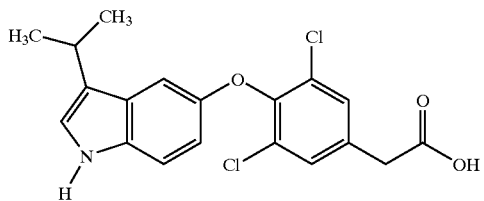

Firstly, 5 ml of conc. sulphuric acid and then 5 ml of water are added dropwise to a solution of 0.43 g (0.90 mmol) of nitrile derivative from Example XIX in 10 ml of dioxane. The reaction mixture is stirred for 4 hours at 100° C., then poured onto ice and extracted twice with ethyl acetate. The combined organic phases are washed with sodium chloride solution, dried over sodium sulphate, filtered and concentrated in vacuo. The crude product is chromatographed on silica gel 60 by means of toluene/ethyl acetate (1:1) in the isocratic mode.

| Yield: | 0.266 g (68.7%) |
|---|---|
| MS (DCI): | 395 ([M + NH₄]⁺, 100%) |
| HPLC: | R_t = 4.79 (87.8%) |
| | 0.5% HClO₄/acetonitrile |
| | Kromasil column C18 (60 × 2 mm) |
| | flow: 0.75 ml/min; 210 nm |

¹ H-NMR (200 MHz, CDCl₃): δ = 1.4 (d, 6H); 3.1 (quin, 1H); 3.65 (s, 2H); 6.76 (dd, 1H); 6.95 (d, 1H); 7.03 (d, 1H); 7.24 (d, 1H); 7.34 (s, 2H); 7.81 (broad s, 1H).

Example 18

5-{4-[(3-Isopropyl-1H-indol-5-yl)oxy]-3,5-bis-trifluoromethylphenyl}-imidazolidin-2,4-dione

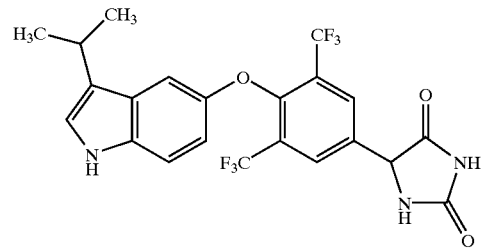

3.0 g (7.22 mmol) of aldehyde from Example V dissolved in 30 ml of ethanol are added to a solution of 0.581 g (14.4 mmol) of sodium cyanide and 3.63 g (36.1 mmol) of ammonium carbonate in 30 ml of water and the mixture is stirred for 24 hours at 60° C. Ethanol is then distilled off from the reaction solution, it is diluted with water, acidified to pH 2 with 1N hydrochloric acid with ice-cooling and extracted twice with ethyl acetate. After drying and distilling off the solvent, the crude product (4.03 g) is chromatographed on silica gel 60 using methylene chloride with addition of a little methanol in the ratio 20:1 to 20:2.5.

| Yield: | 2.73 g (78.1%) |
|---|---|
| MS (ESI): | 486 ([M + H]⁺, 100%) |
| HPLC: | R_t = 4.58 (85.1%) |
| | 0.5% HClO₄/acetonitrile |
| | Kromasil column C18 (60 × 2 mm) |
| | flow: 0.75 ml/min; 210 nm |

¹H-NMR (200 MHz, CDCl₃): δ = 1.26 (d, 6H); 3.06 (quin., 1H); 5.29 (s, 1H); 6.23 (s, 1H); 6.65 (dd, 1H); 6.9 (d, 1H); 6.95 (d, 1H); 7.2 (d, 1H); 7.8 (broad s, 1H); 7.97 (s, 2H); 8.27 (broad s, 1H).

Example 19

DL-Amino-{4-[(3-isopropyl-1H-indol-5-yl)oxy]-3,5-bis-trifluoromethylphenyl}-acetic acid

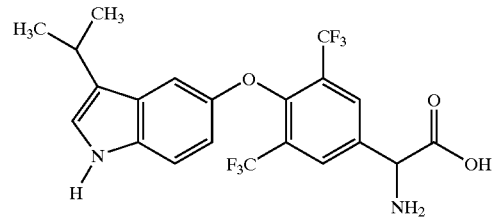

1.0 g (2.06 mmol) of hydantoin from Example 18 are heated to 100° C. with 0.493 g (20.6 mmol) of lithium hydroxide in 15 ml of water overnight. The reaction solution is cooled to 0° C. and directly reacted further with di-tert-butyl dicarbonate (Example 20).

R_f: 0.39 (methylene chloride: methanol=8:2)

Example 20

DL-tert-Butoxycarbonylamino-{4-[(3-isopropyl-1H-indol-5-yl)oxy]-3,5-bis-trifluoro-methylphenyl}-acetic acid

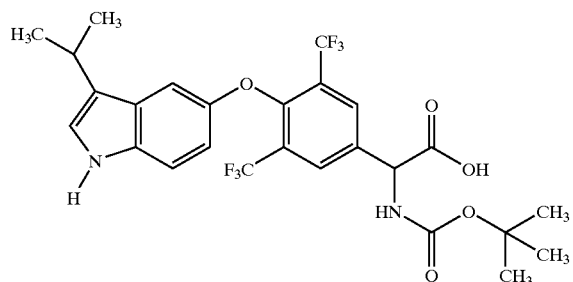

The reaction solution from Example 19 (about 2.06 mmol =100%) is treated with 50 ml of dioxane and reacted dropwise at 0° C. with 0.899 g (4.12 mmol) of di-tert-butyl dicarbonate dissolved in 5 ml of dioxane. The reaction mixture is then allowed to come to room temperature and stirred for 2 hours at room temperature. After distilling off dioxane, the reaction solution is acidified to pH 2 at 0° C. using 1N hydrochloric acid and extracted twice with ethyl acetate. The combined ethyl acetate phases are washed with sodium chloride solution, dried, filtered and concentrated. The crude product (1.234 g) is chromatographed on silica gel 60 using methylene chloride/methanol (9:1) in the isocratic mode.

| Yield: | 0.271 g (23.5%) |
|---|---|
| A 2nd fraction of 0.531 g (HPLC concentration: 64.0%) is obtained. | |
| MS (LC-MS): | 561 ([M + H]$^+$, 100%) |
| HPLC: | R$_t$ = 0.503 (91.4%) |
| | 0.5% HClO$_4$/acetonitrile |
| | Kromasil colunm C18 (60 × 2 mm) |
| | flow: 0.75 ml/min; 210 nm |

$^1$H-NMR (200 MHz, d$_6$-DMSO): δ = 1.18 (d, 6H); 1.38 (s, 9H); 2.93 (m, 1H); 3.33 (broad s, 1H); 4.99 (d, 1H); 6.59 (d, 1H); 6.7 (s, 1H); 7.08 (d, 1H); 7.25 (d, 1H); 8.1 (s, 2H); 10.75 (s, 1H).

Example 21

DL-Amino-{4-[(3-isopropyl-1H-indol-5-yl)oxy]-3,5-bis-trifluoromethylphenyl}-acetic acid acetate salt

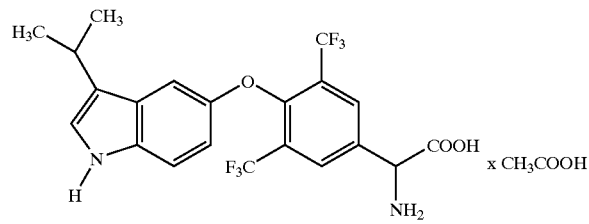

0.526 g (0.945 mmol) of tert-butoxycarbonyl-protected amino acid from Example 20 is dissolved in 7 ml of dichloromethane, cooled to 0° C. and treated dropwise under argon with 7 ml of trifluoroacetic acid. The solution is then stirred for 45 min at room temperature, subsequently concentrated to give an oil, the oily residue is stirred with ether and ether is distilled off.

| Yield: | 0.526 g | (as trifluoroacetate salt) |
|---|---|---|

The residue is dissolved in 20% strength acetic acid (20 ml) with addition of 10 ml of methanol and sent through a column packed with 80 ml of Amberlite IR-67 (acetate form; Fluka). The column is subsequently washed with water/methanol mixture (1:1), and the eluate is freed from methanol in vacuo and lyophilized.

| Yield: | 120 mg (27.8%) |
|---|---|
| MS (EI): | 460 ([M]$^+$, 14%) |
| HPLC: | R$_t$ = 4,29 (79.8%) |
| | 0.5% HClO$_4$/acetonitrile |
| | Kromasil column C18 (60 × 2 mm) |
| | flow: 0.75 ml/min; 210 nm |

Example 22

5-{4-[(3-Isopropyl-1H-indol-5-yl)oxy]-3,5-bis-trifluoromethyl-benzylidene}-thiazolidine-2,4-dione

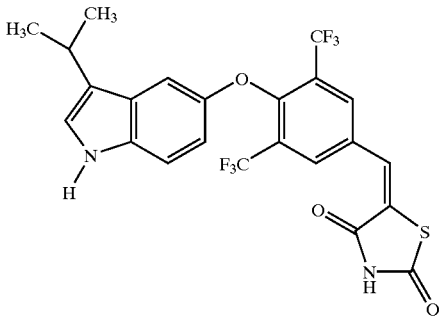

A mixture of 0.52 g (1.25 mmol) of aldehyde derivative from Example V, 0.21 g (1.63 mmol) of 2,4-thiazolidine-2,4-dione, 0.2 g (1.63 mmol) of benzoic acid and 0.14 g (1.63 mmol) of piperidine in 47.5 ml of toluene are boiled under reflux overnight in the presence of molecular sieve 4A powder. The reaction solution is then cooled to room temperature, diluted with 47.5 ml of toluene, and the molecular sieve is filtered off with suction and washed with ethyl acetate. The organic filtrate is washed twice with ammonium chloride solution, dried, filtered and concentrated in vacuo. The thioazolidine dione derivative is obtained by chromatography on silica gel 60 by means of toluene/ethyl acetate (10:1) in the isocratic mode.

| Yield: | 50 mg (4.9%) |
|---|---|
| MS (ESI): | 515 ([M + H]$^+$, 100%) |
| HPLC: | R$_t$ = 3.72 (63.2%) |
| | 0.3 g of 30% strength HCl per 1 l of H$_2$O |
| | Symmetry colunm C18 (150 × 2.1 mm) |
| | flow: 0.9 ml/min; 210 nm |

Example 23

6-{4-[(3-Isopropyl-1H-indol-5-yl)oxy]-3,5-bis-trifluoromethylphenyl}-[1,3]-thiazinan-2,4-dione

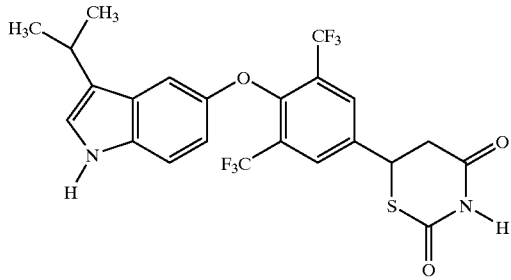

The thiazine derivative is formed as a further product in the preparation of the benzylidene-2,4-thiazolidine dione derivative (Example 22).

| Yield: | 0.123 g (14.7%) |
|---|---|
| MS (LC): | 517 ([M + H]⁺, 100%) |
| HPLC: | $R_t$ = 3.26 (77.3%) |
| | 0.3 g of 30% strength HCl per 1 l of $H_2O$ |
| | Symmetry column C18 (150 × 2.1 mm) |
| | flow: 0.9 ml/min; 210 nm |

Example 24

3-{4-[(3-Isopropyl-1H-indol-5-yl)oxy]-3,5-bis-trifluoromethyl-benzylidene}-dihydro-furan-2-one

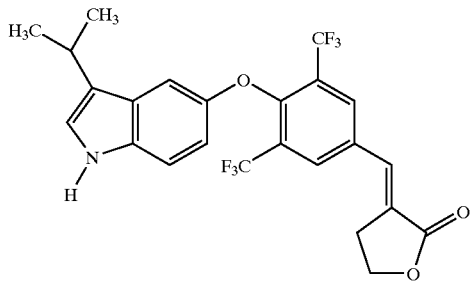

0.36 g (0.87 mmol) of aldehyde derivative from Example V are dissolved in 10 ml of toluene and 0.36 g (1.04 mmol) of butyrolactonylidene-triphenylphosphorane are introduced in portions. After stirring at room temperature for 3 days, the reaction mixture is filtered, and the filtrate is concentrated to half of the volume and chromatographed on silica gel 60 by means of toluene/ethyl acetate (9:1).

| Yield: | 0.334 g (72.5%) |
|---|---|
| MS (DCI): | 501 ([M + NH₄]⁺, 100%) |
| $R_f$: | 0.87 (toluene:ethyl acetate = 9:1) |

$^1$H-NMR (200 MHz, CDCl$_3$): δ = 1.27 (d, 6H); 3.05 (quin, 1H); 3.31 (sext, 2H); 4.55 (t, 2H); 6.71 (dd, 1H); 6.88 (d, 1H); 6.96 (d, 1H); 7.2 (d, 1H); 7.62 (t, 1H); 7.84 (broad s, 1H); 8.03 (s, 2H).

Example 25

3-{4-[(3-Isopropyl-1H-indol-5-yl)oxy]-3,5-bis-trifluoromethyl-benzyl}-dihydro-furan-2-one

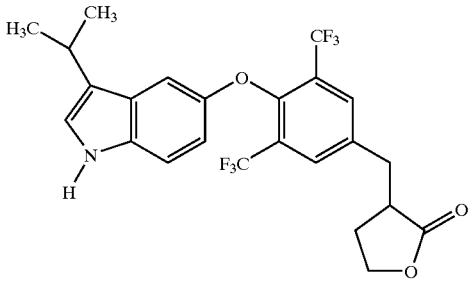

0.2 g (0.38 mmol) of benzylidene compound from Example 24 are dissolved in 100 ml of methanol and hydrogenated with hydrogen for 18 hours in the presence of palladium on active carbon. The catalyst is filtered off through kieselguhr and the filtrate is concentrated in vacuo. The crude product is purified by chromatography on silica gel 60 in the isocratic gradient mode using toluene/ethyl acetate (10:1).

| Yield: | 94 mg (48.7%) |
|---|---|
| MS (ESI): | 486 ([M + H]⁺, 100%) |
| $R_f$: | 0.35 (toluene:ethyl acetate = 9:1) |

$^1$H-NMR (300 MHz, CDCl$_3$): δ = 1.28 (d, 6H); 2.04 (m, 1H); 2.37 (m, 1H); 2.91 (m, 2H); 3.05 (quin, 1H); 3.4 (quart, 1H); 4.23 (m, 1H); 4.39 (sext, 1H); 6.69 (dd, 1H); 6.85 (d, 1H); 6.94 (d, 1H); 7.2 (d, 1H); 7.77 (s, 2H); 7.8 (s, 1H).

Example 26

Ethyl 5-{4-[(3-isopropyl-1H-indol-5-yl)oxy]-3,5-bis-trifluoromethylphenyl}-3-oxo-pent-4-ene-carboxylate

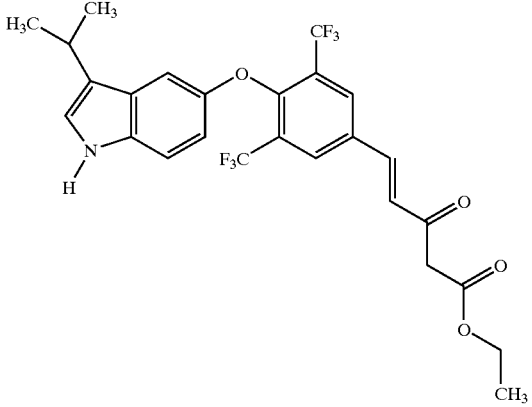

Analogously to the procedure of Example 24, 0.35 g (0.84 mmol) of aldehyde derivative from Example V is reacted with 0.36 g (0.93 mmol) of ethyl 4-(tri-phenylphosphoranylidene)-acetoacetate in 10 ml of toluene for 2 days at room temperature and then for 18 hours at 75° C. and 6 hours at 120° C. The crude product is purified by column chromatography on silica gel 60 using toluene.

| | |
|---|---|
| Yield: | 0.24 g (47.3%) |
| MS (ESI): | 528 ([M + H]+, 100%) |
| HPLC: | $R_t$ = 6.00 (27.3%) and $R_t$ = 5.35 (51.2%); E/Z mixture |
| | 0.5% $HClO_4$/acetonitrile |
| | Kromasil column C18 (60 × 2 mm) |
| | flow: 0.75 ml/min; 210 nm |

Example 27

Ethyl 5-{4-[(3-isopropyl-1H-indol-5-yl)oxy]-3,5-bis-trifluoromethylphenyl}-3-oxo-pentane-carboxylate

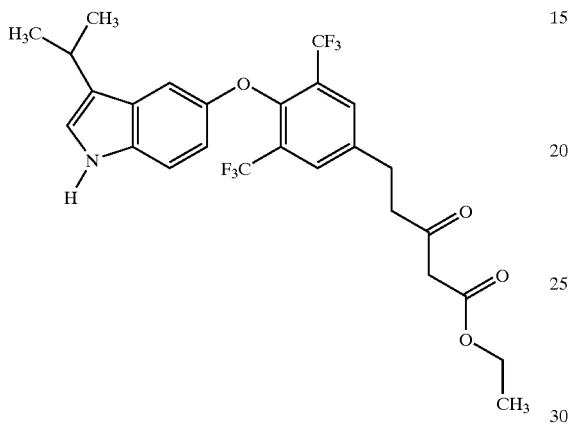

Analogously to the procedure of Example 25, 0.2 g (0.38 mmol) of 3-oxopentene-4-Carboxylic acid derivative from Example 26 is hydrogenated overnight in methanol with palladium on active carbon under a hydrogen atmosphere. The crude product is chromatographed on silica gel using toluene/ethyl acetate (10:1) in the isocratic mode.

| | |
|---|---|
| Yield: | 89 mg (38.6%) |
| MS (ESI): | 530 ([M + H]+, 100%) |
| $R_f$: | 0.37 (toluene:ethyl acetate = 9:1) |

$^1$H-NMR (200 MHz, $CDCl_3$): δ = 1.28 (d and t, 9H); 3.03 (m, 5H); 3.49 (s, 2H); 4.2 (quart, 2H); 6.7 (dd, 1H); 6.87 (d, 1H); 6.95 (d, 1H); 7.21 (d, 1H); 7.73 (s, 2H); 7.8 (s, 1H).

Example 28

Ethyl 5-{4-[(3-isopropyl-1H-indol-5-yl)oxy]-3,5-bis-trifluoromethyl-phenyl}-pentane-carboxylate

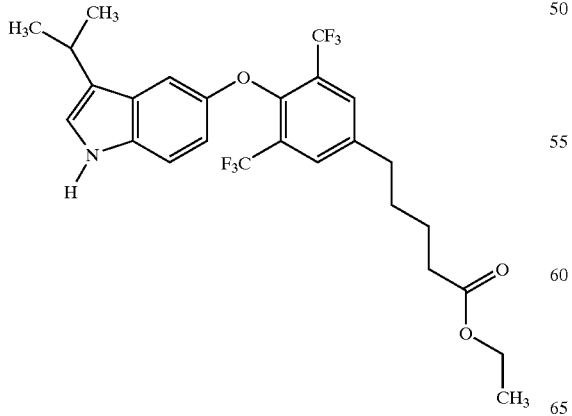

The pentanecarboxylic acid derivative is formed as a by-product in the catalytic hydrogenation of the 3-oxo-pentenecarboxylic acid derivative in Example 27.

| | |
|---|---|
| Yield: | 15 mg (6.2%) |
| MS (ESI): | 516 ([M + H]+, 100%) |
| $R_f$: | 0.4 (toluene:ethyl acetate = 9:1) |

$^1$H-NMR (200 MHz, $CDCl_3$): δ = 1.28 (d and t, 9H); 1.73 (quin, 3H); 2.39 (m, 2H); 2.78 (m, 2H); 3.04 (sext, 2H); 4.15 (quart, 2H); 6.7 (dd, 1H); 6.86 (d, 1H); 6.93 (d, 1H); 7.21 (d, 1H); 7.71 (s, 2H); 7.8 (broad s, 1H).

Example 29

4-(3-Cyclohexylmethyl-1H-indol-5-yloxy)-3,5-bis-trifluoromethylphenylacetic acid

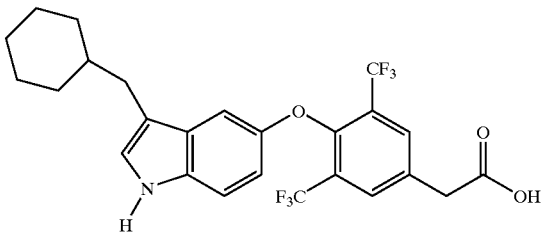

The preparation is carried out in analogy to the procedure of Example 17 from 0.3 g (0.62 mmol) of phenylacetonitrile derivative from Example XXIII by dissolving the nitrile in 10 ml of dioxane and treating it with 4 ml of conc. sulphuric acid and 4 ml of water for 4 hours at 100° C. The crude product is chromatographed on silica gel 60 by means of toluene/ethyl acetate (1:1) in the isocratic mode.

| | |
|---|---|
| Yield: | 65 mg (17.5%) |
| MS (ESI): | 500 ([M + H]+, 100%) |
| HPLC: | $R_t$ = 5.23 (82.6%) |
| | 0.5% $HClO_4$/acetonitrile |
| | Kromasil column C18 (60 × 2 mm) |
| | flow: 0.75 ml/min; 210 nm |
| $R_f$: | 0.29 (toluene:ethyl acetate = 1:1) |

$^1$H-NMR (200 MHz, $CDCl_3$): δ = 0.92 (m, 2H); 1.17 (m, 4H); 1.5 (m, 1H); 1.65 (m, 4H); 2.49 (d, 2H); 3.82 (s, 2H); 6.68 (dd, 1H); 6.84 (d, 1H); 6.93 (d, 1H); 7.2 (d, 1H); 7.85 (d and s, 3H).

The following can be prepared in an analogous manner:

Example 30
{4-[(3-Isopropyl-1H-indol-5-yl)oxy]-3,5-dimethylphenoxy}acetic acid

Example 31
{4-[(3-Cyclopropyl-1H-indol-5-yl)oxy]-3,5-dimethylphenoxy}acetic acid Example 32
{4-[(3-Cyclobutyl-1H-indol-5-yl)oxy]-3,5-dimethylphenoxy}acetic acid Example 33
{4-[(3-Cyclopentyl-1H-indol-5-yl)oxy]-3,5-dimethylphenoxy}acetic acid Example 34
{4-[(3-Cyclohexyl-1H-indol-5-yl)oxy]-3,5-dimethylphenoxy}acetic acid Example 35
{3,5-Dimethyl-4-[(3-propyl-1H-indol-5-yl)oxy]phenoxy}acetic acid Example 36
{4-[(3-Butyl-1H-indol-5-yl)oxy]-3,5-dimethylphenoxy}acetic acid Example 37
{3,5-Dimethyl-4-[(3-pentyl-1H-indol-5-yl)oxy]phenoxy}acetic acid Example 38
{4-[(3-Hexyl-1H-indol-5-yl)oxy]-3,5-dimethylphenoxy}acetic acid Example 39
{4-[(3-Isobutyl-1H-indol-5-yl)oxy]-3,5-dimethylphenoxy}acetic acid Example 40
{4-[(3-sec-Butyl-1H-indol-5-yl)oxy]-3,5-dimethylphenoxy}acetic acid Example 41
(4-{[3-(Cyclohexylmethyl)-1H-indol-5-yl]oxy}-3,5-dimethylphenoxy)acetic acid Example 42
(4-{[3-(Cyclopentylmethyl)-1H-indol-5-yl]oxy}-3,5-dimethylphenoxy)acetic acid Example 43
(4-{[3-(Cyclobutylmethyl)-1H-indol-5-yl]oxy}-3,5-dimethylphenoxy)acetic acid Example 44
(4-{[3-(Cyclopropylmethyl)-1H-indol-5-yl]oxy}-3,5-dimethylphenoxy)acetic acid Example 45
{3,5-Dichloro-4-[(3-isopropyl-1H-indol-5-yl)oxy]phenoxy}acetic acid Example 46
{3,5-Dichloro-4-[(3-cyclopropyl-1H-indol-5-yl)oxy]phenoxy}acetic acid Example 47
{3,5-Dichloro-4-[(3-cyclobutyl-1H-indol-5-yl)oxy]phenoxy}acetic acid Example 48
{3,5-Dichloro-4-[(3-cyclopentyl-1H-indol-5-yl)oxy]phenoxy}acetic acid Example 49
{3,5-Dichloro-4-[(3-cyclohexyl-1H-indol-5-yl)oxy]phenoxy}acetic acid Example 50
{3,5-Dichloro-4-[(3-propyl-1H-indol-5-yl)oxy]phenoxy}acetic acid Example 51
{4-[(3-Butyl-1H-indol-5-yl)oxy]-3,5-dichlorophenoxy}acetic acid Example 52
{3,5-Dichloro-4-[(3-pentyl-1H-indol-5-yl)oxy]phenoxy}acetic acid Example 53
{3,5-Dichloro-4-[(3-hexyl-1H-indol-5-yl)oxy]phenoxy}acetic acid Example 54
{3,5-Dichloro-4-[(3-isobutyl-1H-indol-5-yl)oxy]phenoxy}acetic acid Example 55
{4-[(3-sec-Butyl-1H-indol-5-yl)oxy]-3,5-dichlorophenoxy}acetic acid Example 56
(3,5-Dichloro-4-{[3-(cyclohexylmethyl)-1H-indol-5-yl]oxy}phenoxy)acetic acid Example 57
(3,5-Dichloro-4-{[3-(cyclopentylmethyl)-1H-indol-5-yl]oxy}phenoxy)acetic acid Example 58
(3,5-Dichloro-4-{[3-(cyclobutylmethyl)-1H-indol-5-yl]oxy}phenoxy)acetic acid Example 59
(3,5-Dichloro-4-{[3-(cyclopropylmethyl)-1H-indol-5-yl]oxy}phenoxy)acetic acid Example 60
{3,5-Dibromo-4-[(3-isopropyl-1H-indol-5-yl)oxy]phenoxy}acetic acid Example 61
{3,5-Dibromo-4-[(3-cyclopropyl-1H-indol-5-yl)oxy]phenoxy}acetic acid Example 62
{3,5-Dibromo-4-[(3-cyclobutyl-1H-indol-5-yl)oxy]phenoxy}acetic acid Example 63
{3,5-Dibromo-4-[(3-cyclopentyl-1H-indol-5-yl)oxy]phenoxy}acetic acid Example 64
{3,5-Dibromo-4-[(3-cyclohexyl-1H-indol-5-yl)oxy]phenoxy}acetic acid Example 65
{3,5-Dibromo-4-[(3-propyl-1H-indol-5-yl)oxy]phenoxy}acetic acid Example 66
{3,5-Dibromo-4-[(3-butyl-1H-indol-5-yl)oxy]phenoxy}acetic acid Example 67
{3,5-Dibromo-4-[(3-pentyl-1H-indol-5-yl)oxy]phenoxy}acetic acid Example 68
{3,5-Dibromo-4-[(3-hexyl-1H-indol-5-yl)oxy]phenoxy}acetic acid Example 69
{3,5-Dibromo-4-[(3-isobutyl-1H-indol-5-yl)oxy]phenoxy}acetic acid Example 70
{3,5-Dibromo-4-[(3-sec-butyl-1H-indol-5-yl)oxy]phenoxy}acetic acid Example 71
(3,5-Dibromo-4-{[3-(cyclohexylmethyl)-1H-indol-5-yl]oxy}phenoxy)acetic acid Example 72
(3,5-Dibromo-4-{[3-(cyclopentylmethyl)-1H-indol-5-yl]oxy}phenoxy)acetic acid Example 73
(3,5-Dibromo-4-{[3-(cyclobutylmethyl)-1H-indol-5-yl]oxy}phenoxy)acetic acid Example 74
(3,5-Dibromo-4-{[3-(cyclopropylmethyl)-1H-indol-5-yl]oxy}phenoxy)acetic acid Example 75
[4-[(3-Isopropyl-1H-indol-5-yl)oxy]-3,5-bis(trifluoromethyl)phenoxy]acetic acid Example 76
[4-[(3-Cyclopropyl-1H-indol-5-yl)oxy]-3,5-bis(trifluoromethyl)phenoxy]acetic acid Example 77
[4-[(3-Cyclobutyl-1H-indol-5-yl)oxy]-3,5-bis(trifluoromethyl)phenoxy]acetic acid Example 78
[4-[(3-Cyclopentyl-1H-indol-5-yl)oxy]-3,5-bis(trifluoromethyl)phenoxy]acetic acid Example 79
[4-[(3-Cyclohexyl-1H-indol-5-yl)oxy]-3,5-bis(trifluoromethyl)phenoxy]acetic acid Example 80
[4-[(3-Propyl-1H-indol-5-yl)oxy]-3,5-bis(trifluoromethyl)phenoxy]acetic acid Example 81
[4-[(3-Butyl-1H-indol-5-yl)oxy]-3,5-bis(trifluoromethyl)phenoxy]acetic acid Example 82
[4-[(3-Pentyl-1H-indol-5-yl)oxy]-3,5-bis(trifluoromethyl)phenoxy]acetic acid Example 83
[4-[(3-Hexyl-1H-indol-5-yl)oxy]-3,5-bis(trifluoromethyl)phenoxy]acetic acid Example 84
[4-[(3-Isobutyl-1H-indol-5-yl)oxy]-3,5-bis(trifluoromethyl)phenoxy]acetic acid Example 85
[4-[(3-sec-Butyl-1H-indol-5-yl)oxy]-3,5-bis(trifluoromethyl)phenoxy]acetic acid Example 86
[4-{[3-(Cyclohexylmethyl)-1H-indol-5-yl]oxy}-3,5-bis(trifluoromethyl)phenoxy]-acetic acid Example 87
[4-{[3-(Cyclopentylmethyl)-1H-indol-5-yl]oxy}-3,5-bis(trifluoromethyl)phenoxy]-acetic acid Example 88
[4-{[3-(Cyclobutylmethyl)-1H-indol-5-yl]oxy}-3,5-bis(trifluoromethyl)phenoxy]-acetic acid Example 89
[4-{[3-(Cyclopropylmethyl)-1H-indol-5-yl]oxy}-3,5-bis(trifluoromethyl)phenoxy]-acetic acid Example 90
[4-[(3-Isopropyl-1H-indol-5-yl)oxy]-3-methyl-5-(trifluoromethyl)phenoxy]acetic acid Example 91
[4-[(3-Cyclopropyl-1H-indol-5-yl)oxy]-3-methyl-5-(trifluoromethyl)phenoxy]-acetic acid Example 92
[4-[(3-cyclobutyl-1H-indol-5-yl)oxy]-3-methyl-5-(trifluoromethyl)phenoxy]acetic acid Example 93
[4-[(3-Cyclopentyl-1H-indol-5-yl)oxy]-3-methyl-5-(trifluoromethyl)phenoxy]-acetic acid Example 94
[4-[(3-Cyclohexyl-1H-indol-5-yl)oxy]-3-methyl-5-(trifluoromethyl)phenoxy]-acetic acid Example 95
[3-Methyl-4-[(3-propyl-1H-indol-5-yl)oxy]-5-(trifluoromethyl)phenoxy]acetic acid Example 96
[4-[(3-Butyl-1H-indol-5-yl)oxy]-3-methyl-5-(trifluoromethyl)phenoxy]acetic acid Example 97
[3-Methyl-4-[(3-pentyl-1H-indol-5-yl)oxy]-5-(trifluoromethyl)phenoxy]acetic acid Example 98
[4-[(3-Hexyl-1H-indol-5-yl)oxy]-3-methyl-5-(trifluoromethyl)phenoxy]acetic acid Example 99
[4-[(3-Isobutyl-1H-indol-5-yl)oxy]-3-methyl-5-(trifluoromethyl)phenoxy]acetic acid Example 100
[4-[(3-sec-Butyl-1H-indol-5-yl)oxy]-3-methyl-5-(trifluoromethyl)phenoxy]acetic acid Example 101
[4-{[3-(Cyclohexylmethyl)-1H-indol-5-yl]oxy}-3-methyl-5-(trifluoromethyl)phenoxy]-acetic acid Example 102
[4-{[3-(Cyclopentylmethyl)-1H-indol-5-yl]oxy}-3-methyl-5-(trifluoromethyl)phenoxy]-acetic acid Example 103
[4-{[3-(Cyclobutylmethyl)-1H-indol-5-yl]oxy}-3-methyl-5-(trifluoromethyl)phenoxy]-acetic acid Example 104
[4-{[3-(Cyclopropylmethyl)-1H-indol-5-yl]oxy}-3-methyl-5-(trifluoromethyl)-phenoxy]acetic acid Example 105
{3-Bromo-4-[(3-isopropyl-1H-indol-5-yl)oxy]-5-methylphenoxy}acetic acid Example 106
{3-Bromo-4-[(3-cyclopropyl-1H-indol-5-yl)oxy]-5-methylphenoxy}acetic acid Example 107
{3-Bromo-4-[(3-cyclobutyl-1H-indol-5-yl)oxy]-5-methylphenoxy}acetic acid Example 108
{3-Bromo-4-[(3-cyclopentyl-1H-indol-5-yl)oxy]-5-methylphenoxy}acetic acid Example 109
{3-Bromo-4-[(3-cyclohexyl-1H-indol-5-yl)oxy]-5-methylphenoxy}acetic acid Example 110
{3-Bromo-5-methyl-4-[(3-propyl-1H-indol-5-yl)oxy]phenoxy}acetic acid Example 111
{3-Bromo-4-[(3-butyl-1H-indol-5-yl)oxy]-5-methylphenoxy}acetic acid Example 112
{3-Bromo-5-methyl-4-[(3-pentyl-1H-indol-5-yl)oxy]phenoxy}acetic acid Example 113
{3-Bromo-4-[(3-hexyl-1H-indol-5-yl)oxy]-5-methylphenoxy}acetic acid Example 114
{3-Bromo-4-[(3-isobutyl-1H-indol-5-yl)oxy]-5-methylphenoxy}acetic acid Example 115
{3-Bromo-4-[(3-sec-butyl-1H-indol-5-yl)oxy]-5-methylphenoxy}acetic acid Example 116
(3-Bromo-4-{[3-(cyclohexylmethyl)-1H-indol-5-yl]oxy}-methylphenoxy)acetic acid Example 117
(3-Bromo-4-{[3-(cyclopentylmethyl)-1H-indol-5-yl]oxy}-5-methylphenoxy)acetic acid Example 118
(3-Bromo-4-{[3-(cyclobutylmethyl)-1H-indol-5-yl]oxy}-5-methylphenoxy)acetic acid Example 119
(3-Bromo-4-{[3-(cyclopropylmethyl)-1H-indol-5-yl]oxy}-5-methylphenoxy)acetic acid Example 120
{3-chloro-4-[(3-isopropyl-1H-indol-5-yl)oxy]-5-methylphenoxy}acetic acid Example 121
{3-chloro-4-[(3-cyclopropyl-1H-indol-5-yl)oxy]-5-methylphenoxy}acetic acid Example 122
{3-chloro-4-[(3-cyclobutyl-1H-indol-5-yl)oxy]-5-methylphenoxy}acetic acid Example 123
{3-chloro-4-[(3-cyclopentyl-1H-indol-5-yl)oxy]-5-methylphenoxy}acetic acid Example 124
{3-chloro-4-[(3-cyclohexyl-1H-indol-5-yl)oxy]-5-methylphenoxy}acetic acid Example 125
{3-chloro-5-methyl-4-[(3-propyl-1H-indol-5-yl)oxy]phenoxy}acetic acid Example 126
{4-[(3-Butyl-1H-indol-5-yl)oxy]-3-chloro-5-methylphenoxy}acetic acid Example 127
{3-chloro-5-methyl-4-[(3-pentyl-1H-indol-5-yl)oxy]phenoxy}acetic acid Example 128
{3-chloro-4-[(3-hexyl-1H-indol-5-yl)oxy]-5-methylphenoxy}acetic acid Example 129
{3-chloro-4-[(3-isobutyl-1H-indol-5-yl)oxy]-5-methylphenoxy}acetic acid Example 130
{4-[(3-sec-butyl-1H-indol-5-yl)oxy]-3-chloro-5-methylphenoxy}acetic acid Example 131
(3-chloro-4-{[3-(cyclohexylmethyl)-1H-indol-5-yl]oxy}-5-methylphenoxy)acetic acid Example 132
(3-chloro-4-{[3-(cyclopentylmethyl)-1H-indol-5-yl]oxy}-5-methylphenoxy)acetic acid Example 133
(3-chloro-4-{[3-(cyclobutylmethyl)-1H-indol-5-yl]oxy}-5-methylphenoxy)acetic Example 134
(3-chloro-4-{[3-(cyclopropylmethyl)-1H-indol-5-yl]oxy}-5-methylphenoxy)acetic acid Example 135
{3-Bromo-5-chloro-4-[(3-isopropyl-1H-indol-5-yl)oxy]phenoxy}acetic acid Example 136
{3-Bromo-5-chloro-4-[(3-cyclopropyl-1H-indol-5-yl)oxy]phenoxy}acetic acid Example 137
{3-Bromo-5-chloro-4-[(3-cyclobutyl-1H-indol-5-yl)oxy]phenoxy}acetic acid Example 138
{3-Bromo-5-chloro-4-[(3-cyclopentyl-1H-indol-5-yl)oxy]phenoxy}acetic acid Example 139
{3-Bromo-5-chloro-4-[(3-cyclohexyl-1H-indol-5-yl)oxy]phenoxy}acetic acid Example 140
{3-Bromo-5-chloro-4-[(3-propyl-1H-indol-5-yl)oxy]phenoxy}acetic acid Example 141
{3-Bromo-4-[(3-butyl-1H-indol-5-yl)oxy]-5-chlorophenoxy}acetic acid Example 142
{3-Bromo-5-chloro-4-[(3-pentyl-1H-indol-5-yl)oxy]phenoxy}acetic acid Example 143
{3-Bromo-5-chloro-4-[(3-hexyl-1H-indol-5-yl)oxy]phenoxy}acetic acid Example 144
{3-Bromo-5-chloro-4-[(3-isobutyl-1H-indol-5-yl)oxy]phenoxy}acetic acid Example 145
{3-Bromo-4-[(3-sec-butyl-1H-indol-5-yl)oxy]-5-chlorophenoxy}acetic acid Example 146
(3-Bromo-5-chloro-4-{[3-(cyclohexylmethyl)-1H-indol-5-yl]oxy}phenoxy)acetic acid Example 147
(3-Bromo-5-chloro-4-{[3-(cyclopentylmethyl)-1H-indol-5-yl]oxy}phenoxy)acetic acid Example 148
(3-Bromo-5-chloro-4-{[3-(cyclobutylmethyl)-1H-indol-5-yl]oxy}phenoxy)acetic acid Example 149
(3-Bromo-5-chloro-4-{[3-(cyclopropylmethyl)-1H-indol-5-yl]oxy}phenoxy)acetic acid Example 150
[3-chloro-4-[(3-isopropyl-1H-indol-5-yl)oxy]-5-(trifluoromethyl)phenoxy]acetic acid Example 151
3-chloro-4-[(3-cyclopropyl-1H-indol-5-yl)oxy]-5-(trifluoromethyl)phenoxy]acetic acid Example 152
[3-chloro-4-[(3-cyclobutyl-1H-indol-5-yl)oxy]-5-(trifluoromethyl)phenoxy]acetic acid Example 153
[3-chloro-4-[(3-cyclopentyl-1H-indol-5-yl)oxy]-5-(trifluoromethyl)phenoxy]acetic acid Example 154
[3-chloro-4-[(3-cyclohexyl-1H-indol-5-yl)oxy]-5-(trifluoromethyl)phenoxy]acetic acid Example 155
[3-chloro-4-[(3-propyl-1H-indol-5-yl)oxy]-5-(trifluoromethyl)phenoxy]acetic acid Example 156
[4-[(3-Butyl-1H-indol-5-yl)oxy]-3-chloro-5-(trifluoromethyl)phenoxy]acetic acid Example 157
[3-Chloro-4-[(3-pentyl-1H-indol-5-yl)oxy]-5-(trifluoromethyl)phenoxy]acetic acid Example 158
[3-Chloro-4-[(3-hexyl-1H-indol-5-yl)oxy]-5-(trifluoromethyl)phenoxy]acetic acid Example 159
[3-Chloro-4-[(3-isobutyl-1H-indol-5-yl)oxy]-5-(trifluoromethyl)phenoxy]acetic acid Example 160
[4-[(3-sec-Butyl-1H-indol-5-yl)oxy]-3-chloro-5-(trifluoromethyl)phenoxy]acetic acid Example 161
[3-Chloro-4-{[3-(cyclopentylmethyl)-1H-indol-5-yl]oxy}-5-(trifluoromethyl)-phenoxy]-acetic acid Example 162
[3-Chloro-4-{[3-(cyclopentylmethyl)-1H-indol-5-yl]oxy}-5-(trifluoromethyl)-phenoxy]-acetic acid Example 163
[3-Chloro-4-{[3-(cyclobutylmethyl)-1H-indol-5-yl]oxy}-5-(trifluoromethyl)-phenoxy]-acetic acid Example 164
[3-Chloro-4-{[3-(cyclopropylmethyl)-1H-indol-5-yl]oxy}-5-(trifluoromethyl)-phenoxy]-acetic acid Example 165
[3-Bromo-4-[(3-isopropyl-1H-indol-5-yl)oxy]-5-(trifluoromethyl)phenoxy]acetic acid Example 166
[3-Bromo-4-[(3-cyclopropyl-1H-indol-5-yl)oxy]-5-(trifluoromethyl)phenoxy]acetic acid Example 167
[3-Bromo-4-[(3-cyclobutyl-1H-indol-5-yl)oxy]-5-(trifluoromethyl)phenoxy]acetic acid Example 168
[3-Bromo-4-[(3-cyclopentyl-1H-indol-5-yl)oxy]-5-(trifluoromethyl)phenoxy]acetic acid Example 169
[3-Bromo-4-[(3-cyclohexyl-1H-indol-5-yl)oxy]-5-(trifluoromethyl)phenoxy]acetic acid Example 170
[3-Bromo-4-[(3-propyl-1H-indol-5-yl)oxy]-5-(trifluoromethyl)phenoxy]acetic acid Example 171
[3-Bromo-4-[(3-butyl-1H-indol-5-yl)oxy]-5-(trifluoromethyl)phenoxy]acetic acid Example 172
[3-Bromo-4-[(3-pentyl-1H-indol-5-yl)oxy]-5-(trifuoromethyl)phenoxy]acetic acid Example 173
[3-Bromo-4-[(3-hexyl-1H-indol-5-yl)oxy]-5-(trifluoromethyl)phenoxy]acetic acid Example 174
[3-Bromo-4-[(3-isobutyl-1H-indol-5-yl)oxy]-5-(trifluoromethyl)phenoxy]acetic acid Example 175
[3-Bromo-4-[(3-sec-butyl-1H-indol-5-yl)oxy]-5-(trifluoromethyl)phenoxy]acetic acid Example 176
[3-Bromo-4-{[3-(cyclohexylmethyl)-1H-indol-5-yl]oxy}-5-(trifluoromethyl)-phenoxy]-acetic acid Example 177
[3-Bromo-4-{[3-(cyclopentylmethyl)-1H-indol-5-yl]oxy}-5-(trifluoromethyl)-phenoxy]-acetic acid Example 178
[3-Bromo-4-{[3-(cyclobutylmethyl)-1H-indol-5-yl]oxy}-5-(trifluoromethyl)-phenoxy]-acetic acid Example 179
[3-Bromo-4-{[3-(cyclopropylmethyl)-1H-indol-5-yl]oxy}-5-(trifluoromethyl)-phenoxy]-acetic acid Example 180
({4-[(3-Isopropyl-1H-indol-5-yl)oxy]-3,5-dimethylphenyl}sulphanyl)acetic acid Example 181
({3,5-Dichloro-4-[(3-isopropyl-1H-indol-5-yl)oxy]phenyl}sulphanyl)acetic acid Example 182
({3,5-Dibromo-4-[(3-isopropyl-1H-indol-5-yl)oxy]phenyl}sulphanyl)acetic acid Example 183
{[4-[(3-Isopropyl-1H-indol-5-yl)oxy]-3,5-bis(trifluoromethyl)phenyl]sulphanyl}-acetic acid Example 184
{[4-[(3-Isopropyl-1H-indol-5-yl)oxy]-3-methyl-5-(trifluoromethyl)phenyl]sulphanyl}-acetic acid Example 185
({3-Chloro-4-[(3-isopropyl-1H-indol-5-yl)oxy]-5-methylphenyl}sulphanyl)acetic acid Example 186
({3-Bromo-4-[(3-isopropyl-1H-indol-5-yl)oxy]-5-methylphenyl}sulphanyl)acetic acid Example 187
({3-Bromo-5-chloro-4-[(3-isopropyl-1H-indol-5-yl)oxy]phenyl}sulphanyl)acetic acid Example 188
{[3-Bromo-4-[(3-isopropyl-1H-indol-5-yl)oxy]-5-(trifluoromethyl)phenyl]sulphanyl}-acetic acid Example 189
{[3-Chloro-4-[(3-isopropyl-1H-indol-5-yl)oxy]-5-(trifluoromethyl)phenyl]sulphanyl}-acetic acid Example 190
N-[3-Chloro-4-[(3-isopropyl-1H-indol-5-yl)oxy]-5-(trifluoromethyl)phenyl]glycine Example 191
N-[3-Bromo-4-[(3-isopropyl-1H-indol-5-yl)oxy]-5-(trifluoromethyl)phenyl]glycine Example 192
N-{3-Bromo-5-chloro-4-[(3-isopropyl-1H-indol-5-yl)oxy]phenyl}glycine Example 193
N-{3-Bromo-4-[(3-isopropyl-1H-indol-5-yl)oxy]-5-methylphenyl}glycine Example 194
N-{3-Chloro-4-[(3-isopropyl-1H-indol-5-yl)oxy]-5-methylphenyl}glycine Example 195
N-[4-[(3-Isopropyl-1H-indol-5-yl)oxy]-3-methyl-5-(trifluoromethyl)phenyl]glycine Example 196
N-[4-[(3-Isopropyl-1H-indol-5-yl)oxy]-3,5-bis(trifluoromethyl)phenyl]glycine

Example 197

N-{3,5-Dibromo-4-[(3-isopropyl-1H-indol-5-yl)oxy]phenyl}glycine

Example 198

N-{3,5-Dichloro-4-[(3-isopropyl-1H-indol-5-yl)oxy]phenyl}glycine

Example 199

N-{4-[(3-Isopropyl-1H-indol-5-yl)oxy]-3,5-dimethylphenyl}glycine

Example 200

3-{[3-Chloro-4-[(3-isopropyl-1H-indol-5-yl)oxy]-5-(trifluoromethyl)phenyl]amino}-3-oxopropionic acid

Example 201

3-{[3-Bromo-4-[(3-isopropyl-1H-indol-5-yl)oxy]-5-(trifluoromethyl)phenyl]amino}-3-oxopropionic acid

Example 202

3-({3-Bromo-5-chloro-4-[(3-isopropyl-1H-indol-5-yl)oxy]phenyl}amino)-3-oxo-propionic acid

Example 203

3-({3-Bromo-4-[(3-isopropyl-1H-indol-5-yl)oxy]-5-methylphenyl}amino)-3-oxopropionic acid

Example 204

3-({3-Chloro-4-[(3-isopropyl-1H-indol-5-yl)oxy]-5-methylphenyl}amino)-3-oxo-propionic acid

Example 205

3-{[4-[(3-Isopropyl-1H-indol-5-yl)oxy]-3-methyl-5-(trifluoromethyl)phenyl]amino}-3-oxopropionic acid

Example 206

3-{[4-[(3-Isopropyl-1H-indol-5-yl)oxy]-3,5-bis(trifluoromethyl)phenyl]amino}-3-oxopropionic acid

Example 207

3-({3,5-Dibromo-4-[(3-isopropyl-1H-indol-5-yl)oxy]phenyl}amino)-3-oxopropionic acid

Example 208

3-({3,5-Dichloro-4-[(3-isopropyl-1H-indol-5-yl)oxy]phenyl}amino)-3-oxopropionic acid

Example 209

3-({4-[(3-Isopropyl-1H-indol-5-yl)oxy]-3,5-dimethylphenyl}amino)-3-oxopropionic acid

Example 210

3-{[3-Chloro-4-[(3-isopropyl-1H-indol-5-yl)oxy]-5-(trifluoromethyl)phenyl]amino}-2-oxopropionic acid

Example 211

3-{[3-Bromo-4-[(3-isopropyl-1H-indol-5-yl)oxy]-5-(trifluoromethyl)phenyl]amino}-2-oxopropionic acid

Example 212

3-({3-Bromo-5-chloro-4-[(3-isopropyl-1H-indol-5-yl)oxy]phenyl}amino)-2-oxopropionic acid

Example 213

3-({3-Bromo-4-[(3-isopropyl-H-indol-5-yl)oxy]-5-methylphenyl}amino)-2-oxo-propionic acid

Example 214

3-({3-Chloro-4-[(3-isopropyl-1H-indol-5-yl)oxy]-5-methylphenyl}amino)-2-oxo-propionic acid

Example 215

3-{[4-[(3-Isopropyl-1H-indol-5-yl)oxy]-3-methyl-5-(trifluoromethyl)phenyl]amino}-2-oxopropionic acid

Example 216

3-{[4-[(3-Isopropyl-1H-indol-5-yl)oxy]-3,5-bis(trifluoromethyl)phenyl]amino}-2-oxopropionic acid

Example 217

3-({3,5-Dibromo-4-[(3-isopropyl-1H-indol-5-yl)oxy]phenyl}amino)-2-oxopropionic

Example 218

3-({3,5-Dichloro-4-[(3-isopropyl-1H-indol-5-yl)oxy]phenyl}amino)-2-oxopropionic acid

Example 219

3-({4-[(3-Isopropyl-1H-indol-5-yl)oxy]-3,5-dimethylphenyl}amino)-2-oxopropionic acid

Example 220

3-[3-Chloro-4-[(3-isopropyl-1H-indol-5-yl)oxy]-5-(trifluoromethyl)phenyl]propionic acid

Example 221

3-[3-Bromo-4-[(3-isopropyl-1H-indol-5-yl)oxy]-5-(trifluoromethyl)phenyl]propionic acid

Example 222

3-{3-Bromo-5-chloro-4-[(3-isopropyl-1H-indol-5-yl)oxy]phenyl}propionic acid

Example 223

3-{3-Bromo-4-[(3-isopropyl-1H-indol-5-yl)oxy]-5-methylphenyl}propionic acid

Example 224

3-{3-Chloro-4-[(3-isopropyl-1H-indol-5-yl)oxy]-5-methylphenyl}propionic acid

Example 225
3-[4-[(3-Isopropyl-1H-indol-5-yl)oxy]-3-methyl-5-(trifluoromethyl)phenyl]-propionic acid Example 226
3-[4-[(3-Isopropyl-1H-indol-5-yl)oxy]-3,5-bis(trifluoromethyl)phenyl]propionic acid Example 227
3-{3,5-Dibromo-4-[(3-isopropyl-1H-indol-5-yl)oxy]phenyl}propionic acid Example 228
3-{3,5-Dichloro-4-[(3-isopropyl-1H-indol-5-yl)oxy]phenyl}propionic acid Example 229
3-{4-[(3-Isopropyl-1H-indol-5-yl)oxy]-3,5-dimethylphenyl}propionic acid Example 230
[3-Chloro-4-[(3-isopropyl-1H-indol-5-yl)oxy]-5-(trifluoromethyl)phenyl]acetic acid Example 231
[3-Chloro-4-[(3-cyclopropyl-1H-indol-5-yl)oxy]-5-(trifluoromethyl)phenyl]acetic acid Example 232
[3-Chloro-4-[(3-cyclobutyl-1H-indol-5-yl)oxy]-5-(trifluoromethyl)phenyl]acetic acid Example 233
[3-Chloro-4–4-[(3-cyclopentyl-1H-indol-5-yl)oxy]-5-(trifluoromethyl)phenyl]acetic acid Example 234
[3-Chloro-4-[(3-cyclohexyl-1H-indol-5-yl)oxy]-5-(trifluoromethyl)phenyl]acetic acid Example 235
[3-Chloro-4-[(3-propyl-1H-indol-5-yl)oxy]-5-(trifluoromethyl)phenyl]acetic acid Example 236
[4-[(3-Butyl-1H-indol-5-yl)oxy]-3-chloro-5-(trifluoromethyl)phenyl]acetic acid Example 237
[3-Chloro-4-[(3-pentyl-1H-indol-5-yl)oxy]-5-(trifluoromethyl)phenyl]acetic acid Example 238
[3-Chloro-4-[(3-hexyl-1H-indol-5-yl)oxy]-5-(trifluoromethyl)phenyl]acetic acid Example 239
[3-Chloro-4-[(3-isobutyl-1H-indol-5-yl)oxy]-5-(trifluoromethyl)phenyl]acetic acid Example 240
[4-[(3-sec-Butyl-1H-indol-5-yl)oxy]-3-chloro-5-(trifluoromethyl)phenyl]acetic acid Example 241
[3-Chloro-4-{[3-(cyclohexylmethyl)-1H-indol-5-yl]oxy}-5-(trifluoromethyl)phenyl]-acetic acid Example 242
[3-Chloro-4-{[3-(cyclopentylmethyl)-1H-indol-5-yl]oxy}-5-(trifluoromethyl)phenyl]-acetic acid Example 243
[3-Chloro-4-{[3-(cyclobutylmethyl)-1H-indol-5-yl]oxy}-5-(trifluoromethyl)phenyl]-acetic acid Example 244
[3-Chloro-4-{[3-(cyclopropylmethyl)-1H-indol-5-yl]oxy}-5-(trifluoromethyl)phenyl]-acetic acid Example 245
[4-[(3-Benzyl-1H-indol-5-yl)oxy]-3-chloro-5-(trifluoromethyl)phenyl]acetic acid Example 246
[3-Chloro-4-{[3-(4-chlorobenzyl)-1H-indol-5-yl]oxy}-5-(trifluoromethyl)phenyl]-acetic acid Example 247
[3-Chloro-4-{[3-(4-fluorobenzyl)-1H-indol-5-yl]oxy}-5-(trifluoromethyl)phenyl]-acetic acid Example 248
[3-Chloro-4-({3-[(4-fluorophenyl)sulphonyl]-1H-indol-5-yl}oxy)-5-(trifluoro-methyl)-phenyl]acetic acid Example 249
[3-Chloro-4-({3-[(4-chlorophenyl)sulphonyl]-1H-indol-5-yl}oxy)-5-(trifluoro-methyl)-phenyl]acetic acid Example 250
[3-Chloro-4-{[3-(phenylsulphonyl)-1H-indol-5-yl]oxy}-5-(trifluoromethyl)-phenyl]-acetic acid Example 251
[3-Bromo-4-[(3-isopropyl-1H-indol-5-yl)oxy]-5-(trifluoromethyl)phenyl]acetic acid Example 252
[3-Bromo-4-[(3-cyclopropyl-1H-indol-5-yl)oxy]-5-(trifluoromethyl)phenyl]acetic acid Example 253
[3-Bromo-4-[(3-cyclobutyl-1H-indol-5-yl)oxy]-5-(trifluoromethyl)phenyl]acetic acid Example 254
[3-Bromo-4-[(3-cyclopentyl-1H-indol-5-yl)oxy]-5-(trifluoromethyl)phenyl]acetic acid Example 255
[3-Bromo-4-[(3-cyclohexyl-1H-indol-5-yl)oxy]-5-(trifluoromethyl)phenyl]acetic acid Example 256
[3-Bromo-4-[(3-propyl-1H-indol-5-yl)oxy]-5-(trifluoromethyl)phenyl]acetic acid Example 257
[3-Bromo-4-[(3-butyl-1H-indol-5-yl)oxy]-5-(trifluoromethyl)phenyl]acetic acid Example 258
[3-Bromo-4-[(3-pentyl-1H-indol-5-yl)oxy]-5-(trifluoromethyl)phenyl]acetic acid Example 259
[3-Bromo-4-[(3-hexyl-1H-indol-5-yl)oxy]-5-(trifluoromethyl)phenyl]acetic acid Example 260
[3-Bromo-4-[(3-isobutyl-1H-indol-5-yl)oxy]-5-(trifluoromethyl)phenyl]acetic acid Example 261
[3-Bromo-4-[(3-sec-butyl-1H-indol-5-yl)oxy]-5-(trifluoromethyl)phenyl]acetic acid Example 262
[3-Bromo-4-{[3-(cyclohexylmethyl)-1H-indol-5-yl]oxy}-5-(trifluoromethyl)phenyl]-acetic acid Example 263
[3-Bromo-4-{[3-(cyclopentylmethyl)-1H-indol-5-yl]oxy}-5-(trifluoromethyl)phenyl]-acetic acid Example 264
[3-Bromo-4-{[3-(cyclobutylmethyl)-1H-indol-5-yl]oxy}-5-(trifluoromethyl)phenyl]-acetic acid Example 265
[3-Bromo-4-{[3-(cyclopropylmethyl)-1H-indol-5-yl]oxy}-5-(trifluoromethyl)-phenyl]-acetic acid Example 266
[4-[(3-Benzyl-1H-indol-5-yl)oxy]-3-bromo-5-(trifluoromethyl)phenyl]acetic acid Example 267
[3-Bromo-4-{[3-(4-chlorobenzyl)-1H-indol-5-yl]oxy}-5-(trifluoromethyl)phenyl]-acetic acid Example 268
[3-Bromo-4-{[3-(4-fluorobenzyl)-1H-indol-5-yl]oxy}-5-(trifluoromethyl)phenyl]-acetic acid Example 269
[3-Bromo-4-({3-[(4-fluorophenyl)sulphonyl]-1H-indol-5-yl}oxy)-5-(trifluoro-methyl)-phenyl]acetic acid Example 270
[3-Bromo-4-({3-[(4-chlorophenyl)sulphonyl]-1H-indol-5-yl}oxy)-5-(trifluoro-methyl)-phenyl]acetic acid Example 271
[3-Bromo-4-{[3-(phenylsulphonyl)-1H-indol-5-yl]oxy}-5-(trifluoromethyl)phenyl]-acetic acid Example 272
{3-Bromo-5-chloro-4-[(3-isopropyl-1H-indol-5-yl)oxy]phenyl}acetic acid Example 273
{3-Bromo-5-chloro-4-[(3-cyclopropyl-1H-indol-5-yl)oxy]phenyl}acetic acid Example 274
{3-Bromo-5-chloro-4-[(3-cyclobutyl-1H-indol-5-yl)oxy]phenyl}acetic acid Example 275
{3-Bromo-5-chloro-4-[(3-cyclopentyl-1H-indol-5-yl)oxy]phenyl}acetic acid Example 276
{3-Bromo-5-chloro-4-[(3-cyclohexyl-1H-indol-5-yl)oxy]phenyl}acetic acid Example 277
{3-Bromo-5-chloro-4-[(3-propyl-1H-indol-5-yl)oxy]phenyl}acetic acid Example 278
{3-Bromo-4-[(3-butyl-1H-indol-5-yl)oxy]-5-chlorophenyl}acetic acid Example 279
{3-Bromo-5-chloro-4-[(3-pentyl-1H-indol-5-yl)oxy]phenyl}acetic acid Example 280
{3-Bromo-5-chloro-4-[(3-hexyl-1H-indol-5-yl)oxy]phenyl}acetic acid Example 281
{3-Bromo-5-chloro-4-[(3-isobutyl-1H-indol-5-yl)oxy]phenyl}acetic acid Example 282
{3-Bromo-4-[(3-sec-butyl-1H-indol-5-yl)oxy]-5-chlorophenyl}acetic acid Example 283
(3-Bromo-5-chloro-4-{[3-(cyclohexylmethyl)-1H-indol-5-yl]oxy}phenyl)acetic acid Example 284
(3-Bromo-5-chloro-4-{[3-(cyclopentylmethyl)-1H-indol-5-yl]oxy}phenyl)acetic acid Example 285
(3-Bromo-5-chloro-4-{[3-(cyclobutylmethyl)-1H-indol-5-yl]oxy}phenyl)acetic acid Example 286
(3-Bromo-5-chloro-4-{[3-(cyclopropylmethyl)-1H-indol-5-yl]oxy}phenyl)acetic acid Example 287
{4-[(3-Benzyl-1H-indol-5-yl)oxy]-3-bromo-5-chlorophenyl}acetic acid Example 288
(3-Bromo-5-chloro-4-{[3-(4-fluorobenzyl)-1H-indol-5-yl]oxy}phenyl)acetic acid Example 289
(3-Bromo-5-chloro-4-{[3-(4-chlorobenzyl)-1H-indol-5-yl]oxy}phenyl)acetic acid Example 290
[3-Bromo-5-chloro-4-({3-[(4-chlorophenyl)sulphonyl]-1H-indol-5-yl}oxy)phenyl]-acetic acid Example 291
[3-Bromo-5-chloro-4-({3-[(4-fluorophenyl)sulphonyl]-1H-indol-5-yl}oxy)phenyl]-acetic acid Example 292
(3-Bromo-5-chloro-4-{[3-(phenylsulphonyl)-1H-indol-5-yl]oxy}phenyl)acetic acid Example 293
{3-Bromo-4-[(3-isopropyl-1H-indol-5-yl)oxy]-5-methylphenyl}acetic acid Example 294
{3-Bromo-4-[(3-cyclopropyl-1H-indol-5-yl)oxy]-5-methylphenyl}acetic acid Example 295
{3-Bromo-4-[(3-cyclobutyl-1H-indol-5-yl)oxy]-5-methylphenyl}acetic acid Example 296
{3-Bromo-4-[(3-cyclopentyl-1H-indol-5-yl)oxy]-5-methylphenyl}acetic acid Example 297
{3-Bromo-4-[(3-cyclohexyl-1H-indol-5-yl)oxy]-5-methylphenyl}acetic acid Example 298
{3-Bromo-5-methyl-4-[(3-propyl-1H-indol-5-yl)oxy]phenyl}acetic acid Example 299
{3-Bromo-4-[(3-butyl-1H-indol-5-yl)oxy]-5-methylphenyl}acetic acid Example 300
{3-Bromo-5-methyl-4-[(3-pentyl-1H-indol-5-yl)oxy]phenyl}acetic acid Example 301
{3-Bromo-4-[(3-hexyl-1H-indol-5-yl)oxy]-5-methylphenyl}acetic acid Example 302
{3-Bromo-4-[(3-isobutyl-1H-indol-5-yl)oxy]-5-methylphenyl}acetic acid Example 303
{3-Bromo-4-[(3-sec-butyl-1H-indol-5-yl)oxy]-5-methylphenyl}acetic acid Example 304
(3-Bromo-4-{[3-(cyclohexylmethyl)-1H-indol-5-yl]oxy}-5-methylphenyl)acetic acid Example 305
(3-Bromo-4-{[3-(cyclopentylmethyl)-1H-indol-5-yl]oxy}-5-methylphenyl)acetic acid Example 306
(3-Bromo-4-{[3-(cyclobutylmethyl)-1H-indol-5-yl]oxy}-5-methylphenyl)acetic acid Example 307
(3-Bromo-4-{[3-(cyclopropylmethyl)-1H-indol-5-yl]
oxy}-5-methylphenyl)acetic acid Example 308
{4-[(3-benzyl-1H-indol-5-yl)oxy]-3-bromo-5-
methylphenyl}acetic acid Example 309
(3-Bromo-4-{[3-(4-fluorobenzyl)-1H-indol-5-yl]
oxy}-5-methylphenyl)acetic acid Example 310
(3-Bromo-4-{[3-(4-chlorobenzyl)-1H-indol-5-yl]
oxy}-5-methylphenyl)acetic acid Example 311
[3-Bromo-4-({3-[(4-chlorophenyl)sulphonyl]-1H-
indol-5-yl}oxy)-5-methylphenyl]-acetic acid Example 312
[3-Bromo-4-({3-[(4-fluorophenyl)sulphonyl]-1H-
indol-5-yl}oxy)-5-methylphenyl]-acetic acid Example 313
(3-Bromo-5-methyl-4-{[3-(phenylsulphonyl)-1H-
indol-5-yl]oxy}phenyl)acetic acid Example 314
{3-Chloro-4-[(3-isopropyl-1H-indol-5-yl)oxy]-5-
methylphenyl}acetic acid Example 315
{3-Chloro-4-[(3-cyclopropyl-1H-indol-5-yl)oxy]-5-
methylphenyl}acetic acid Example 316
{3-Chloro-4-[(3-cyclobutyl-1H-indol-5-yl)oxy]-5-
methylphenyl}acetic acid Example 317
{3-Chloro-4-[(3-cyclopentyl-1H-indol-5-yl)oxy]-5-
methylphenyl}acetic acid Example 318
{3-Chloro-4-[(3-cyclohexyl-1H-indol-5-yl)oxy]-5-
methylphenyl}acetic acid Example 319
{3-Chloro-5-methyl-4-[(3-propyl-1H-indol-5-yl)
oxy]phenyl}acetic acid Example 320
{4-[(3-Butyl-1H-indol-5-yl)oxy]-3-chloro-5-
methylphenyl}acetic acid Example 321
{3-Chloro-5-methyl-4-[(3-pentyl-1H-indol-5-yl)oxy]
phenyl}acetic acid Example 322
{3-Chloro-4-[(3-hexyl-1H-indol-5-yl)oxy]-5-
methylphenyl}acetic acid Example 323
{3-Chloro-4-[(3-isobutyl-1H-indol-5-yl)oxy]-5-
methylphenyl}acetic acid Example 324
{4-[(3-sec-Butyl-1H-indol-5-yl)oxy]-3-chloro-5-
methylphenyl}acetic acid Example 325
(3-Chloro-4-{[3-(cyclohexylmethyl)-1H-indol-5-yl]
oxy}-5-methylphenyl)acetic acid Example 326
(3-Chloro-4-{[3-(cyclopentylmethyl)-1H-indol-5-yl]
oxy}-5-methylphenyl)acetic acid Example 327
(3-Chloro-4-{[3-(cyclobutylmethyl)-1H-indol-5-yl]
oxy}-5-methylphenyl)acetic acid Example 328
(3-Chloro-4-{[3-(cyclopropylmethyl)-1H-indol-5-yl]
oxy}-5-methylphenyl)acetic acid Example 329
{4-[(3-Benzyl-1H-indol-5-yl)oxy]-3-chloro-5-
methylphenyl}acetic acid Example 330
(3-Chloro-4-{[3-(4-fluorobenzyl)-1H-indol-5-yl]
oxy}-5-methylphenyl)acetic acid Example 331
(3-Chloro-4-{[3-(4-chlorobenzyl)-1H-indol-5-yl]
oxy}-5-methylphenyl)acetic acid Example 332
[3-Chloro-4-({3-[(4-chlorophenyl)sulphonyl]-1H-
indol-5-yl}oxy)-5-methylphenyl]-acetic acid Example 333
[3-Chloro-4-({3-[(4-fluorophenyl)sulphonyl]-H-
indol-5-yl}oxy)-5-methylphenyl]-acetic acid Example 334
(3-Chloro-5-methyl-4-{[3-(phenylsulphonyl)-1H-
indol-5-yl]oxy}phenyl)acetic acid Example 335
[4-[(3-Isopropyl-1H-indol-5-yl)oxy]-3-methyl-5-
(trifluoromethyl)phenyl]acetic acid Example 336
[4-[(3-Cyclopropyl-1H-indol-5-yl)oxy]-3-methyl-5-
(trifluoromethyl)phenyl]acetic acid Example 337
[4-[(3-Cyclobutyl-1H-indol-5-yl)oxy]-3-methyl-5-
(trifluoromethyl)phenyl]acetic acid Example 338
[4-[(3-Cyclopentyl-1H-indol-5-yl)oxy]-3-methyl-5-
(trifluoromethyl)phenyl]acetic acid Example 339
[4-[(3-Cyclohexyl-1H-indol-5-yl)oxy]-3-methyl-5-
(trifluoromethyl)phenyl]acetic acid Example 340
[3-Methyl-4-[(3-propyl-1H-indol-5-yl)oxy]-5-
(trifluoromethyl)phenyl]acetic acid Example 341
[4-[(3-Butyl- H-indol-5-yl)oxy]-3-methyl-5-
(trifluoromethyl)phenyl]acetic acid Example 342
[3-Methyl-4-[(3-pentyl-1H-indol-5-yl)oxy]-5-
(trifluoromethyl)phenyl]acetic acid Example 343
[4-[(3-Hexyl-1H-indol-5-yl)oxy]-3-methyl-5-
(trifluoromethyl)phenyl]acetic acid Example 344
[4-[(3-Isobutyl-1H-indol-5-yl)oxy]-3-methyl-5-
(trifluoromethyl)phenyl]acetic acid Example 345
[4-[(3-sec-Butyl-1H-indol-5-yl)oxy]-3-methyl-5-
(trifluoromethyl)phenyl]acetic acid Example 346
[4-{[3-(Cyclohexylmethyl)-1H-indol-5-yl]oxy}-3-
methyl-5-(trifluoromethyl)phenyl]-acetic acid Example 347
[4-{[3-(Cyclopentylmethyl)-1H-indol-5-yl]oxy}-3-
methyl-5-(trifluoromethyl)-phenyl]-acetic acid Example 348
[4-{[3-(Cyclobutylmethyl)-1H-indol-5-yl]oxy}-3-
methyl-5-(trifluoromethyl)phenyl]-acetic acid Example 349
[4-{[3-(Cyclopropylmethyl)-1H-indol-5-yl]oxy}-3-methyl-5-(trifluoromethyl)-phenyl]-acetic acid Example 350
[4-[(3-Benzyl-1H-indol-5-yl)oxy]-3-methyl-5-(trifluoromethyl)phenyl]acetic acid Example 351
[4-{[3-(4-Fluorobenzyl)-1H-indol-5-yl]oxy}-3-methyl-5-(trifluoromethyl)phenyl]-acetic acid Example 352
[4-{[3-(4-Chlorobenzyl)-1H-indol-5-yl]oxy}-3-methyl-5-(trifluoromethyl)phenyl]-acetic acid Example 353
[4-({3-[(4-Chlorophenyl)sulphonyl]-1H-indol-5-yl}oxy)-3-methyl-5-(trifluoro-methyl)-phenyl]acetic acid Example 354
[4-({3-[(4-Fluorophenyl)sulphonyl]-1H-indol-5-yl}oxy)-3-methyl-5-(trifluoromethyl)-phenyl]acetic acid Example 355
[3-Methyl-4-{[3-(phenylsulphonyl)-1H-indol-5-yl]oxy}-5-(trifluoromethyl)-phenyl]-acetic acid Example 356
[4-[(3-Isopropyl-1H-indol-5-yl)oxy]-3,5-bis(trifluoromethyl)phenyl]acetic acid Example 357
[4-[(3-Cyclopropyl-1H-indol-5-yl)oxy]-3,5-bis(trifluoromethyl)phenyl]acetic acid Example 358
[4-[(3-Cyclobutyl-1H-indol-5-yl)oxy]-3,5-bis(trifluoromethyl)phenyl]acetic acid Example 359
[4-[(3-Cyclopentyl-1H-indol-5-yl)oxy]-3,5-bis(trifluoromethyl)phenyl]acetic acid Example 360
[4-[(3-Cyclohexyl-1H-indol-5-yl)oxy]-3,5-bis(trifluoromethyl)phenyl]acetic acid Example 361
[4-[(3-Propyl-1H-indol-5-yl)oxy]-3,5-bis(trifluoromethyl)phenyl]acetic acid Example 362
[4-[(3-Butyl-1H-indol-5-yl)oxy]-3,5-bis(trifluoromethyl)phenyl]acetic acid Example 363
[4-[(3-Pentyl-1H-indol-5-yl)oxy]-3,5-bis(trifluoromethyl)phenyl]acetic acid Example 364
[4-[(3-Hexyl-1H-indol-5-yl)oxy]-3,5-bis(trifluoromethyl)phenyl]acetic acid Example 365
[4-[(3-Isobutyl-1H-indol-5-yl)oxy]-3,5-bis(trifluoromethyl)phenyl]acetic acid Example 366
[4-[(3-sec-Butyl-1H-indol-5-yl)oxy]-3,5-bis(trifluoromethyl)phenyl]acetic acid Example 367
[4-{[3-(Cyclohexylmethyl)-1H-indol-5-yl]oxy}-3,5-bis(trifluoromethyl)phenyl]-acetic acid Example 368
[4-{[3-(Cyclopentylmethyl)-1H-indol-5-yl]oxy}-3,5-bis(trifluoromethyl)phenyl]-acetic acid Example 369
[4-{[3-(Cyclobutylmethyl)-1H-indol-5-yl]oxy}-3,5-bis(trifluoromethyl)phenyl]-acetic acid Example 370
[4-{[3-(Cyclopropylmethyl)-1H-indol-5-yl]oxy}-3,5-bis(trifluoromethyl)phenyl]-acetic acid Example 371
[4-[(3-Benzyl-1H-indol-5-yl)oxy]-3,5-bis(trifluoromethyl)phenyl]acetic acid Example 372
[4-{[3-(4-Fluorobenzyl)-1H-indol-5-yl]oxy}-3,5-bis(trifluoromethyl)phenyl]acetic acid Example 373
[4-{[3-(4-Chlorobenzyl)-1H-indol-5-yl]oxy}-3,5-bis(trifluoromethyl)phenyl]acetic acid Example 374
[4-({3-[(4-Chlorophenyl)sulphonyl]-1H-indol-5-yl}oxy)-3,5-bis(trifluoromethyl)-phenyl]-acetic acid Example 375
[4-({3-[(4-Fluorophenyl)sulphonyl]-1H-indol-5-yl}oxy)-3,5-bis(trifluoromethyl)-phenyl]-acetic acid Example 376
[4-{[3-(Phenylsulphonyl)-1H-indol-5-yl]oxy}-3,5-bis(trifluoromethyl)phenyl]acetic acid Example 377
{3,5-Dibromo-4-[(3-isopropyl-1H-indol-5-yl)oxy]phenyl}acetic acid Example 378
{3,5-Dibromo-4-[(3-cyclopropyl-1H-indol-5-yl)oxy]phenyl}acetic acid Example 379
{3,5-Dibromo-4-[(3-cyclobutyl-1H-indol-5-yl)oxy]phenyl}acetic acid Example 380
{3,5-Dibromo-4-[(3-cyclopentyl-1H-indol-5-yl)oxy]phenyl}acetic acid Example 381
{3,5-Dibromo-4-[(3-cyclohexyl-1H-indol-5-yl)oxy]phenyl}acetic acid Example 382
{3,5-Dibromo-4-[(3-propyl-1H-indol-5-yl)oxy]phenyl}acetic acid Example 383
{3,5-Dibromo-4-[(3-butyl-1H-indol-5-yl)oxy]phenyl}acetic acid Example 384
{3,5-Dibromo-4-[(3-pentyl-1H-indol-5-yl)oxy]phenyl}acetic acid Example 385
{3,5-Dibromo-4-[(3-hexyl-1H-indol-5-yl)oxy]phenyl}acetic acid Example 386
{3,5-Dibromo-4-[(3-isobutyl-1H-indol-5-yl)oxy]phenyl}acetic acid Example 387
{3,5-Dibromo-4-[(3-sec-butyl-1H-indol-5-yl)oxy]phenyl}acetic acid Example 388
(3,5-Dibromo-4-{[3-(cyclohexylmethyl)-1H-indol-5-yl]oxy}phenyl)acetic acid Example 389
(3,5-Dibromo-4-{[3-(cyclopentylmethyl)-1H-indol-5-yl]oxy}phenyl)acetic acid Example 390
(3,5-Dibromo-4-{[3-(cyclobutylmethyl)-1H-indol-5-yl]oxy}phenyl)acetic acid
Example 391
(3,5-Dibromo-4-{[3-(cyclopropylmethyl)-1H-indol-5-yl]oxy}phenyl)acetic acid
Example 392
{4-[(3-Benzyl-1H-indol-5-yl)oxy]-3,5-dibromophenyl}acetic acid
Example 393
(3,5-Dibromo-4-{[3-(4-fluorobenzyl)-1H-indol-5-yl]oxy}phenyl)acetic acid
Example 394
(3,5-Dibromo-4-{[3-(4-chlorobenzyl)-1H-indol-5-yl]oxy}phenyl)acetic acid
Example 395
[3,5-Dibromo-4-({3-[(4-chlorophenyl)sulphonyl]-1H-indol-5-yl}oxy)phenyl]acetic acid
Example 396
[3,5-Dibromo-4-({3-[(4-fluorophenyl)sulphonyl]-1H-indol-5-yl}oxy)phenyl]acetic acid
Example 397
(3,5-Dibromo-4-{[3-(phenylsulphonyl)-1H-indol-5-yl]oxy}phenyl)acetic acid
Example 398
{3,5-Dichloro-4-[(3-isopropyl-1H-indol-5-yl)oxy]phenyl}acetic acid
Example 399
{3,5-Dichloro-4-[(3-cyclopropyl-1H-indol-5-yl)oxy]phenyl}acetic acid
Example 400
{3,5-Dichloro-4-[(3-cyclobutyl-1H-indol-5-yl)oxy]phenyl}acetic acid
Example 401
{3,5-Dichloro-4-[(3-cyclopentyl-1H-indol-5-yl)oxy]phenyl}acetic acid
Example 402
{3,5-Dichloro-4-[(3-cyclohexyl-1H-indol-5-yl)oxy]phenyl}acetic acid
Example 403
{3,5-Dichloro-4-[(3-propyl-1H-indol-5-yl)oxy]phenyl}acetic acid
Example 404
{4-[(3-Butyl-1H-indol-5-yl)oxy]-3,5-dichlorophenyl}acetic acid
Example 405
{3,5-Dichloro-4-[(3-pentyl-1H-indol-5-yl)oxy]phenyl}acetic acid
Example 406
{3,5-Dichloro-4-[(3-hexyl-1H-indol-5-yl)oxy]phenyl}acetic acid
Example 407
{3,5-Dichloro-4-[(3-isobutyl-1H-indol-5-yl)oxy]phenyl}acetic acid
Example 408
{4-[(3-sec-Butyl-1H-indol-5-yl)oxy]-3,5-dichlorophenyl}acetic acid
Example 409
(3,5-Dichloro-4-{[3-(cyclohexylmethyl)-1H-indol-5-yl]oxy}phenyl)acetic acid
Example 410
(3,5-Dichloro-4-{[3-(cyclopentylmethyl)-1H-indol-5-yl]oxy}phenyl)acetic acid Example 411
(3,5-Dichloro-4-{[3-(cyclobutylmethyl)-1H-indol-5-yl]oxy}phenyl)acetic acid
Example 412
(3,5-Dichloro-4-{[3-(cyclopropylmethyl)-1H-indol-5-yl]oxy}phenyl)acetic acid
Example 413
{4-[(3-Benzyl-1H-indol-5-yl)oxy]-3,5-dichlorophenyl}acetic acid
Example 414
(3,5-Dichloro-4-{[3-(4-fluorobenzyl)-1H-indol-5-yl]oxy}phenyl)acetic acid
Example 415
(3,5-Dichloro-4-{[3-(4-chlorobenzyl)-1H-indol-5-yl]oxy}phenyl)acetic acid
Example 416
[3,5-Dichloro-4-({3-[(4-chlorophenyl)sulphonyl]-1H-indol-5-yl}oxy)phenyl]acetic acid
Example 417
[3,5-Dichloro-4-({3-[(4-fluorophenyl)sulphonyl]-1H-indol-5-yl}oxy)phenyl]acetic acid
Example 418
(3,5-Dichloro-4-{[3-(phenylsulphonyl)-1H-indol-5-yl]oxy}phenyl)acetic acid
Example 419
{4-[(3-Isopropyl-1H-indol-5-yl)oxy]-3,5-dimethylphenyl}acetic acid
Example 420
{4-[(3-Cyclopropyl-1H-indol-5-yl)oxy]-3,5-dimethylphenyl}acetic acid
Example 421
{4-[(3-Cyclobutyl-1H-indol-5-yl)oxy]-3,5-dimethylphenyl}acetic acid
Example 422
{4-[(3-Cyclopentyl-1H-indol-5-yl)oxy]-3,5-dimethylphenyl}acetic acid
Example 423
{4-[(3-Cyclohexyl-1H-indol-5-yl)oxy]-3,5-dimethylphenyl}acetic acid
Example 424
{3,5-Dimethyl-4-[(3-propyl-1H-indol-5-yl)oxy]phenyl}acetic acid
Example 425
{4-[(3-Butyl-1H-indol-5-yl)oxy]-3,5-dimethylphenyl}acetic acid
Example 426
{3,5-Dimethyl-4-[(3-pentyl-1H-indol-5-yl)oxy]phenyl}acetic acid
Example 427
{4-[(3-Hexyl-1H-indol-5-yl)oxy]-3,5-dimethylphenyl}acetic acid
Example 428
{4-[(3-Isobutyl-1H-indol-5-yl)oxy]-3,5-dimethylphenyl}acetic acid
Example 429
{4-[(3-sec-Butyl-1H-indol-5-yl)oxy]-3,5-dimethylphenyl}acetic acid
Example 430
(4-{[3-(Cyclohexylmethyl)-1H-indol-5-yl]oxy}-3,5-dimethylphenyl)acetic acid
Example 431
(4-{[3-(Cyclopentylmethyl)-1H-indol-5-yl]oxy}-3,5-dimethylphenyl)acetic acid Example 432
(4-{[3-(Cyclobutylmethyl)-1H-indol-5-yl]oxy}-3,5-dimethylphenyl)acetic acid
Example 433
(4-{[3-(Cyclopropylmethyl)-1H-indol-5-yl]oxy}-3,5-dimethylphenyl)acetic acid
Example 434
{4-[(3,-Benzyl-1H-indol-5-yl)oxy]-3,5-dimethylphenyl}acetic acid
Example 435
(4-{[3-(4-Fluorobenzyl)-1H-indol-5-yl]oxy}-3,5-dimethylphenyl)acetic acid
Example 436
(4-{[3-(4-chlorobenzyl)-1H-indol-5-yl]oxy}-3,5-dimethylphenyl)acetic acid
Example 437
[4-({3-[(4-Chlorophenyl)sulphonyl]-1H-indol-5-yl}oxy)-3,5-dimethylphenyl]acetic acid
Example 438
[4-({3-[(4-Fluorophenyl)sulphonyl]-1H-indol-5-yl}oxy)-3,5-dimethylphenyl]acetic acid
Example 439
(3,5-Dimethyl-4-{[3-(phenylsulphonyl)-1H-indol-5-yl]oxy}phenyl)acetic acid
Example 440
(3,5-Dimethyl-4-{[3-(phenylsulphonyl)-1H-indol-5-yl]oxy}phenoxy)acetic acid
Example 441
(3,5-Dichloro-4-{[3-(phenylsulphonyl)-1H-indol-5-yl]oxy}phenoxy)acetic acid
Example 442
(3,5-Dibromo-4-{[3-(phenylsulphonyl)-1H-indol-5-yl]oxy}phenoxy)acetic acid
Example 443
[4-{[3-(Phenylsulphonyl)-1H-indol-5-yl]oxy}-3,5-bis(trifluoromethyl)phenoxy]-acetic acid
Example 444
(3,5-Dimethyl-4-{[3-(phenylsulphonyl)-1H-indol-5-yl]oxy}phenyl)acetic acid
Example 445
3,5-Dichloro-4-{[3-(phenylsulphonyl)-1H-indol-5-yl]oxy}phenyl)acetic acid
Example 446
(3,5-Dibromo-4-{[3-(phenylsulphonyl)-1H-indol-5-yl]oxy}phenyl)acetic acid
Example 447
[4-{[3-(Phenylsulphonyl)-1H-indol-5-yl]oxy}-3,5-bis(tri fluoromethyl)phenyl]acetic acid
Example 448
3,5-Dimethyl-O-[3-(phenylsulphonyl)-1H-indol-5-yl]-D-tyrosine
Example 449
3,5-Dichloro-O-[3-(phenylsulphonyl)-1H-indol-5-yl]-D-tyrosine
Example 450
3,5-Dibromo-O-[3-(phenylsulphonyl)-1H-indol-5-yl]-D-tyrosine
Example 451
O-[3-(Phenylsulphonyl)-1H-indol-5-yl]-3,5-bis(trifluoromethyl)-D-tyrosine
Example 452
3,5-Dimethyl-O-[3-(phenylsulphonyl)-1H-indol-5-yl]-L-tyrosine
Example 453
3,5-Dichloro-O-[3-(phenylsulphonyl)-1H-indol-5-yl]-L-tyrosine
Example 454
3,5-Dibromo-O-[3-(phenylsulphonyl)-1H-indol-5-yl]-L-tyrosine
Example 455
O-[3-(phenylsulphonyl)-1H-indol-5-yl]-3,5-bis(trifluoromethyl)-L-tyrosine
Example 456
(3,5-Dimethyl-4-{[3-(phenylsulphonyl)-1H-indol-5-yl]oxy}phenyl)methane-sulphonic acid
Example 457
(3,5-Dichloro-4-{[3-(phenylsulphonyl)-1H-indol-5-yl]oxy}phenyl)methanesulphonic acid
Example 458
(3,5-Dibromo-4-{[3-phenylsulphonyl)-1H-indol-5-yl]oxy}phenyl)methanesulphonic acid
Example 459
[4-{[3-(Phenylsulphonyl)-1H-indol-5-yl]oxy}-3,5-bis(trifluoromethyl)phenyl]-methanesulphonic acid
Example 460
[(3,5-Dimethyl-4-{[3-(phenylsulphonyl)-1H-indol-5-yl]oxy}phenyl)sulphanyl]acetic acid
Example 461
[(3,5-Dichloro-4-{[3-(phenylsulphonyl)-1H-indol-5-yl]oxy}phenyl)sulphanyl]acetic acid
Example 462
[(3,5-Dibromo-4-{[3-(phenylsulphonyl)-1H-indol-5-yl]oxy}phenyl)sulphanyl]acetic acid
Example 463
{[4-{[3-(Phenylsulphonyl)-1H-indol-5-yl]oxy}-3,5-bis(trifluoromethyl)phenyl]-sulphanyl}-acetic acid
Example 464
(2R)-Amino(3,5-dimethyl-4-{[3-(phenylsulphonyl)-1H-indol-5-yl]oxy}phenyl)-ethanoic acid
Example 465
(2R)-Amino(3,5-dichloro-4-{[3-(phenylsulphonyl)-1H-indol-5-yl]oxy}phenyl)-ethanoic acid
Example 466
(2R)-Amino(3,5-dibromo-4-{[3-(phenylsulphonyl)-1H-indol-5-yl]oxy}phenyl)-ethanoic acid
Example 467
(2R)-Amino[4-{[3-(phenylsulphonyl)-1H-indol-5-yl]oxy}-3,5-bis(trifluoromethyl)-phenyl]ethanoic acid
Example 468
(2S)-Amino(3,5-dimethyl-4-{[3-(phenylsulphonyl)-1H-indol-5-yl]oxy}phenyl)-ethanoic acid
Example 469
(2S)-Amino(3,5-dichloro-4-{[3-(phenylsulphonyl)-1H-indol-5-yl]oxy}phenyl)-ethanoic acid
Example 470
(2S)-Amino(3,5-dibromo-4-{[3-(phenylsulphonyl)-1H-indol-5-yl]oxy}phenyl)-ethanoic acid
Example 471
(2S)-Amino[4-{[3-(phenylsulphonyl)-1H-indol-5-yl]oxy}-3,5-bis(trifluoromethyl)-phenyl]ethanoic acid
Example 472
[4-({3-[(4-Fluorophenyl)sulphonyl]-1H-indol-5-yl}oxy)-3,5-dimethylphenoxy]acetic acid
Example 473
[3,5-Dichloro-4-({3-[(4-fluorophenyl)sulphonyl]-1H-indol-5-yl}oxy)phenoxy]acetic acid Example 474
[3,5-Dibromo-4-({3-[(4-fluorophenyl)sulphonyl]-1H-indol-5-yl}oxy)phenoxy]acetic acid Example 475
[4-({3-[(4-Fluorophenyl)sulphonyl]-1H-indol-5-yl}oxy)-3,5-bis(trifluoromethyl)-phenoxy]-acetic acid Example 476
[4-({3-[(4-Fluorophenyl)sulphonyl]-1H-indol-5-yl}oxy)-3,5-dimethylphenyl]acetic acid Example 477
[3,5-Dichloro-4-({3-[(4-fluorophenyl)sulphonyl]-1H-indol-5-yl}oxy)phenyl]acetic acid Example 478
[3,5-Dibromo-4-({3-[(4-fluorophenyl)sulphonyl]-1H-indol-5-yl}oxy)phenyl]acetic acid Example 479
[4-({3-[(4-Fluorophenyl)sulphonyl]-1H-indol-5-yl}oxy)-3,5-bis(trifluoromethyl)-phenyl]-acetic acid Example 480
O-{3-[(4-fluorophenyl)sulphonyl]-1H-indol-5-yl}-3,5-dimethyl-D-tyrosine Example 481
3,5-Dichloro-O-{3-[(4-fluorophenyl)sulphonyl]-1H-indol-5-yl}-D-tyrosine Example 482
3,5-Dibromo-O-{3-[(4-fluorophenyl)sulphonyl]-1H-indol-5-yl}-D-tyrosine Example 483
O-{3-[(4-Fluorophenyl)sulphonyl]-1H-indol-5-yl}-3,5-bis(trifluoromethyl)-D-tyrosine Example 484
O-{3-[(4-Fluorophenyl)sulphonyl]-1H-indol-5-yl}-3,5-dimethyl-L-tyrosine Example 485
3,5-Dichloro-O-{3-[(4-fluorophenyl)sulphonyl]-1H-indol-5-yl}-L-tyrosine Example 486
3,5-Dibromo-O-{3-[(4-fluorophenyl)sulphonyl]-1H-indol-5-yl}-L-tyrosine Example 487
O-{3-[(4-Fluorophenyl)sulphonyl]-1H-indol-5-yl}-3,5-bis(trifluoromethyl)-L-tyrosine Example 488
[4-({3-[(4-Fluorphenyl)sulphonyl]-1H-indol-5-yl}oxy)-3,5-dimethylphenyl]methane-sulphonic acid Example 489
[3,5-Dichloro-4-({3-[(4-fluorophenyl)sulphonyl]-1H-indol-5-yl}oxy)phenyl]-methane-sulphonic acid Example 490
[3,5-Dibromo-4-({3-[(4-fluorophenyl)sulphonyl]-1H-indol-5-yl}oxy)phenyl]-methane-sulphonic acid Example 491
[4-({3-[(4-Fluorophenyl)sulphonyl]-1H-indol-5-yl}oxy)-3,5-bis(trifluoromethyl)-phenyl]-methanesulphonic acid Example 492
{[4-({3-[(4-Fluorophenyl)sulphonyl]-1H-indol-5-yl}oxy)-3,5-dimethylphenyl]-sulphanyl}-acetic acid Example 493
{[3,5-Dichloro-4-({3-[(4-fluorophenyl)sulphonyl]-1H-indol-5-yl}oxy)phenyl]sulphanyl}-acetic acid Example 494
{[3,5-Dibromo-4-({3-[(4-fluorophenyl)sulphonyl]-1H-indol-5-yl}oxy)phenyl]sulphanyl}-acetic acid Example 495
{[4-({3-[(4-Fluorophenyl)sulphonyl]-1H-indol-5-yl}oxy)-3,5-bis(trifluoromethyl)-phenyl]-sulphanyl}acetic acid Example 496
(2R)-Amino[4-({3-[(4-fluorophenyl)sulphonyl]-1H-indol-5-yl}oxy)-3,5-dimethyl-phenyl]-ethanoic acid Example 497
(2R)-Amino[3,5-dichloro-4-({3-[(4-fluorophenyl)sulphonyl]-1H-indol-5-yl}oxy)-phenyl]-ethanoic acid Example 498
(2R)-Amino[3,5-dibromo-4-({3-[(4-fluorophenyl)sulphonyl]-1H-indol-5-yl}oxy)-phenyl]-ethanoic acid Example 499
(2R)-Amino[4-({3-[(4-fluorophenyl)sulphonyl]-1H-indol-5-yl}oxy)-3,5-bis(tri-fluoro-methyl)phenyl]ethanoic acid Example 500
(2S)-Amino[4-({3-[(4-fluorophenyl)sulphonyl]-1H-indol-5-yl}oxy)-3,5-dimethyl-phenyl]-ethanoic acid Example 501
(2S)-Amino[3,5-dichloro-4-({3-[(4-fluorophenyl)sulphonyl]-1H-indol-5-yl}oxy)-phenyl]-ethanoic acid Example 502
(2S)-Amino[3,5-dibromo-4-({3-[(4-fluorophenyl)sulphonyl]-1H-indol-5-yl}oxy)-phenyl]-ethanoic acid Example 503
(2S)-Amino[4-({3-[(4-fluorophenyl)sulphonyl]-1H-indol-5-yl}oxy)-3,5-bis(trifluoro-methyl)phenyl]ethanoic acid Example 504
[4-({3-[(4-Chlorophenyl)sulphonyl]-1H-indol-5-yl}oxy)-3,5-dimethylphenoxy]acetic acid Example 505
[3,5-Dichloro-4-({3-[(4-chlorophenyl)sulphonyl]-1H-indol-5-yl}oxy)phenoxy]acetic acid Example 506
[3,5-Dibromo-4-({3-[(4-chlorophenyl)sulphonyl]-1H-indol-5-yl}oxy)phenoxy]acetic acid Example 507
[4-({3-[(4-Chlorophenyl)sulphonyl]-1H-indol-5-yl}oxy)-3,5-bis(trifluoromethyl)-phenoxy]-acetic acid Example 508
[4-({3-[(4-Chlorophenyl)sulphonyl]-1H-indol-5-yl}oxy)-3,5-dimethylphenyl]acetic acid Example 509
[3,5-Dichloro-4-({3-[(4-chlorophenyl)sulphonyl]-1H-indol-5-yl}oxy)phenyl]acetic acid Example 510
[3,5-Dibromo-4-({3-[(4-chlorophenyl)sulphonyl]-1H-indol-5-yl}oxy)phenyl]acetic acid Example 511
[4-({3-[(4-Chlorophenyl)sulphonyl]-1H-indol-5-yl}oxy)-3,5-bis(trifluoromethyl)-phenyl]-acetic acid Example 512
O-{3-[(4-chlorophenyl)sulphonyl]-1H-indol-5-yl}-3,5-dimethyl-D-tyrosine Example 513
3,5-Dichloro-O-{3-[(4-chlorophenyl)sulphonyl]-1H-indol-5-yl}-D-tyrosine Example 514
3,5-Dibromo-O-{3-[(4-chlorophenyl)sulphonyl]-1H-indol-5-yl}-D-tyrosine Example 515
O-{3-[(4-Chlorophenyl)sulphonyl]-1H-indol-5-yl}-3,5-bis(trifluoromethyl)-D-tyrosine Example 516
O-{3-[(4-Chlorophenyl)sulphonyl]-1H-indol-5-yl}-3,5-dimethyl-L-tyrosine Example 517
3,5-Dichloro-O-{3-[(4-chlorophenyl)sulphonyl]-1H-indol-5-yl}-L-tyrosine Example 518
3,5-Dibromo-O-{3-[(4-chlorophenyl)sulphonyl]-1H-indol-5-yl}-L-tyrosine Example 519
O-{3-[(4-Chlorophenyl)sulphonyl]-1H-indol-5-yl}-3,5-bis(trifluoromethyl)-L-tyrosine Example 520
[4-({3-[(4–Clorophenyl)sulphonyl]-1H-indol-5-yl}oxy)-3,5-dimethylphenyl]-methane-sulphonic acid Example 521
[3,5-Dichloro-4-({3-[(4-chlorophenyl)sulphonyl]-1H-indol-5-yl}oxy)phenyl]-methane-sulphonic acid Example 522
[3,5-Dibromo-4-({3-[(4-chlorophenyl)sulphonyl]-1H-indol-5-yl}oxy)phenyl]-methane-sulphonic acid Example 523
[4-({3-[(4-Chlorophenyl)sulphonyl]-1H-indol-5-yl}oxy)-3,5-bis(trifluoromethyl)-phenyl]-methanesulphonic acid Example 524
{[4-({3-[(4-Chlorophenyl)sulphonyl]-1H-indol-5-yl}oxy)-3,5-dimethylphenyl]-sulphanyl}-acetic acid Example 525
{[3,5-Dichloro-4-({3-[(4-chlorophenyl)sulphonyl]-1H-indol-5-yl}oxy)phenyl]sulphanyl}-acetic acid Example 526
{[3,5-Dibromo-4-({3-[(4-chlorophenyl)sulphonyl]-1H-indol-5-yl}oxy)phenyl]sulphanyl}-acetic acid Example 527
{[4-({3-[(4-Chlorophenyl)sulphonyl]-1H-indol-5-yl}oxy)-3,5-bis(trifluoromethyl)-phenyl]-sulphanyl}acetic acid Example 528
(2R)-Amino[4-({3-[(4-chlorophenyl)sulphonyl]-1H-indol-5-yl}oxy)-3,5-dimethyl-phenyl]ethanoic acid Example 529
(2R)-Amino[3,5-dichloro-4-({3-[(4-chlorophenyl)sulphonyl]-1H-indol-5-yl}oxy)-phenyl]ethanoic acid Example 530
(2R)-Amino[3,5-dibromo-4-({3-[(4-chlorophenyl)sulphonyl]-1H-indol-5-yl}oxy)-phenyl]ethanoic acid Example 531
(2R)-Amino[4-({3-[(4-chlorophenyl)sulphonyl]-1H-indol-5-yl}oxy)-3,5-bis(trifluoro-methyl)phenyl]ethanoic acid Example 532
(2S)-Amino[4-({3-[(4-chlorophenyl)sulphonyl]-1H-indol-5-yl}oxy)-3,5-dimethyl-phenyl]ethanoic acid Example 533
(2S)-Amino[3,5-dichloro-4-({3-[(4-chlorophenyl)sulphonyl]-1H-indol-5-yl}oxy)-phenyl]ethanoic acid Example 534
(2S)-Amino[3,5-dibromo-4-({3-[(4-chlorophenyl)sulphonyl]-1H-indol-5-yl}oxy)-phenyl]ethanoic acid Example 535
(2S)-Amino[4-({3-[(4-chlorophenyl)sulphonyl]-1H-indol-5-yl}oxy)-3,5-bis(tri-fluoro-methyl)phenyl]ethanoic acid Example 536
[3,5-Dimethyl-4-({3-[(4-methylphenyl)sulphonyl]-1H-indol-5-yl}oxy)phenoxy]-acetic acid Example 537
[3,5-Dichloro-4-({3-[(4-methylphenyl)sulphonyl]-1H-indol-5-yl}oxy)phenoxy]acetic acid Example 538
[3,5-Dibromo-4-({3-[(4-methylphenyl)sulphonyl]-1H-indol-5-yl}oxy)phenoxy]acetic acid Example 539
[4-({3-[(4-Methylphenyl)sulphonyl]-1H-indol-5-yl}oxy)-3,5-bis(trifluoromethyl)-phenoxy]acetic acid Example 540
[3,5-Dimethyl-4-({3-[(4-methylphenyl)sulphonyl]-1H-indol-5-yl}oxy)phenyl]acetic acid Example 541
[3,5-Dichloro-4-({3-[(4-methylphenyl)sulphonyl]-1H-indol-5-yl}oxy)phenyl]acetic acid Example 542
[3,5-Dibromo-4-({3-[(4-methylphenyl)sulphonyl]-1H-indol-5-yl}oxy)phenyl]acetic acid Example 543
[4-({3-[(4-Methylphenyl)sulphonyl]-1H-indol-5-yl}oxy)-3,5-bis(trifluoromethyl)-phenyl]-acetic acid Example 544
3,5-Dimethyl-O-{3-[(4-methylphenyl)sulphonyl]-1H-indol-5-yl}-D-tyrosine Example 545
3,5-Dichloro-O-{3-[(4-methylphenyl)sulphonyl]-1H-indol-5-yl}-D-tyrosine Example 546
3,5-Dibromo-O-{3-[(4-methylphenyl)sulphonyl]-1H-indol-5-yl}-D-tyrosine Example 547
O-{3-[(4-methylphenyl)sulphonyl]-1H-indol-5-yl}-3,5-bis(trifluoromethyl)-D-tyrosine Example 548
3,5-Dimethyl-O-{3-[(4-methylphenyl)sulphonyl]-1H-indol-5-yl}-L-tyrosine Example 549
3,5-Dichloro-O-{3-[(4-methylphenyl)sulphonyl]-1H-indol-5-yl}-L-tyrosine Example 550
3,5-Dibromo-O-{3-[(4-methylphenyl)sulphonyl]-H-indol-5-yl}-L-tyrosine

Example 551

O-{3-[(4-Methylphenyl)sulphonyl]-1H-indol-5-yl}-3,5-bis(trifluoromethyl)-L-tyrosine

Example 552

[3,5-Dimethyl-4-({3-[(4-methylphenyl)sulphonyl]-1H-indol-5-yl}oxy)phenyl]-methane-sulphonic acid

Example 553

[3,5-Dichloro-4-({3-[(4-methylphenyl)sulphonyl]-1H-indol-5-yl}oxy)phenyl]-methane-sulphonic acid

Example 554

[3,5-Dibromo-4-({3-[(4-methylphenyl)sulphonyl]-1H-indol-5-yl }oxy)phenyl]-methane-sulphonic acid

Example 555

[4-({3-[(4-Methylphenyl)sulphonyl]-1H-indol-5-yl}oxy)-3,5-bis(trifluoromethyl)-phenyl]-methanesulphonic acid

Example 556

{[3,5-Dimethyl-4-({3-[(4-methylphenyl)sulphonyl]-1H-indol-5-yl}oxy)phenyl]-sulphanyl}acetic acid

Example 557

{[3,5-Dichloro-4-({3-[(4-methylphenyl)sulphonyl]-1H-indol-5-yl}oxy)phenyl]-sulphanyl}-acetic acid

Example 558

{[3,5-Dibromo-4-({3-[(4-methylphenyl)sulphonyl]-1H-indol-5-yl}oxy)phenyl]-sulphanyl}-acetic acid

Example 559

{[4-({3-[(4-Methylphenyl)sulphonyl]-1H-indol-5-yl}oxy)-3,5-bis(trifluoromethyl)-phenyl]sulphanyl}acetic acid

Example 560

(2R)-Amino[3,5-dimethyl-4-({3-[(4-methylphenyl)sulphonyl]-1H-indol-5-yl}oxy)-phenyl]ethanoic acid

Example 561

(2R)-Amino[3,5-dichloro-4-({3-[(4-methylphenyl)sulphonyl]-1H-indol-5-yl}oxy)-phenyl]ethanoic acid

Example 562

(2R)-Amino [3,5-dibromo-4-({3-[(4-methylphenyl)sulphonyl]-1H-indol-5-yl}oxy)-phenyl]ethanoic acid

Example 563

(2R)-Amino[4-({3-[(4-methylphenyl)sulphonyl]-1H-indol-5-yl}oxy)-3,5-bis(trifluoro-methyl)phenyl]ethanoic acid

Example 564

(2S)-Amino[3,5-dimethyl-4-({3-[(4-methylphenyl)sulphonyl]-1H-indol-5-yl}oxy)-phenyl]ethanoic acid

Example 565

(2S)-Amino[3,5-dichloro-4-({3-[(4-methylphenyl)sulphonyl]-1H-indol-5-yl}oxy)-phenyl]-ethanoic acid

Example 566

(2S)-Amino[3,5-dibromo-4-({3-[(4-methylphenyl)sulphonyl]-1H-indol-5-yl}oxy)-phenyl]ethanoic acid

Example 567

(2S)-Amino[4-({3-[(4-methylphenyl)sulphonyl]-1H-indol-5-yl}oxy)-3,5-bis(tri-fluoro-methyl)phenyl]ethanoic acid

Example 568

(3,5-Dimethyl-4-{[3-(4-pyridinylsulphonyl)-1H-indol-5-yl]oxy}phenoxy)acetic acid

Example 569

(3,5-Dichloro-4-{[3-(4-pyridinylsulphonyl)-1H-indol-5-yl]oxy}phenoxy)acetic acid

Example 570

(3,5-Dibromo-4-{[3-(4-pyridinylsulphonyl)-1H-indol-5-yl]oxy}phenoxy)acetic acid

Example 571

[4-{[3-(4-Pyridinylsulphonyl)-1H-indol-5-yl]oxy}-3,5-bis(trifluoromethyl)phenoxy]-acetic acid

Example 572

(3,5-Dimethyl-4-{[3-(4-pyridinylsulphonyl)-1H-indol-5-yl]oxy}phenyl)acetic acid

Example 573

(3,5-Dichloro-4-{[3-(4-pyridinylsulphonyl)-1H-indol-5-yl]oxy}phenyl)acetic acid

Example 574

(3,5-Dibromo-4-{[3-(4-pyridinylsulphonyl)-1H-indol-5-yl]oxy}phenyl)acetic acid

Example 575

[4-{[3-(4-Pyridinylsulphonyl)-1H-indol-5-yl]oxy}-3,5-bis(trifluoromethyl)phenyl]-acetic acid

Example 576

3,5-Dimethyl-O-[3-(4-pyridinylsulphonyl)-1H-indol-5-yl]-D-tyrosine

Example 577

3,5-Dichloro-O-[3-(4-pyridinylsulphonyl)-1H-indol-5-yl]-D-tyrosine

Example 578

3,5-Dibromo-O-[3-(4-pyridinylsulphonyl)-1H-indol-5-yl]-D-tyrosine

Example 579

O-[3-(4-Pyridinylsulphonyl)-1H-indol-5-yl]-3,5-bis(trifluoromethyl)-D-tyrosine

Example 580

3,5-Dimethyl-O-[3-(4-pyridinylsulphonyl)-1H-indol-5-yl]-L-tyrosine

Example 581

3,5-Dichloro-O-[3-(4-pyridinylsulphonyl)-1H-indol-5-yl]-L-tyrosine

Example 582

3,5-Dibromo-O-[3-(4-pyridinylsulphonyl)-1H-indol-5-yl]-L-tyrosine

Example 583

O-[3-(4-Pyridinylsulphonyl)-1H-indol-5-yl]-3,5-bis(trifluoromethyl)-L-tyrosine

Example 584

(3,5-Dimethyl-4-{[3-(4-pyridinylsulphonyl)-1H-indol-5-yl]oxy}phenyl)methane-sulphonic acid

Example 585

(3,5-Dichloro-4-{[3-(4-pyridinylsulphonyl)-1H-indol-5-yl]oxy}phenyl)methane-sulphonic acid

Example 586

(3,5-Dibromo-4-{[3-(4-pyridinylsulphonyl)-1H-indol-5-yl]oxy}phenyl)methane-sulphonic acid

Example 587

[4-{[3-(4-Pyridinylsulphonyl)-1H-indol-5-yl]oxy}-3,5-bis(trifluoromethyl)phenyl]methanesulphonic acid

Example 588

[(3,5-Dimethyl-4-{[3-(4-pyridinylsulphonyl)-1H-indol-5-yl]oxy}phenyl)sulphanyl]-acetic acid

Example 589

[(3,5-Dichloro-4-{[3-(4-pyridinylsulphonyl)-1H-indol-5yl]oxy}phenyl)sulphanyl]-acetic acid

Example 590

[(3,5-Dibromo-4-{[3-(4-pyridinylsulphonyl)-1H-indol-5-yl]oxy}phenyl)sulphanyl]-acetic acid

Example 591

{[4-{[3-(4-Pyridinylsulphonyl)-1H-indol-5-yl]oxy}-3,5-bis(trifluoromethyl)phenyl]-sulphanyl}acetic acid

EXAMPLE 592

(2R)-Amino(3,5-dimethyl-4-{[3-(4-pyridinylsulphonyl)-1H-indol-5-yl]oxy}phenyl)-ethanoic acid

Example 593

(2R)-Amino(3,5-dichloro-4-{[3-(4-pyridinylsulphonyl)-1H-indol-5-yl]oxy}phenyl)-ethanoic acid

Example 594

(2R)-Amino(3,5-dibromo-4-{[3-(4-pyridinylsulphonyl)-1H-indol-5-yl]oxy}phenyl)-ethanoic acid

Example 595

(2R)-Amino[4-{[3-(4-pyridinylsulphonyl)-1H-indol-5-yl]oxy}-3,5-bis(trifluoro-methyl)-phenyl]ethanoic acid

Example 596

(2S)-Amino(3,5-dimethyl-4-{[3-(4-pyridinylsulphonyl)-1H-indol-5-yl]oxy}phenyl)-ethanoic acid

Example 597

(2S)-Amino(3,5-dichloro-4-{[3-(4-pyridinylsulphonyl)-1H-indol-5-yl]oxy}phenyl)-ethanoic acid

Example 598

(2S)-Amino(3,5-dibromo-4-{[3-(4-pyridinylsulphonyl)-1H-indol-5-yl]oxy}phenyl)-ethanoic acid

Example 599

(2S)-Amino[4-{[3-(4-pyridinylsulphonyl)-1H-indol-5-yl]oxy}-3,5-bis(trifluoro-methyl).-phenyl]ethanoic acid

Example 600

[4-({3-[(4-Methoxyphenyl)sulphonyl]-1H-indol-5-yl}oxy)-3,5-dimethylphenoxy]-acetic acid

Example 601

[3,5-Dichloro-4-({3-[(4-methoxyphenyl)sulphonyl]-1H-indol-5-yl}oxy)phenoxy]-acetic acid

Example 602

[3,5-Dibromo-4-({3-[(4-methoxyphenyl)sulphonyl]-1H-indol-5-yl}oxy)phenoxy]-acetic acid

Example 603

[4-({3-[(4-Methoxyphenyl)sulphonyl]- H-indol-5-yl}oxy)-3,5-bis(trifluoromethyl)-phenoxy]acetic acid

Example 604

[4-({3-[(4-Methoxyphenyl)sulphonyl]-1H-indol-5-yl}oxy)-3,5-dimethylphenyl]-acetic acid

Example 605

[3,5-Dichloro-4-({$^3$-[(4-methoxyphenyl)sulphonyl]-1H-indol-5-yl}oxy)phenyl]acetic acid

Example 606

[3,5-Dibromo-4-({3-[(4-methoxyphenyl)sulphonyl]-1H-indol-5-yl}oxy)phenyl]acetic acid Example 607
[4-({3-[(4-Methoxyphenyl)sulphonyl]-1H-indol-5-yl}oxy)-3,5-bis(trifluoromethyl)-phenyl]acetic acid Example 608
O-{3-[(4-Methoxyphenyl)sulphonyl]-1H-indol-5-yl}-3,5-dimethyl-D-tyrosine Example 609
3,5-Dichloro-O-{3-[(4-methoxyphenyl)sulphonyl]-1H-indol-5-yl}-D-tyrosine Example 610
3,5-Dibromo-O-{3-[(4-methoxyphenyl)sulphonyl]-1H-indol-5-yl}-D-tyrosine Example 611
O-{3-[(4-methoxyphenyl)sulphonyl]-1H-indol-5-yl}-3,5-bis(trifluoromethyl)-D-tyrosine Example 612
O-{3-[(4-methoxyphenyl)sulphonyl]-1H-indol-5-yl3–3,5-dimethyl-L-tyrosine Example 613
3,5-Dichloro-O-{3-[(4-methoxyphenyl)sulphonyl]-1H-indol-5-yl}-L-tyrosine Example 614
3,5-Dibromo-O-{3-[(4-methoxyphenyl)sulphonyl]-1H-indol-5-yl}-L-tyrosine Example 615
O-{3-[(4-Methoxyphenyl)sulphonyl]-1H-indol-5-yl}-3,5-bis(trifluoromethyl)-L-tyrosine Example 616
[4-({3-[(4-Methoxyphenyl)sulphonyl]-1H-indol-5-yl}oxy)-3,5-dimethylphenyl]-methane-sulphonic acid Example 617
[3,5-Dichloro-4-({3-[(4-methoxyphenyl)sulphonyl]-1H-indol-5-yl}oxy)phenyl]-methane-sulphonic acid Example 618
[3,5-Dibromo-4-({3-[(4-methoxyphenyl)sulphonyl]-1H-indol-5-yl}oxy)phenyl]-methane- sulphonic acid Example 619
[4-({3-[(4-Methoxyphenyl)sulphonyl]-1H-indol-5-yl}oxy)-3,5-bis(trifluoromethyl)-phenyl]methanesulphonic acid Example 620
{[4-({3-[(4-Methoxyphenyl)sulphonyl]-1H-indol-5-yl}oxy)-3,5-dimethylphenyl]-sulphanyl}acetic acid Example 621
{[3,5-Dichloro-4-({3-[(4-methoxyphenyl)sulphonyl]-1H-indol-5-yl}oxy)phenyl]-sulphanyl}acetic acid Example 622
{[3,5-Dibromo-4-({3-[(4-methoxyphenyl)sulphonyl]-1H-indol-5-yl}oxy)phenyl]-sulphanyl}acetic acid Example 623
{[4-({3-[(4-Methoxyphenyl)sulphonyl]-1H-indol-5-yl}oxy)-3,5-bis(trifluoromethyl)-phenyl]sulphanyl}acetic acid Example 624
(2R)-Amino[4-({3-[(4-methoxyphenyl)sulphonyl]-1H-indol-5-yl}oxy)-3,5-dimethyl-phenyl]ethanoic acid Example 625
(2R)-Amino[3,5-dichloro-4-({3-[(4-methoxyphenyl)sulphonyl]-1H-indol-5-yl}oxy)-phenyl]ethanoic acid Example 626
(2R)-Amino[3,5-dibromo-4-({3-[(4-methoxyphenyl)sulphonyl]-1H-indol-5-yl}oxy)-phenyl]ethanoic acid Example 627
(2R)-Amino[4-({3-[(4-methoxyphenyl)sulphonyl]-1H-indol-5-yl}oxy)-3,5-bis(tri-fluoro-methyl)phenyl]ethanoic acid Example 628
(2S)-Amino[4-({3-[(4-methoxyphenyl)sulphonyl]-1H-indol-5-yl}oxy)-3,5-dimethyl-phenyl]ethanoic acid Example 629
(2S)-Amino[3,5-dichloro-4-({3-[(4-methoxyphenyl)sulphonyl]-1H-indol-5-yl}oxy)-phenyl]ethanoic acid Example 630
(2S)-Amino[3,5-dibromo-4-({3-[(4-methoxyphenyl)sulphonyl]-1H-indol-5-yl}oxy)-phenyl]ethanoic acid Example 631
(2S)-Amino[4-({3-[(4-methoxyphenyl)sulphonyl]-1H-indol-5-yl}oxy)-3,5-bis(tri-fluoro-methyl)phenyl]ethanoic acid Example 632
{3,5-Dimethyl-4-[(3-{[4-(trifluoromethyl)phenyl]sulphonyl}-1H-indol-5-yl)oxy]-phenoxy}acetic acid Example 633
{3,5-Dichloro-4-[(3-{[4-(trifluoromethyl)phenyl]sulphonyl}-1H-indol-5-yl)oxy]-phenoxy}acetic acid Example 634
{3,5-Dibromo-4-[(3-{[4-(trifluoromethyl)phenyl]sulphonyl}-1H-indol-5-yl)oxy]-phenoxy}acetic acid Example 635
{3,5-Bis(trifluoromethyl)-4-[(3-{[4-(trifluoromethyl)phenyl]sulphonyl}-1H-indol-5-yl]oxy}-phenoxy}acetic acid Example 636
{3,5-Dimethyl-4-[(3-{[4-(trifluoromethyl)phenyl]sulphonyl}-1H-indol-5-yl)oxy]-phenyl}acetic acid Example 637
{3,5-Dichloro-4-[(3-{[4-(trifluoromethyl)phenyl]sulphonyl}-1H-indol-5-yl)oxy]-phenyl}-acetic acid Example 638
{3,5-Dibromo-4-[(3-{[4-(trifluoromethyl)phenyl]sulphonyl}-1H-indol-5-yl)oxy]-phenyl}-acetic acid Example 639
{3,5-Bis(trifluoromethyl)-4-[(3-{[4-(trifluoromethyl)phenyl]sulphonyl}-1H-indol-5-yl)oxy]-phenyl}acetic acid Example 640
3,5-Dimethyl-O-(3-{[4-(trifluoromethyl)phenyl]sulphonyl}-1H-indol-5-yl)-D-tyrosine Example 641
3,5-Dichloro-O-(3-{[4-(trifluoromethyl)phenyl]sulphonyl}-1H-indol-5-yl)-D-tyrosine

Example 642
3,5-Dibromo-O-(3-{[4-(trifluoromethyl)phenyl]sulphonyl}-1H-indol-5-yl)-D-tyrosine

Example 643
3,5-Bis(trifluoromethyl)-O-(3-{[4-(trifluoromethyl)phenyl]sulphonyl}-1H-indol-5-yl)-D-tyrosine

Example 644
3,5-Dimethyl-O-(3-{[4-(trifluoromethyl)phenyl]sulphonyl}-1H-indol-5-yl)-L-tyrosine

Example 645
3,5-Dichloro-O-(3-{[4-(trifluoromethyl)phenyl]sulphonyl}-1H-indol-5-yl)-L-tyrosine

Example 646
3,5-Dibromo-O-(3-{[4-(trifluoromethyl)phenyl]sulphonyl}-1H-indol-5-yl)-L-tyrosine

Example 647
3,5-Bis(trifluoromethyl)-O-(3-{[4-(trifluoromethyl)phenyl]sulphonyl}-1H-indol-5-yl)-L-tyrosine

Example 648
{3,5-Dimethyl-4-[(3-{[4-(trifluoromethyl)phenyl]sulphonyl}-1H-indol-5-yl)oxy]-phenyl}-methanesulphonic acid

Example 649
{3,5-Dichloro-4-[(3-{[4-(trifluoromethyl)phenyl]sulphonyl}-1H-indol-5-yl)oxy]-phenyl}-methanesulphonic acid

Example 650
{3,5-Dibromo-4-[(3-{[4-(trifluoromethyl)phenyl]sulphonyl}-1H-indol-5-yl)oxy]-phenyl}-methanesulphonic acid

Example 651
{3,5-Bis(trifluoromethyl)-4-[(3-{[4-(trifluoromethyl)phenyl]sulphonyl}-1H-indol-5-yl)oxy]phenyl}methanesulphonic acid

Example 652
({3,5-Dimethyl-4-[(3-{[4-(trifluoromethyl)phenyl]sulphonyl}-1H-indol-5-yl)oxy]-phenyl}sulphanyl)acetic acid

Example 653
({3,5-Dichloro-4-[(3-{[4-(trifluoromethyl)phenyl]sulphonyl}-1H-indol-5-yl)oxy]-phenyl sulphanyl)acetic acid

Example 654
({3,5-Dibromo-4-[(3-{[4-(trifluoromethyl)phenyl]sulphonyl}-1H-indol-5-yl)oxy]-phenyl}sulphanyl)acetic acid

Example 655
({3,5-Bis(trifluoromethyl)-4-[(3-{[4-(trifluoromethyl)phenyl]sulphonyl}-1H-indol-5-yl]oxy}-phenyl}sulphanyl)acetic acid

Example 656
(2R)-Amino{3,5-dimethyl-4-[(3-{[4-(trifluoromethyl)phenyl]sulphonyl}-1H-indol-5-yl)oxy]phenyl}ethanoic acid

Example 657
(2R)-Amino{3,5-dichloro-4-[(3-{[4-(trifluoromethyl)phenyl]sulphonyl}-1H-indol-5-yl)oxy]phenyl}ethanoic acid

Example 658
(2R)-Amino{3,5-dibromo-4-[(3-{[4-(trifluoromethyl)phenyl]sulphonyl}-1H-indol-5-yl)oxy]phenyl}ethanoic acid

Example 659
(2R)-Amino{3,5-bis(trifluoromethyl)-4-[(3-{[4-(trifluoromethyl)phenyl]sulphonyl}-1H-indol-5-yl)oxy]phenyl}ethanoic acid

Example 660
(2S)-Amino{3,5-dimethyl-4-[(3-{[4-(trifluoromethyl)phenyl]sulphonyl}-1H-indol-5-yl)oxy]phenyl}ethanoic acid

Example 661
(2S)-Amino{3,5-dichloro-4-[(3-{[4-(trifluoromethyl)phenyl]sulphonyl}-1H-indol-5-yl)oxy]phenyl}ethanoic acid

Example 662
(2S)-Amino {3,5-dibromo-4-[(3-{[4-(trifluoromethyl)phenyl]sulphonyl}-1H-indol-5-yl)oxy]phenyl}ethanoic acid

Example 663
(2S)-Amino{3,5-bis(trifluoromethyl)-4-[(3-{[4-(trifluoromethyl)phenyl]sulphonyl}-1H-indol-5-yl)oxy]phenyl}ethanoic acid

Example 664
Difluoro(4-{[3-(4-fluorobenzyl)-1H-indol-5-yl)oxy]-3,5-dimethylphenyl)acetic acid

Example 665
(4-{[3-(4-Chlorobenzyl)-1H-indol-5-yl]oxy}-3,5-dimethylphenyl)(difluoro)acetic acid

Example 666
[4-({3-[(4-Chlorophenyl)sulphonyl]-1H-indol-5-yl}oxy)-3,5-dimethylphenyl]-(difluoro)-acetic acid

Example 667
Difluoro[4-({3-[(4-fluorophenyl)sulphonyl]-1H-indol-5-yl}oxy)-3,5-dimethyl-phenyl]-acetic acid

Example 668
Fluoro[4-({3-[(4-fluorophenyl)sulphonyl]-1H-indol-5-yl}oxy)-3,5-dimethylphenyl]acetic acid

Example 669
[4-({3-[(4-Chlorophenyl)sulphonyl]-1H-indol-5-yl}oxy)-3,5-dimethylphenyl]-(fluoro)-acetic acid

Example 670
(4-{[3-(4-Chlorobenzyl)-1H-indol-5-yl]oxy}-3,5-dimethylphenyl)(fluoro)acetic acid

Example 671
Fluoro(4-{[3-(4-fluorobenzyl)-1H-indol-5-yl]oxy}-3,5-dimethylphenyl)acetic acid

Example 672
(3-Chloro-4-{[3-(4-fluorobenzyl)-1H-indol-5-yl]oxy}-5-methylphenyl)(fluoro)acetic acid

Example 673
(3-Chloro-4-{[3-(4-chlorobenzyl)-1H-indol-5-yl]oxy}-5-methylphenyl)(fluoro)aceti acid

Example 674
[3-Chloro-4-({3-[(4-chlorophenyl)sulphonyl]-1H-indol-5-yl}oxy)-5-methylphenyl]-(fluoro)-acetic acid Example 675
3-Chloro-4-({3-[(4-fluorophenyl)sulphonyl]-1H-indol-5-yl}oxy)-5-methylphenyl]-(fluoro)-acetic acid Example 676
[3-Chloro-4-({3-[(4-fluorophenyl)sulphonyl]-1H-indol-5-yl}oxy)-5-methylphenyl]-(difluoro)acetic acid Example 677
[3-Chloro-4-({3-[(4-chlorophenyl)sulphonyl]-1H-indol-5-yl}oxy)-5-methylphenyl]-(difluoro)acetic acid Example 678
(3-Chloro-4-{[3-(4-chlorobenzyl)-1l-indol-5-yl]oxy}-5-methylphenyl)(difluoro)-acetic acid Example 679
(3-Chloro-4-{[3-(4-fluorobenzyl)-1H-indol-5-yl]oxy}-5-methylphenyl)(difluoro)-acetic acid Example 680
(3,5-Dichloro-4-{[3-(4-fluorobenzyl)-1H-indol-5-yl]oxy}phenyl)(difluoro)acetic acid Example 681
(3,5-Dichloro-4-{[3-(4-chlorobenzyl)-1H-indol-5-yl]oxy}phenyl)(difluoro)acetic acid Example 682
[3,5-Dichloro-4-({3-[(4-chlorophenyl)sulphonyl]-1H-indol-5-yl}oxy)phenyl]-(difluoro)-acetic acid Example 683
[3,5-Dichloro-4-({3-[(4-fluorophenyl)sulphonyl]-1H-indol-5-yl}oxy)phenyl]-(difluoro)-acetic acid Example 684
[3,5-Dichloro-4-({3-[(4-fluorophenyl)sulphonyl]-1H-indol-5-yl}oxy)phenyl](fluoro acetic acid Example 685
[3,5-Dichloro-4-({3-[(4-chlorophenyl)sulphonyl]-1H-indol-5-yl}oxy)phenyl](fluoro)-acetic acid Example 686
(3,5-Dichloro-4-{[3-(4-chlorobenzyl)-1H-indol-5-yl]oxy}phenyl)(fluoro)acetic acid Example 687
(3,5-Dichloro-4-[3-(4-fluorobenzyl)-1H-indol-5-yl]oxy}phenyl)(fluoro)acetic acid Example 688
(3,5-Dibromo-4-{[3-(4-fluorobenzyl)-1H-indol-5-yl]oxy}phenyl)(fluoro)acetic acid Example 689
(3,5-Dibromo-4-{[3-(4-chlorobenzyl)-1H-indol-5-yl]oxy}phenyl)(fluoro)acetic acid Example 690
[3,5-Dibromo-4-({3-[(4-chlorophenyl)sulphonyl]-1H-indol-5-yl}oxy)phenyl]-(fluoro)-acetic acid Example 691
[3,5-Dibromo-4-({3-[(4-fluorophenyl)sulphonyl]-1H-indol-5-yl}oxy)phenyl](fluoro)-acetic acid Example 692
[3,5-Dibromo-4-({3-[(4-fluorophenyl)sulphonyl]-1H-indol-5-yl}oxy)phenyl]-(difluoro)-acetic acid Example 693
[3,5-Dibromo-4-({3-[(4-chlorophenyl)sulphonyl]-1H-indol-5-yl}oxy)phenyl]-(difluoro)-acetic acid Example 694
(3,5-Dibromo-4-{[3-(4-chlorobenzyl)-1H-indol-5-yl]oxy}phenyl)(difluoro)acetic acid Example 695
(3,5-Dibromo-4-{[3-(4-fluorobenzyl)-1H-indol-5-yl]oxy}phenyl)(difluoro)acetic acid Example 696
Difluoro[4-{[3-(4-fluorobenzyl)-1H-indol-5-yl]oxy}-3,5-bis(trifluoromethyl)phenyl]-acetic acid Example 697
[4-{[3-(4-Chlorobenzyl)-1H-indol-5-yl]oxy}-3,5-bis(trifluoromethyl)phenyl]-(difluoro)-acetic acid Example 698
[4-({3-[(4-Chlorophenyl)sulphonyl]-1H-indol-5-yl}oxy)-3,5-bis(trifluoromethyl)-phenyl]-(difluoro) acetic acid Example 699
Difluoro[4-({3-[(4-fluorophenyl)sulphonyl]-1H-indol-5-yl}oxy)-3,5-bis(trifluoro-methyl)-phenyl] acetic acid Example 700
Fluoro[4-({3-[(4-fluorophenyl)sulphonyl]-1H-indol-5-yl}oxy)-3,5-bis(trifluoro-methyl)-phenyl]acetic acid Example 701
[4-({3-[(4-Chlorophenyl)sulphonyl]-1H-indol-5-yl}oxy)-3,5-bis(trifluoromethyl)-phenyl]-(fluoro) acetic acid Example 702
[4-{[3-(4-Chlorobenzyl)-1H-indol-5-yl]oxy}-3,5-bis(trifluoromethyl)phenyl]-(fluoro)acetic acid Example 703
Fluoro[4-{[3-(4-fluorobenzyl)-1H-indol-5-yl]oxy}-3,5-bis(trifluoromethyl)phenyl]-acetic acid

What is claimed is:
1. Compounds of the general formula (I)

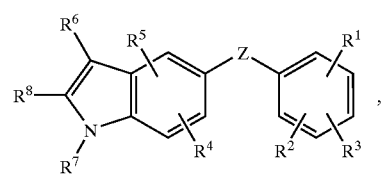

in which
Z represents O, S, SO, $SO_2$, $CH_2$, CHF, $CF_2$ or represents $NR_9$, in which $R^9$ denotes hydrogen or $(C_1-C_4)$-alkyl,
$R^1$ and $R^2$ are identical or different and represent hydrogen, halogen, cyano, $(C_1-C_6)$-alkyl, $CF_3$, $CHF_2$, $CH_2F$, vinyl or $(C_3-C_7)$-cycloalkyl, where at least one of the two substituents is unequal to hydrogen and in the ortho position to the bridge bond, $R^3$ represents a group of the formula

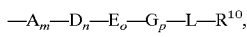

in which

A represents O, S, $NR^{11}$ or represents the group —$(CR^{12}$=$CR^{13})$—, in which $R^{11}$ denotes hydrogen or $(C_1-C_4)$-alkyl, and $R^{12}$ and $R^{13}$ are identical or different and denote hydrogen, cyano, $(C_1-C_4)$-alkyl or $(C_1-C_4)$-alkoxy, D represents a straight-chain $(C_1-C_3)$-alkylene group, which can be mono- or polysubstituted, identically or differently, by $(C_1-C_4)$-alkyl, hydroxyl, $(C_1-C_4)$-alkoxy, halogen, amino, mono-$(C_1-C_4)$-alkylamino, mono-$(C_1-C_4)$-acylamino or $(C_1-C_4)$-alkoxycarbonylamino, E and L independently of one another represent a C(O) or $SO_2$ group, G represents $NR^{14}$, in which $R^{14}$ denotes hydrogen or $(C_1-C_4)$-alkyl, or represents a straight-chain $(C_1-C_3)$-alkylene group, which can be mono- or polysubstituted, identically or differently, by $(C_1-C_4)$-alkyl, hydroxyl, $(C_1-C_4)$-alkoxy, halogen, amino, mono- or di-$(C_1-C_4)$-alkylamino or mono-$(C_1-C_4)$-acylamino, m, n, o and p independently of one another in each case represent the number 0 or 1, with the proviso that in the case that L represents a C=O-group, the sum (m+n+o+p) is unequal to the number 0, and in the case that m and o in each case represent the number 1, A represents the radical $NR^{11}$ and E and L in each case represent a C=O-group, the sum (n+p) is unequal to the number 0, and $R^{10}$ represents $OR^{15}$, $NR^{16}R^{17}$, $(C_1-C_{10})$-alkyl, $(C_3-C_8)$-cycloalkyl, $(C_2-C_6)$-alkenyl, $(C_6-C_{10})$-aryl, $(C_6-C_{10})$-arylmethyl or represents a saturated, partly unsaturated or aromatic 5- to 10-membered heterocycle having up to four identical or different heteroatoms from the group consisting of N, O and/or S, where the above-mentioned radicals are optionally substituted by one, two or three identical or different substituents selected from the group consisting of halogen, hydroxyl, oxo, cyano, nitro, amino, $NR^{18}R^{19}$, trifluoromethyl, $(C_1-C_6)$-alkyl, $(C_1-C_6)$-alkoxy optionally substituted by $R^{20}$, $(C_3-C_8)$-cycloalkyl, $(C_6-C_{10})$-aryl, which for its part is optionally substituted by halogen, $(C_1-C_4)$-alkyl, $(C_1-C_4)$-alkoxy, trifluoromethyl, nitro or cyano; —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_8)$-cycloalkyl, which for their part are optionally mono- or polysubstituted, identically or differently, by halogen, hydroxyl, amino, carboxyl, $(C_1-C_4)$-alkoxy, $(C_1-C_4)$-alkoxycarbonyl, $(C_1-C_4)$-alkoxy-carbonylamino, $(C_1-C_5)$-alkanoyloxy, a heterocycle or phenyl which is optionally substituted by halogen or hydroxyl, or the group
—L—$R^{10}$ represents a group of the formula

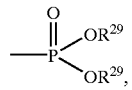

in which
$R^{29}$ denotes hydrogen or $(C_1-C_4)$-alkyl, or
$R^3$ represents a group of the formula

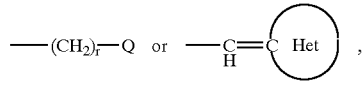

in which
Q represents a 5- to 6-membered saturated, partly unsaturated or aromatic heterocycle having up to four identical or different heteroatoms from the group consisting of N, O and/or S, which for its part is optionally mono- to trisubstituted, identically or differently, by oxo (=O), thioxo (=S), hydroxyl, $(C_1-C_6)$-alkyl or phenyl, r represents the number 0, 1 or 2,
and
the ring Het denotes a 5- to 6-membered saturated or partly unsaturated heterocycle having up to three identical or different heteroatoms from the group consisting of N, O and/or S, which is optionally mono- to trisubstituted, identically or differently, by oxo (=O), thioxo (=S), hydroxyl, $(C_1-C_6)$-alkyl or phenyl, $R^4$ and $R^5$ are identical or different and in each case represent hydrogen, hydroxyl, halogen, cyano, nitro, $(C_1-C_4)$-alkyl or the radical of the formula $NR^{30}R^{31}$, where $R^{30}$ and $R^{31}$ have the meaning indicated for $R^{15}$ and independently of one another can be identical to or different from this substituent, $R^6$ represents hydrogen, halogen or represents a group of the formula

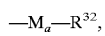

in which
M represents a carbonyl group, a sulphonyl group or a methylene group,
a represents the number 0 or 1,
and
$R^{32}$ has the meaning of $R^{10}$ indicated above and can be identical to or different from this substituent, $R^7$ represents hydrogen or represents an acyl group which can be removed under physiological conditions with formation of an NH function, preferably represents hydrogen or acetyl, and
$R^8$ has the meaning of $R^6$ indicated above and can be identical to or different from this substituent, and their pharmaceutically tolerable salts, solvates, hydrates and hydrates of the salts.

2. Compounds according to claim 1,
in which
Z represents O, S or $CH_2$, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_5)$-cycloalkyl, where at least one of the two substituents is unequal to hydrogen and is in the ortho position to the bridge bond, in particular both substituents are unequal to hydrogen and both are in the ortho position, $R^3$ represents a group of the formula

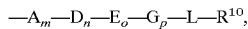

in which

A represents O, S, $NR^{11}$ or represents the group $-(CR^{12}=CR^{13})-$, in which $R^{11}$ denotes hydrogen or methyl, and $R^{12}$ and $R^{13}$ are identical or different and denote hydrogen or methoxy, D represents a straight-chain $(C_1-C_3)$-alkylene group which can be mono- or disubstituted, identically or differently, by $(C_1-C_4)$-alkyl, hydroxyl, methoxy, ethoxy, fluorine, chlorine, amino, mono-$(C_1-C_4)$-alkylamino or mono-$(C_1-C_4)$-acylamino, E represents a C(O) group, L represents a C(O) or $SO_2$ group, G represents an NH group or represents a straight-chain $(C_1-C_3)$-alkylene group, which can be mono- or disubstituted, identically or differently, by methyl, ethyl, hydroxyl, methoxy, fluorine, chlorine, amino, methylamino or acetylamino, m, n, o and p independently of one another in each case represent the number 0 or 1, with the proviso that in the case that L represents a C=O-group, the sum (m+n+o+p) is unequal to the number 0, and in the case that m and o in each case represent the number 1, A represents the radical $NR^{11}$ and L represents a C=O-group, the sum (n+p) is unequal to the number 0, and $R^{10}$ represents $OR^{15}$, $NR^{16}R^{17}$, $(C_1-C_6)$-alkyl, $(C_3-C_7)$-cycloalkyl, naphthyl, phenyl, benzyl or represents a saturated, partly unsaturated or aromatic 5- to 6-membered heterocycle having up to four identical or different heteroatoms from the group consisting of N, O and/or S, where the abovementioned radicals are optionally substituted by one, two or three identical or different substituents selected from the group consisting of halogen, hydroxyl, oxo, cyano, nitro, amino, $NR^{18}R^{19}$, trifluoromethyl, $(C_1-C_4)$-alkyl, $(C_1-C_4)$-alkoxy optionally substituted by $R^{20}$, $(C_3-C_6)$-cycloalkyl, $-O-C(O)-R^{21}$, $-C(O)-OR^{22}$, $-C(O)-NR^{23}R^{24}$, $-SO_2-NR^{25}R^{26}$, $-NH-C(O)-R^{27}$ and $-NH-C(O)-OR^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or polysubstituted, identically or differently, by halogen, hydroxyl, amino, carboxyl, $(C_1-C_4)$-alkoxy, $(C_1-C_4)$-alkoxycarbonyl, $(C_1-C_4)$-alkoxy-carbonylamino, $(C_1-C_5)$-alkanoyloxy, a heterocycle or phenyl which is optionally substituted by halogen or hydroxyl, or $R^3$ represents a group of the formula

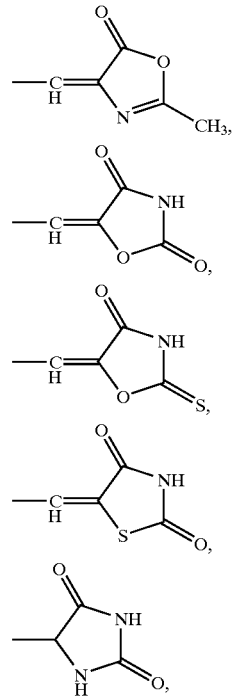

$R^4$ and $R^5$ are identical or different and in each case represent hydrogen, halogen or $(C_1-C_4)$-alkyl, $R^6$ represents hydrogen, halogen or a group of the formula

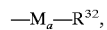

in which

M represents a carbonyl group, a sulphonyl group or a methylene group, a represents the number 0 or 1, and $R^{32}$ represents $(C_1-C_{10})$-alkyl, $(C_3-C_7)$-cycloalkyl, $(C_2-C_4)$-alkenyl, naphthyl, phenyl, benzyl, pyridyl, pyridazinyl or pyridazinonyl, where the abovementioned radicals are optionally substituted by one, two or three identical or different substituents selected from the group consisting of halogen, hydroxyl, cyano, nitro, amino, $NR^{18}R^{19}$, trifluoromethyl, $(C_1-C_4)$-alkyl, $(C_1-C_4)$-alkoxy, $(C_3-C_7)$-cycloalkyl, phenyl, which for its part is optionally substituted by halogen, $(C_1-C_4)$-alkyl, $(C_1-C_4)$-alkoxy, trifluoromethyl, nitro or cyano, $-O-C(O)-R^{21}$, $-C(O)-OR^{22}$, $-C(O)-NR^{23}R^{24}$, $-SO_2-NR^{25}R^{26}$, $-NH-C(O)-R^{27}$ and $-NH-C(O)-OR^{28}$, where $R^{18}$, $R^{19}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or polysubstituted, identically or differently, by halogen, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or phenyl which is optionally substituted by halogen or hydroxyl, $R^7$ represents hydrogen, and $R^8$ has the meaning of $R^6$ indicated above and can be identical to or different from this substituent, and their pharmaceutically tolerable salts, solvates, hydrates and hydrates of the salts.

3. Compounds according to claim 1, in which

Z represents O or $CH_2$, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_5)$-cycloalkyl, where at least one of the two substituents is unequal to hydrogen and in the ortho position to the bridge bond, in particular both substituents are unequal to hydrogen and both are in the ortho position, $R^3$ represents a group of the formula

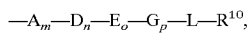

in which

A represents O, S or NH,

D represents a straight-chain $(C_1-C_3)$-alkylene group, which can be mono- or disubstituted, identically or differently, by methyl, ethyl, hydroxyl, methoxy, fluorine, amino or acetylamino, E represents a C(O) group, L represents a C(O) or $SO_2$ group, G represents an NH group or represents a methylene group, m, n, o and p independently of one another in each case represent the number 0 or 1, with the proviso that in the case that L represents a C=O group , the sum (m+n+o+p) is unequal to the number 0, and in the case that m and o in each case represent the number 1, A represents the radical NH and L represents a C=O group, the sum (n+p) is unequal to the number 0, and $R^{10}$ represents $OR^{15}$, $NR^{16}R^{17}$, $(C_1-C_6)$-alkyl, phenyl, benzyl or represents an aromatic 5- to 6-membered heterocycle having up to four identical or different heteroatoms from the group consisting of N, O and/or S, where the abovementioned radicals are optionally substituted by one, two or three identical or different substituents selected from the group consisting of fluorine, chlorine, hydroxyl, oxo, cyano, nitro, amino, $NR^{18}R^{19}$, trifluoromethyl, $(C_1-C_4)$-alkyl, $(C_1-C_4)$-alkoxy optionally substituted by $R^{20}$, $(C_3-C_6)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- to disubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonylamino, $(C_1-C_5)$-alkanoyloxy, a heterocycle or phenyl which is optionally substituted by fluorine, chlorine or hydroxyl, $R^4$ and $R^5$ are identical or different and in each case represent hydrogen, fluorine, chlorine or methyl, $R^6$ represents hydrogen, halogen or a group of the formula

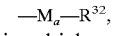

in which

M represents a sulphonyl group or a methylene group, a represents the number 0 or 1, and $R^{32}$ represents $(C_1-C_{10})$-alkyl, $(C_3-C_7)$-cycloalkyl, phenyl, benzyl, pyridyl, pyridazinyl or pyridazinonyl, where the abovementioned radicals are optionally substituted by one or two identical or different substituents selected from the group consisting of fluorine, chlorine, bromine, hydroxyl, cyano, nitro, amino, $NR^{18}R^{19}$, trifluoromethyl, $(C_1-C_4)$-alkyl, $(C_1-C_4)$-alkoxy, $(C_3-C_7)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or disubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonyl-amino, $(C_1-C_5)$-alkanoyloxy, a heterocycle or phenyl which is optionally substituted by fluorine, chlorine or hydroxyl, $R^7$ represents hydrogen, $R^8$ represents hydrogen, carboxyl, $(C_1-C_4)$-alkoxycarbonyl, $(C_1-C_6)$-alkyl, $(C_3-C_7)$-cycloalkyl, phenyl, benzyl, pyridyl, phenylsulphonyl or benzylsulphonyl, where the abovementioned radicals are optionally substituted by one or two identical or different substituents selected from the group consisting of fluorine, chlorine, bromine, hydroxyl, cyano, nitro, amino, $NR^{18}R^{19}$, trifluoromethyl, $(C_1-C_4)$-alkyl, $(C_1-C_4)$-alkoxy, $(C_3-C_6)$-cycloalkyl, —O—C(O)—$R^{21}$, —C(O)—$OR^{22}$, —C(O)—$NR^{23}R^{24}$, —$SO_2$—$NR^{25}R^{26}$, —NH—C(O)—$R^{27}$ and —NH—C(O)—$OR^{28}$, where $R^{18}$, $R^{19}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, $(C_1-C_6)$-alkyl or $(C_3-C_6)$-cycloalkyl, which for their part are optionally mono- or polysubstituted, identically or differently, by fluorine, chlorine, hydroxyl, amino, carboxyl, $(C_1-C_4)$-alkoxy, $(C_1-C_4)$-alkoxycarbonyl, $(C_1-C_4)$-alkoxycarbonyl-amino, $(C_1-C_5)$-alkanoyloxy, a heterocycle or phenyl which is optionally substituted by fluorine, chlorine or hydroxyl, and their pharmaceutically tolerable salts, solvates, hydrates and hydrates of the salts.

4. Compounds according to claim 1 in which

Z represents O, $R^1$ and $R^2$ are identical or different and represent hydrogen, fluorine, chlorine, bromine, $(C_1-C_4)$-alkyl, $CF_3$, $CHF_2$, $CH_2F$, vinyl or $(C_3-C_5)$-cycloalkyl, where at least one of the two substituents is unequal to hydrogen and in the ortho-position to the bridge bond, in particular both substituents are unequal to hydrogen and both are in the ortho-position, $R^3$ represents a group of the formula

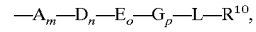

in which

A represents O, S or NH,

D represents a methylene or ethylene group, which can be mono- to disubstituted, identically or differently, by methyl, ethyl, fluorine, amino, or acetylamino, E represents a C(O) group, L represents a C(O) or $SO_2$ group, G represents an NH group or represents a methylene group, m, n, o and p independently of one another in each case represent the number 0 or 1, with the provide that in the case that L represents a C=O-group, the sum (m+n+o+p) is unequal to the number 0, and in the case that m and o in each case represent the number 1, A represents the radical NH and L represents a C=O group, the sum (n+p) is unequal to the number 0, and $R^{10}$ represents $OR^{15}$, $NR^{16}R^{17}$ or represents ($C_1$–$C_4$)-alkyl, where $R^{15}$, $R^{16}$ and $R^{17}$ are identical or different and in each case represent hydrogen, phenyl benzyl, ($C_1$–$C_6$)-alkyl or ($C_3$–$C_6$)-cycloalkyl, which for their part are optionally mono- to disubstituted, identically or differently, by fluorine, chlorine, hydroxyl, amino, carboxyl, ($C_1$–$C_4$)-alkoxy, ($C_1$–$C_4$)-alkoxycarbonyl, ($C_1$–$C_4$)-alkoxycarbonylamino, ($C_1$–$C_5$)-alkanoyloxy, a heterocycle or phenyl, $R^4$ and $R^5$ are identical or different and in each ease represent hydrogen, fluorine, chlorine or methyl, $R^6$ represents hydrogen, halogen, ($C_1$–$C_{10}$)-alkyl, ($C_3$–$C_7$)-cycloalkyl, ($C_3$–$C_7$) cycloalkylmethyl, phenyl, benzyl, pyridazinonylmethyl, phenylsulphonyl or pyridylsulphonyl, where the abovementioned aromatic radicals are optionally substituted by the one or two identical or different substituents selected from the group consisting of fluorine, chlorine, cyano, nitro, trifluoromethyl, methyl, methoxy, carboxyl or methoxycarbonyl, $R^7$ represents hydrogen, $R^8$ represents hydrogen, ($C_1$–$C_6$)-alkyl, ($C_3$–$C_7$)-cycloalkyl, phenyl, benzyl, phenylsulphonyl or benzylsulphonyl, where the abovementioned aromatic radicals arc optionally substituted by one or two identical or different substituents selected from the group consisting of fluorine, chlorine, cyano, trifluoromethyl, methyl or methoxy, and their pharmaceutically tolerable salts, solvents, hydrates and hydrates of the salts.

5. Compounds according to claim 1, in which

Z represents $CH_2$ or in particular represents oxygen, $R^1$ and $R^2$ are identical or different and represent methyl, ethyl, propyl, isopropyl, chlorine, bromine, $CF_3$, vinyl or cyclopropyl, where both substituents are in the ortho-position to the budge bond, $R^4$ and $R^5$ independently of one another represent methyl, fluorine or chlorine or in particular represent hydrogen, and $R^7$ represents hydrogen.

6. Compound according to one of claims 1 to 5, in which Z represents oxygen.

7. Compound according to claim 1, in which $R^3$ represents a group of the formula which is located in the para position to the bridge bond and in which $R^{10}$ represents hydroxyl or the radical —C(O)—$R^{10}$ has the indicated meanings of $R^{10}$ for a group which, in the sense of a prodrug, can be broken down to the carboxylic acid —C(O)—OH or its salts.

8. Compounds according to claim 1, in which $R^4$, $R^5$ and $R^7$ represent hydrogen.

9. Compounds according to claim 1, in which $R^1$ and $R^2$ are both situated in the ortho position to Z and represent bromine, trifluoromethyl, ethyl, cyclopropyl and in particular represent methyl or chlorine.

10. Compounds of the formula (Ia)

(Ia)

in which $R^3$ represents a group of the formula —$CH_2$—C(O)—OH, —CHF—C(O)—OH or —$CF_2$—C(O)—OH, and $R^6$ represents straight-chain or branched ($C_1$–$C_8$)-alkyl, and their pharmaceutically tolerable salts, solvates, hydrates and hydrates of the salts.

11. Medicaments comprising at least one compound of the general formula (I) or (Ia) as defined in claims 1 or 10.

12. Medicaments comprising at least one compound of the general formula (I) or (Ia) as defined in claims 1 or 10, and at least one excipient and/or vehicle customary to pharmacology.

13. Process for the production of medicaments, characterized in that at least one compound of the general formula (I) or (Ia) as defined in claims 1 or 10 is converted into a suitable administration form using excipients and vehicles.

14. Compounds of the formula (Ib)

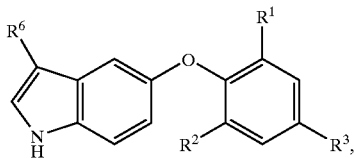

in which $R^1$ and $R^2$ are identical or different and represent bromine, trifluoromethyl, ethyl, cyclopropyl and in particular represent methyl or chlorine, $R^3$ represents a group of the formula —NH—C(O)—CH$_2$—C(O)—R$^{10}$, in which $R^{10}$ represents hydroxyl or the radical —C(O)—R$^{10}$, where $R^{10}$ represents OR$^{15}$, NR$^{16}$R$^{17}$, (C$_1$–C$_{10}$)-alkyl, (C$_3$–C$_8$)-cycloalkyl, (C$_3$–C$_6$)-alkenyl, (C$_6$–C$_{10}$)-aryl, (C$_6$–C$_{10}$)-arylmethyl or represents a saturated, partly unsaturated or aromatic 5- to 10-membered heterocycle having up to four identical or different heteroatoms from the group consisting of N, O and/or S, where the abovementioned radicals are optionally substituted by one, two or three identical or different substituents selected from the group consisting of halogen, hydroxyl, oxo, cyano, nitro, amino, NR$^{18}$R$^{19}$, trifluoromethyl, (C$_1$–C$_6$)-alkyl, (C$_1$–C$_6$)-alkoxy optionally substituted by R$^{20}$, (C$_3$–C$_8$)-cycloalkyl, (C$_6$–C$_{10}$)-aryl, which for its part is optionally substituted by halogen, (C$_1$–C$_4$)-alkyl, (C$_1$–C$_4$)-alkoxy, trifluoromethyl, nitro or cyano; —O—C(O)—R$^{21}$, —C(O)—OR$^{22}$, —C(O)—NR$^{23}$R$^{24}$, —SO$_2$—NR$^{25}$R$^{26}$, —NH—C(O)—R$^{27}$ and —NH—C(O)—OR$^{28}$, where $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$ and $R^{28}$ are identical or different and in each case represent hydrogen, phenyl, benzyl, (C$_1$–C$_6$)-alkyl or (C$_3$–C$_8$)-cycloalkyl, which for their part are optionally mono- or polysubstituted, identically or differently, by halogen, hydroxyl, amino, carboxyl, (C$_1$–C$_4$)-alkoxyl, (C$_1$–C$_4$)-alkoxycarbonyl, (C$_1$–C$_4$)-alkoxy-carbonylamino, (C$_1$–C$_5$)-alkanoyloxy, a heterocycle or phenyl which is optionally substituted by halogen or hydroxyl, which in the sense of a prodrug can be broken down to the carboxylic acid —C(O)—OH or its salts, and $R^6$ represents straight-chain or branched (C$_1$–C$_8$)-alkyl.

* * * * *